(12) United States Patent
Stroud et al.

(10) Patent No.: US 9,497,973 B2
(45) Date of Patent: Nov. 22, 2016

(54) ELASMOBRANCH-REPELLING COMPOUNDS, METHODS OF USE AND DEVICES

(76) Inventors: Eric Matthew Stroud, Oak Ridge, NJ (US); Jean Marie Pachucki, Oak Ridge, NJ (US); Michael Matthew Herrmann, Lake Hiawatha, NJ (US)

( * ) Notice: Subject to any disclaimer, the term of this patent is extended or adjusted under 35 U.S.C. 154(b) by 1165 days.

(21) Appl. No.: 11/884,190

(22) PCT Filed: Feb. 13, 2006

(86) PCT No.: PCT/US2006/005035
§ 371 (c)(1),
(2), (4) Date: Jul. 19, 2012

(87) PCT Pub. No.: WO2006/088793
PCT Pub. Date: Aug. 24, 2006

(65) Prior Publication Data
US 2010/0203154 A1    Aug. 12, 2010

Related U.S. Application Data

(60) Provisional application No. 60/652,482, filed on Feb. 12, 2005, provisional application No. 60/715,239, filed on Sep. 8, 2005.

(51) Int. Cl.
*A01N 63/00* (2006.01)
*A01N 43/60* (2006.01)
*A01P 17/00* (2006.01)
*A01N 63/02* (2006.01)

(52) U.S. Cl.
CPC .................................... *A01N 63/02* (2013.01)

(58) Field of Classification Search
None
See application file for complete search history.

(56) References Cited

U.S. PATENT DOCUMENTS

| | | | |
|---|---|---|---|
| 7,053 A * | 1/1850 | Hare ............................. | 504/102 |
| 2,389,719 A | 11/1945 | Dinsley | |
| 3,764,707 A | 10/1973 | Habersberger | |
| 4,340,587 A | 7/1982 | Antonik | |
| 4,490,360 A | 12/1984 | Antonik | |
| 4,548,764 A | 10/1985 | Munteanu et al. | |
| 4,602,099 A | 7/1986 | Parker | |
| 4,906,488 A | 3/1990 | Pera | |
| 4,909,941 A * | 3/1990 | Poll et al. ..................... | 210/635 |
| 5,134,138 A | 7/1992 | Onoue et al. | |
| 5,607,979 A | 3/1997 | McCreery | |
| 5,753,609 A | 5/1998 | Nakatsu et al. | |
| 5,989,323 A | 11/1999 | Taylor | |
| 6,028,118 A * | 2/2000 | Dupont et al. ................ | 424/548 |
| 6,606,963 B1 | 8/2003 | Wynne | |
| 6,716,441 B1 | 4/2004 | Osborne et al. | |
| 8,951,544 B2 | 2/2015 | Stroud | |
| 9,084,415 B2 | 7/2015 | Stroud | |
| 2007/0256623 A1 | 11/2007 | Stroud | |
| 2009/0038205 A1 | 2/2009 | Stroud | |
| 2010/0016346 A1 | 1/2010 | Stroud | |
| 2016/0016644 A1 | 1/2016 | Stroud | |

FOREIGN PATENT DOCUMENTS

WO    WO2006/088793    *   8/2006
WO    WO 2006/135876 A2    12/2006

OTHER PUBLICATIONS

Tester "A summary of research on sharks". University of Hawaii 1961.*
Hurley et al. "The Dogfish Scourge:Protecting Fishing Gear From Shark Attack". 1987.*
Herdwerk "New Shark Repellent Uses Chemical Signals" National Geographic News Jul. 2004.*
Mudd "High performance Liquid Chromatography-mass Spectrometry in the Analysis of Semochemicals" 1990.*
Trzaska "Keeping Sharks at Bay" Critter Chemistry Dec. 2004.*
Sisneros, et al., Surfactants as Chemical Shark Repellents: Past, Present, and Future, *Environmental Biology of Fishes*, 60:117-129, 2001.
International Search Report of International Application No. PCT/US06/05035 mailed by the International Search Authority on Jun. 14, 2006.
International Search Report of International Application No. PCT/US06/22912 mailed by the International Search Authority on Sep. 25, 2007.

* cited by examiner

*Primary Examiner* — Robert A Wax
*Assistant Examiner* — Danah Al-Awadi
(74) *Attorney, Agent, or Firm* — Hoxie & Associates LLC

(57) ABSTRACT

Elasmobranch-repelling compositions are prepared from elasmobranch carcasses. Extraction of these elasmobranch carcasses with polar solvent after a period of aerobic decay yields semiochemical repellents that induce a flight reaction in sharks when introduced into the sharks' oceanic proximity.

9 Claims, 35 Drawing Sheets

FIGURE 2 – Comparison of UV-Vis Spectrum of Semiochemicals of Carcass and Carcass Parts of Different Elasmobranch Species
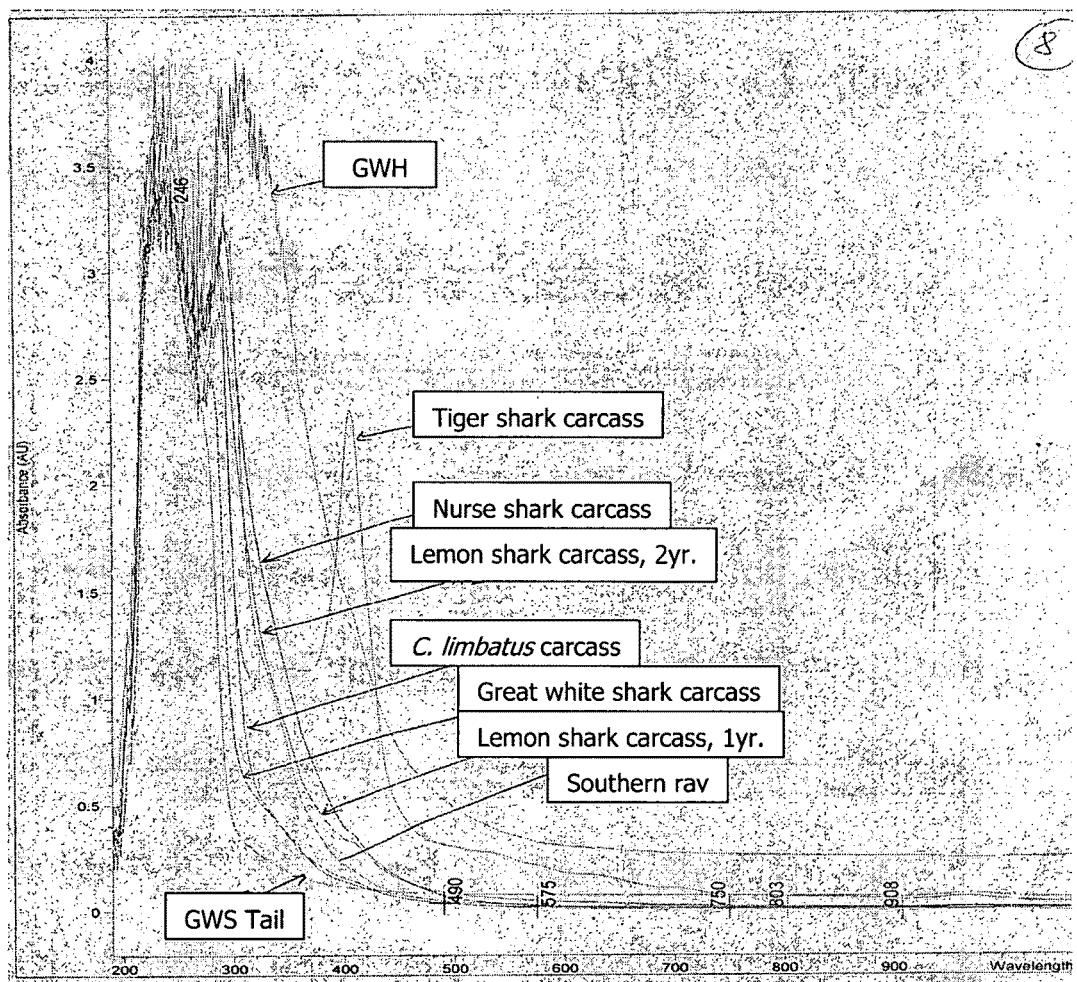

FIGURE 3 – HPLC Chromatogram of Early Eluting Components of Semiochemicals GWH and A1

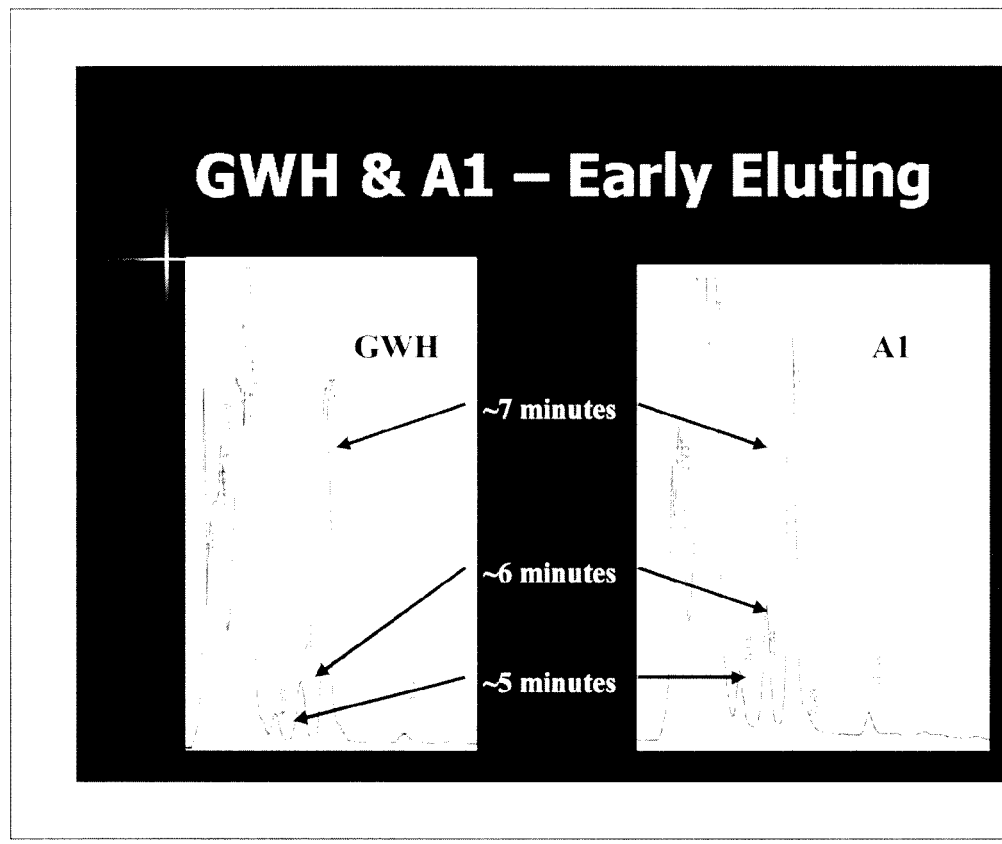

Detection: 240nm-340nm
Solvents: (1) Methanol and 0.1% acetic acid; (2) Water and 0.1% acetic acid
Ternary HPLC Pump: Gradient control
0-10 minutes: 100% methanol/acetic acid
10-12 minutes: Linear gradient to 100% water/acetic acid
12-20 minutes: 100% water/acetic acid
20-22 minutes: Linear gradient to methanol/acetic acid
22-40 minutes: 100% methanol/acetic acid
Column: Waters Novapak C18 RP 3.9x150 mm with guard column
Column heater: 25 C
Injector: 50uL loop FIGURE 4 - HPLC Chromatogram of Late Eluting Components of Semiochemicals GWH & A1

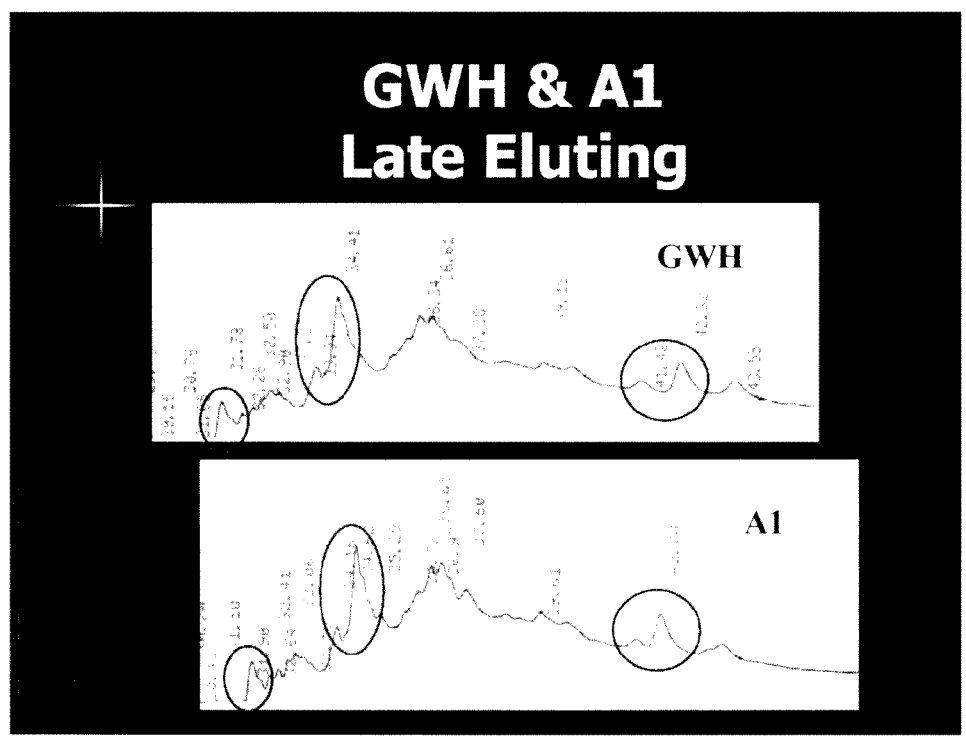

Detection: 240nm-340nm
Solvents: (1) Methanol and 0.1% acetic acid; (2) Water and 0.1% acetic acid
Ternary HPLC Pump: Gradient control
0-10 minutes: 100% methanol/acetic acid
10-12 minutes: Linear gradient to 100% water/acetic acid
12-20 minutes: 100% water/acetic acid
20-22 minutes: Linear gradient to methanol/acetic acid
22-40 minutes: 100% methanol/acetic acid
Column: Waters Novapak C18 RP 3.9x150 mm with guard column
Column heater: 25C
Injector: 50uL loop FIGURE 5 – HPLC Chromatogram of Primary Amines in Semiochemicals GWH and AI

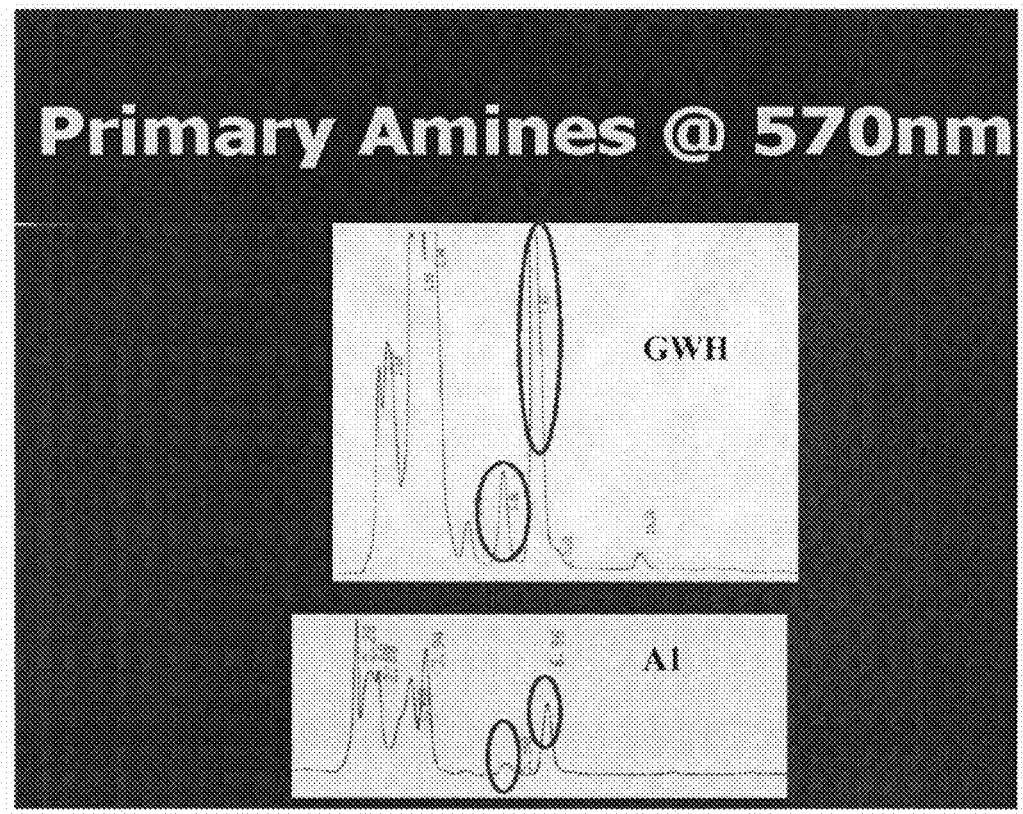

Sample derivatized with 0.1 mg ninhydrin at 130 C.
Detection: 570 nm
Solvents: (1) Methanol and 0.1% acetic acid; (2) Water and 0.1% acetic acid
Ternary HPLC Pump: Gradient control
0-10 minutes: 100% methanol/acetic acid
10-12 minutes: Linear gradient to 100% water/acetic acid
12-20 minutes: 100% water/acetic acid
20-22 minutes: Linear gradient to methanol/acetic acid
22-40 minutes: 100% methanol/acetic acid
Column: Waters Novapak C18 RP 3.9x150 mm with guard column
Column heater: 25C
Injector: 50uL loop FIGURE 6 - HPLC Chromatogram of Secondary Amines in Semiochemicals GWH and A1

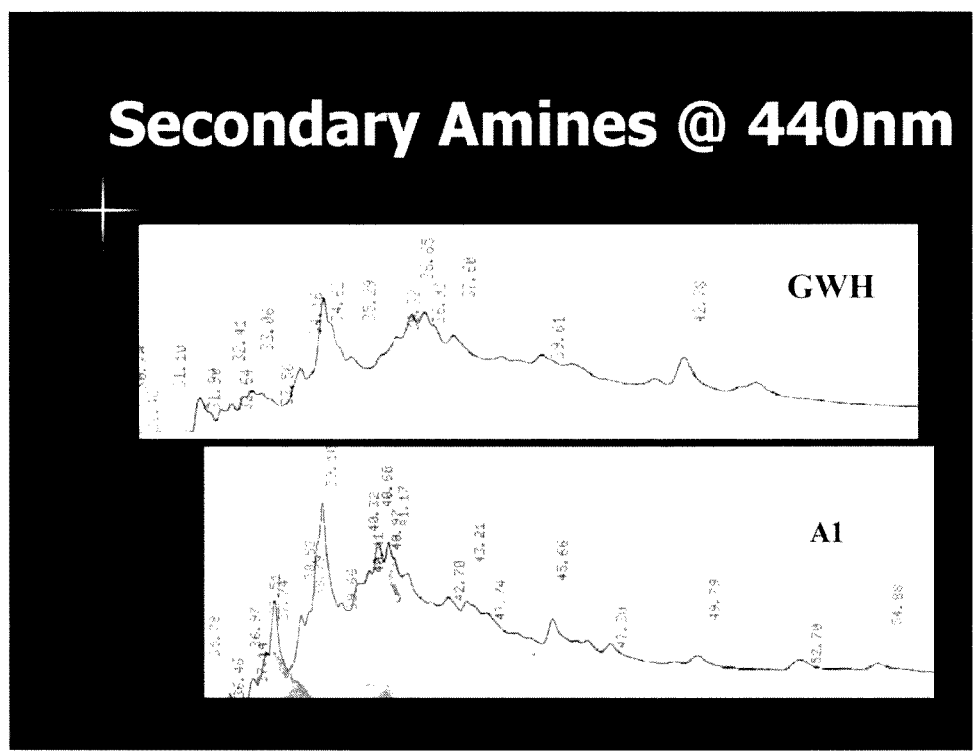

Sample derivatized with 0.1 mg ninhydrin at 130 C.
Detection: 440 nm
Solvents: (1) Methanol and 0.1% acetic acid; (2) Water and 0.1% acetic acid
Ternary HPLC Pump: Gradient control
0-10 minutes: 100% methanol/acetic acid
10-12 minutes: Linear gradient to 100% water/acetic acid
12-20 minutes: 100% water/acetic acid
20-22 minutes: Linear gradient to methanol/acetic acid
22-40 minutes: 100% methanol/acetic acid
Column: Waters Novapak C18 RP 3.9x150 mm with guard column
Column heater: 25C
Injector: 50uL loop

FIGURE 7 – GC-MS Spectrum of Semiochemical GWH
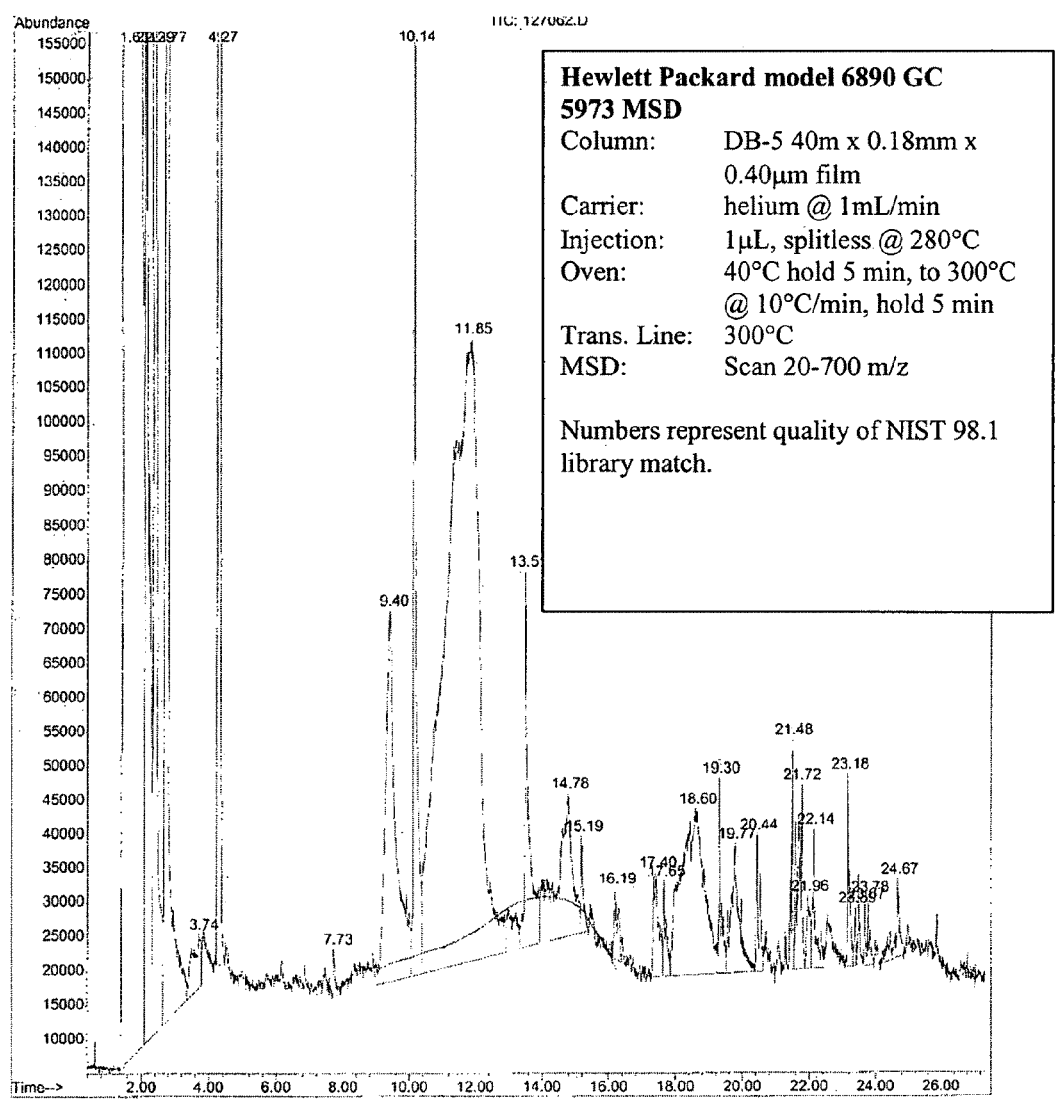

FIGURE 8 – UV-Visible Absorbance Spectrum from Semiochemical Repellent CP Derivatized with 0.1 g Ninhydrin at 40 C for 15 Minutes
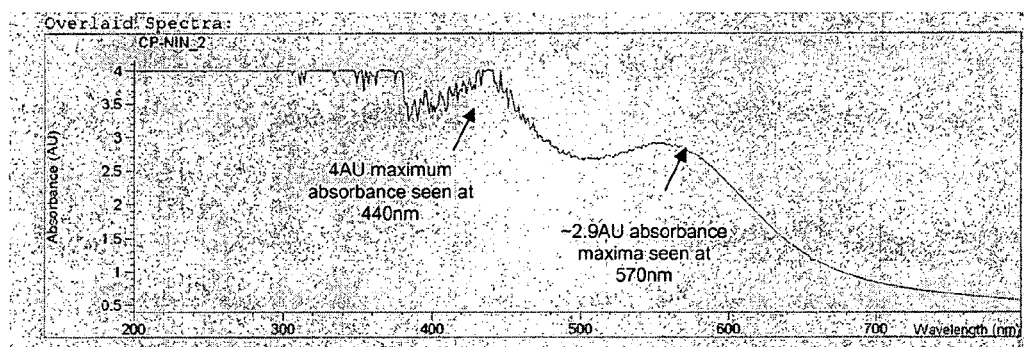
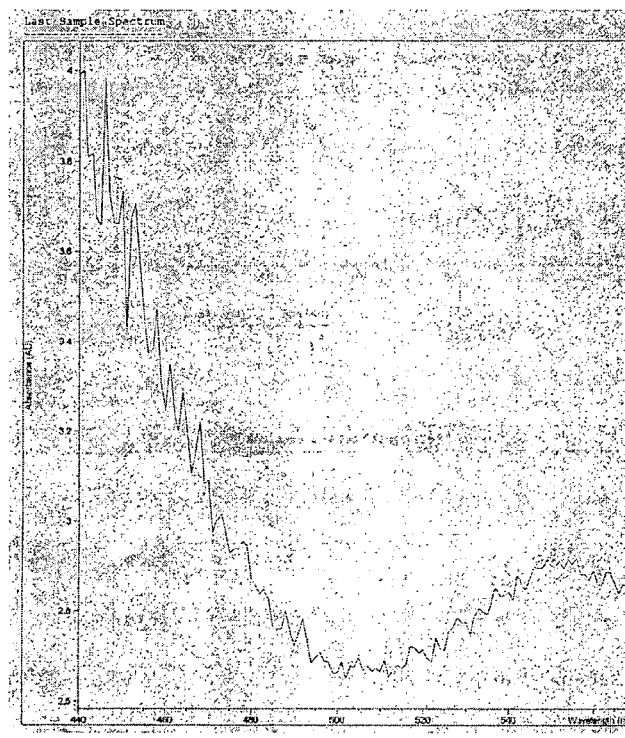

FIGURE 9 - UV-Visible Absorbance Spectrum from 50%w/w ammonium acetate (a proposed and discredited shark repellent) in water, derivatized with 0.1g ninhydrin at 40'C for 15 minutes
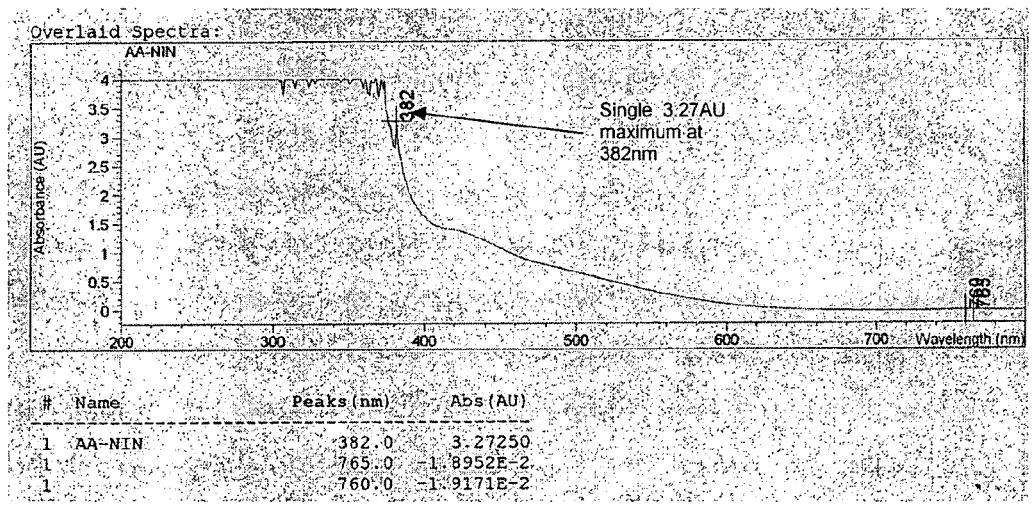
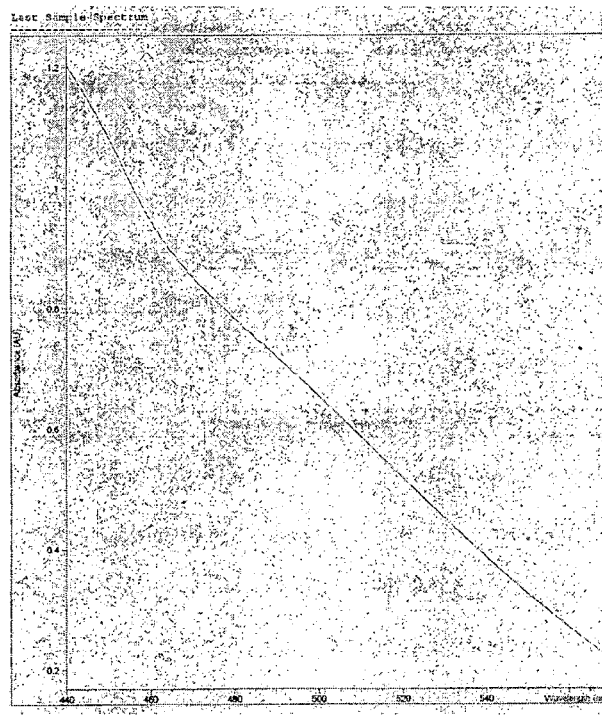

FIGURE 10 – GC-MS Chromatogram of Semiochemical CP
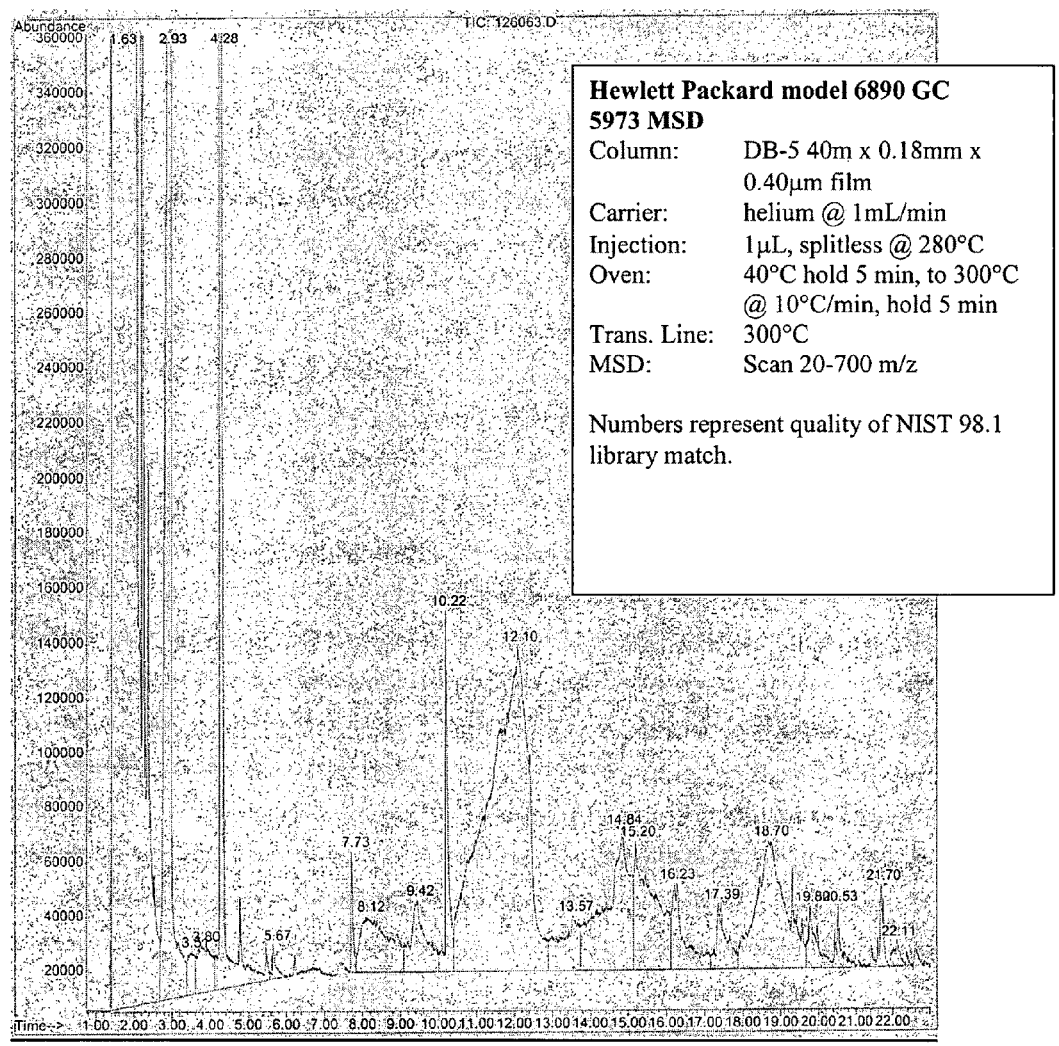

FIGURE 11 – Comparison of UV-Vis Spectra of Semiochemicals A2, A13N and SQ1
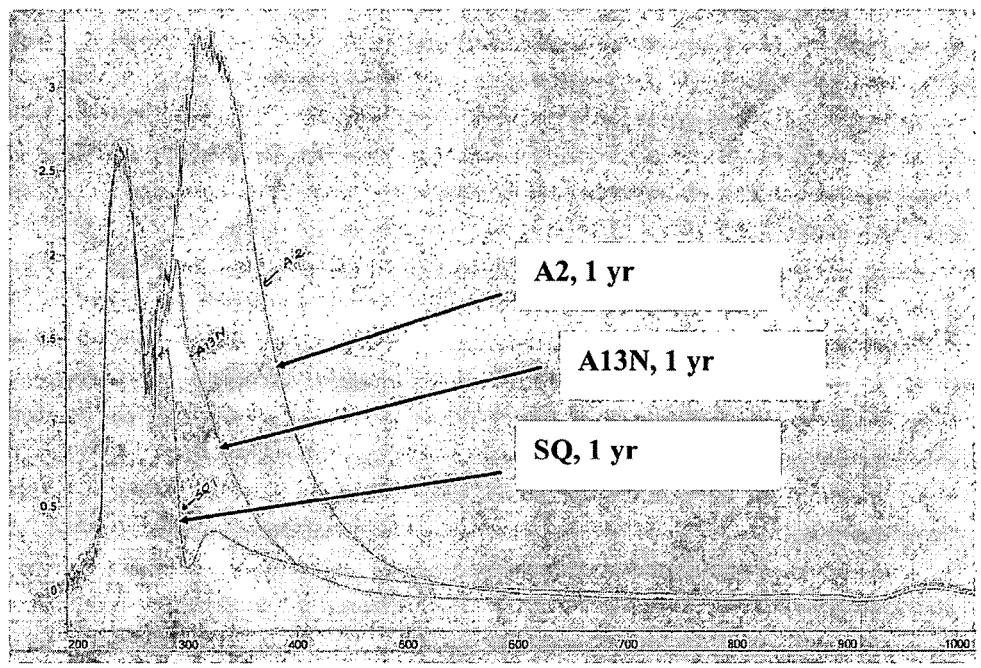
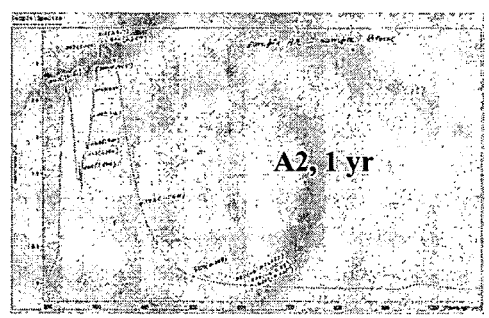
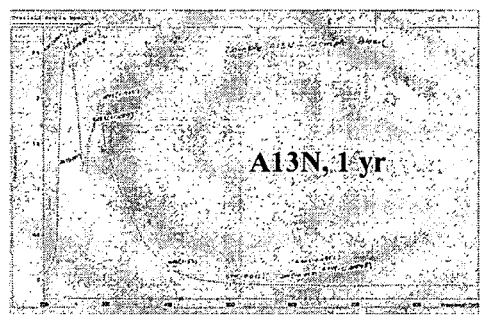
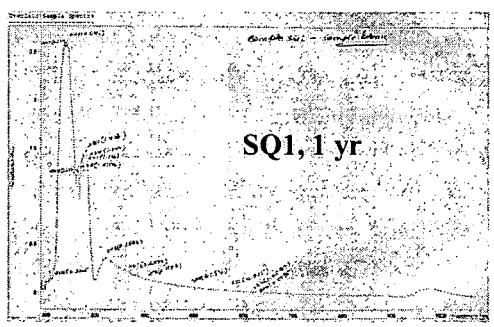

FIGURE 12 – Comparison of UV-Vis Spectrum of Semiochemical CL over Time
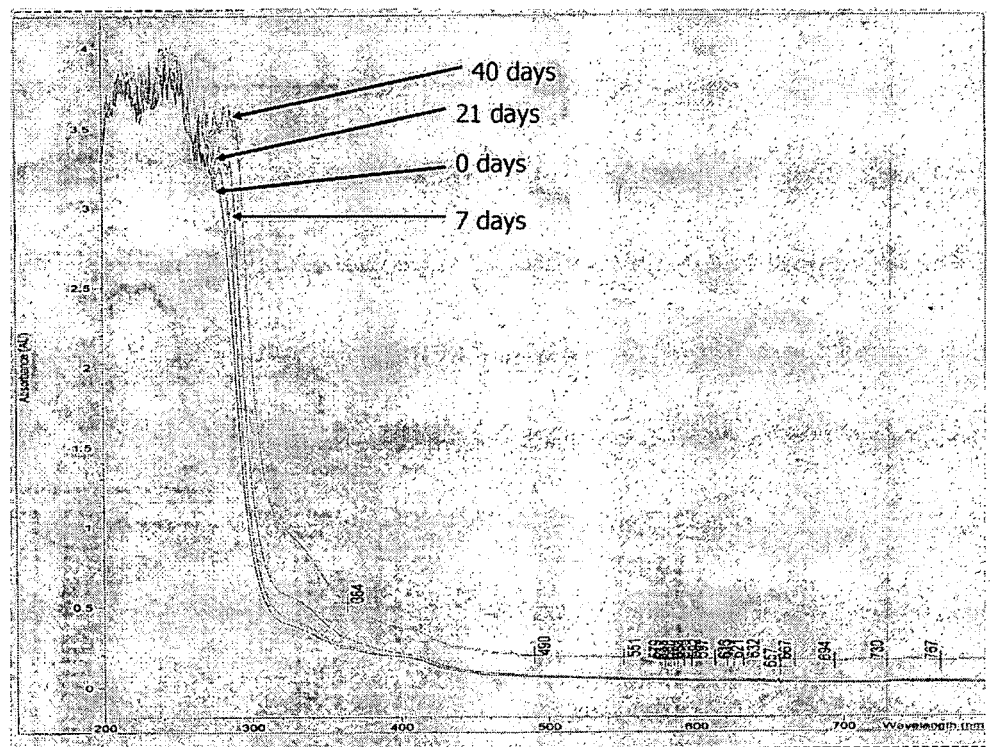

FIGURE 13 – HPLC Chromatograms of Ninhydrin-Derivatized Semiochemical A2
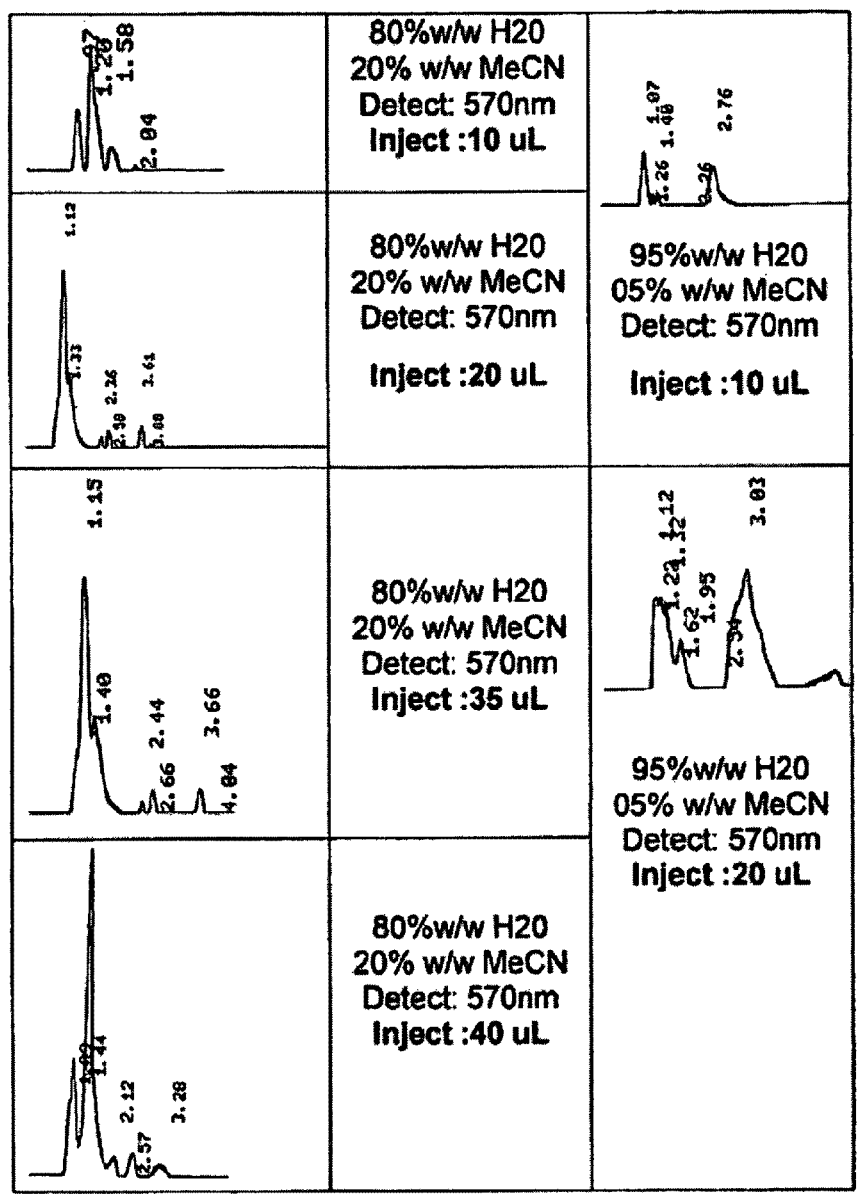

FIGURE 14 - HPLC Chromatograms of Ninhydrin-Derivatized Semiochemical A2
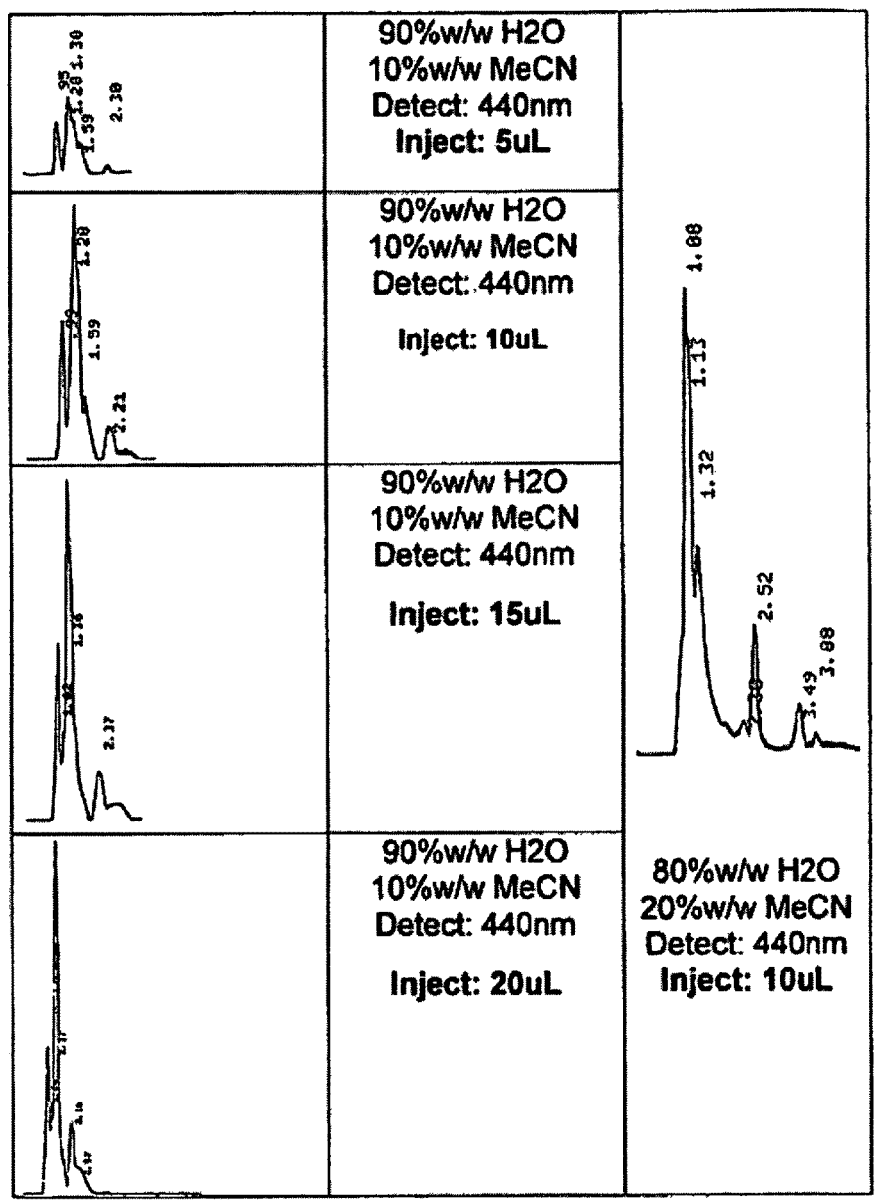

FIGURE 15 - HPLC Chromatograms of Ninhydrin-Derivatized Semiochemical A2
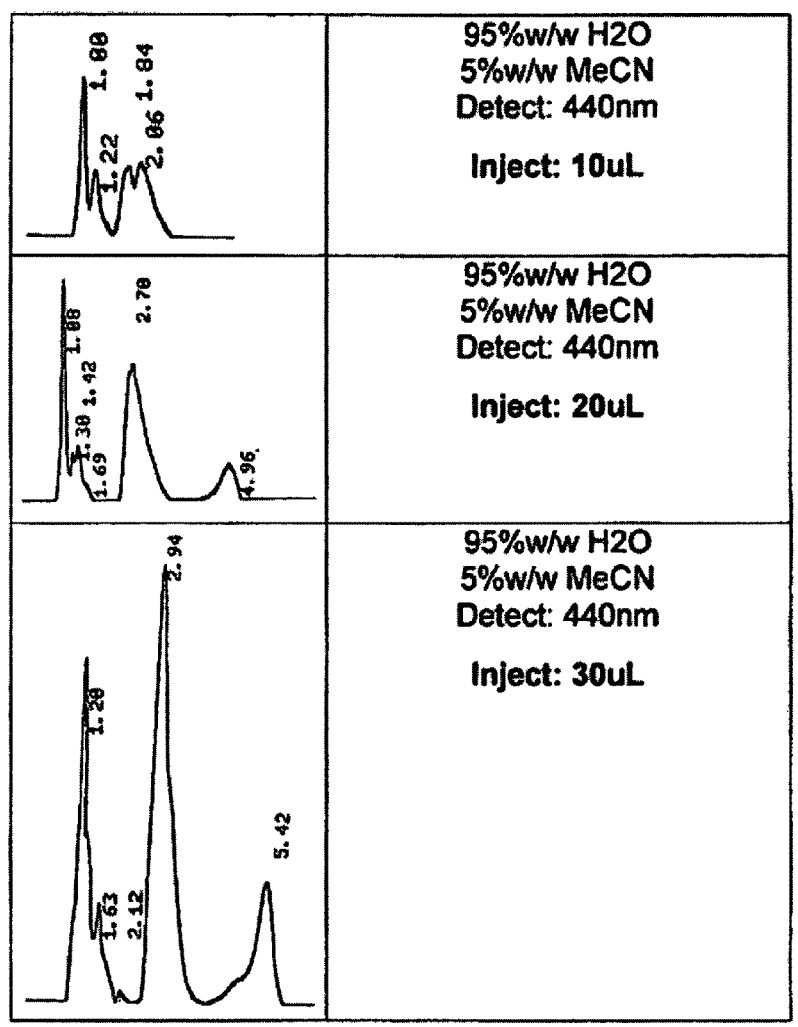

FIGURE 16 – FTIR Spectrum of Semiochemical A2
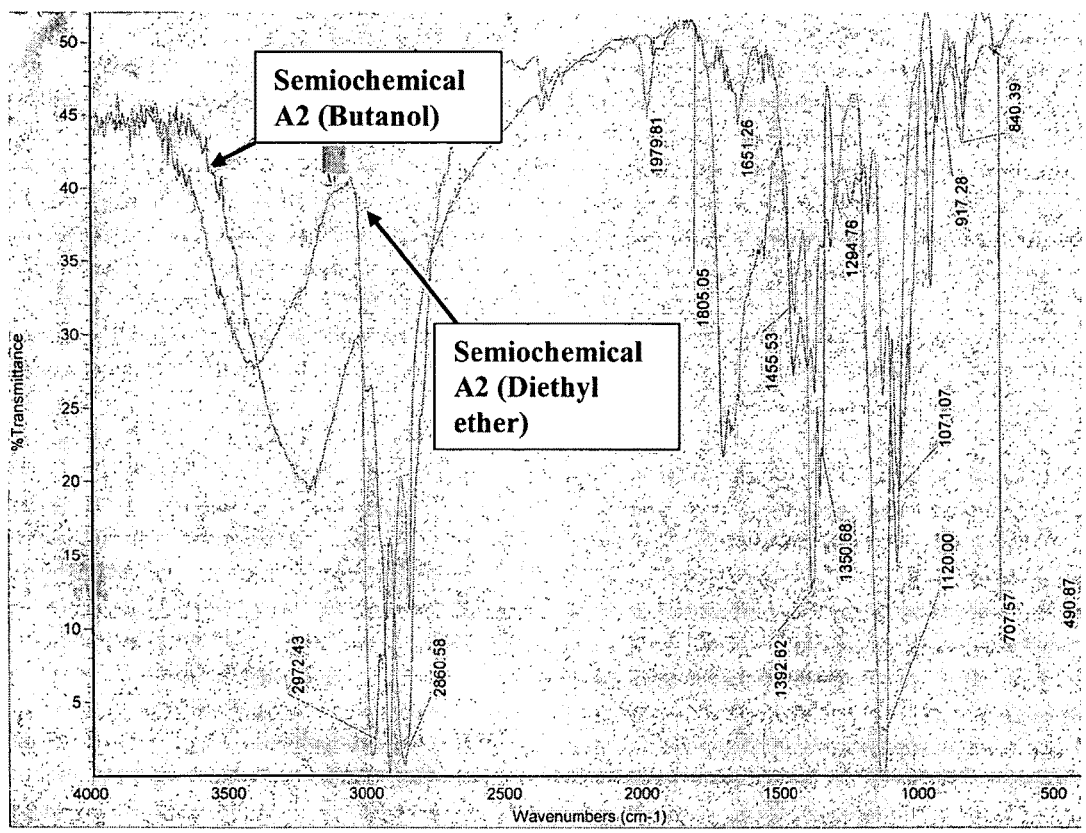

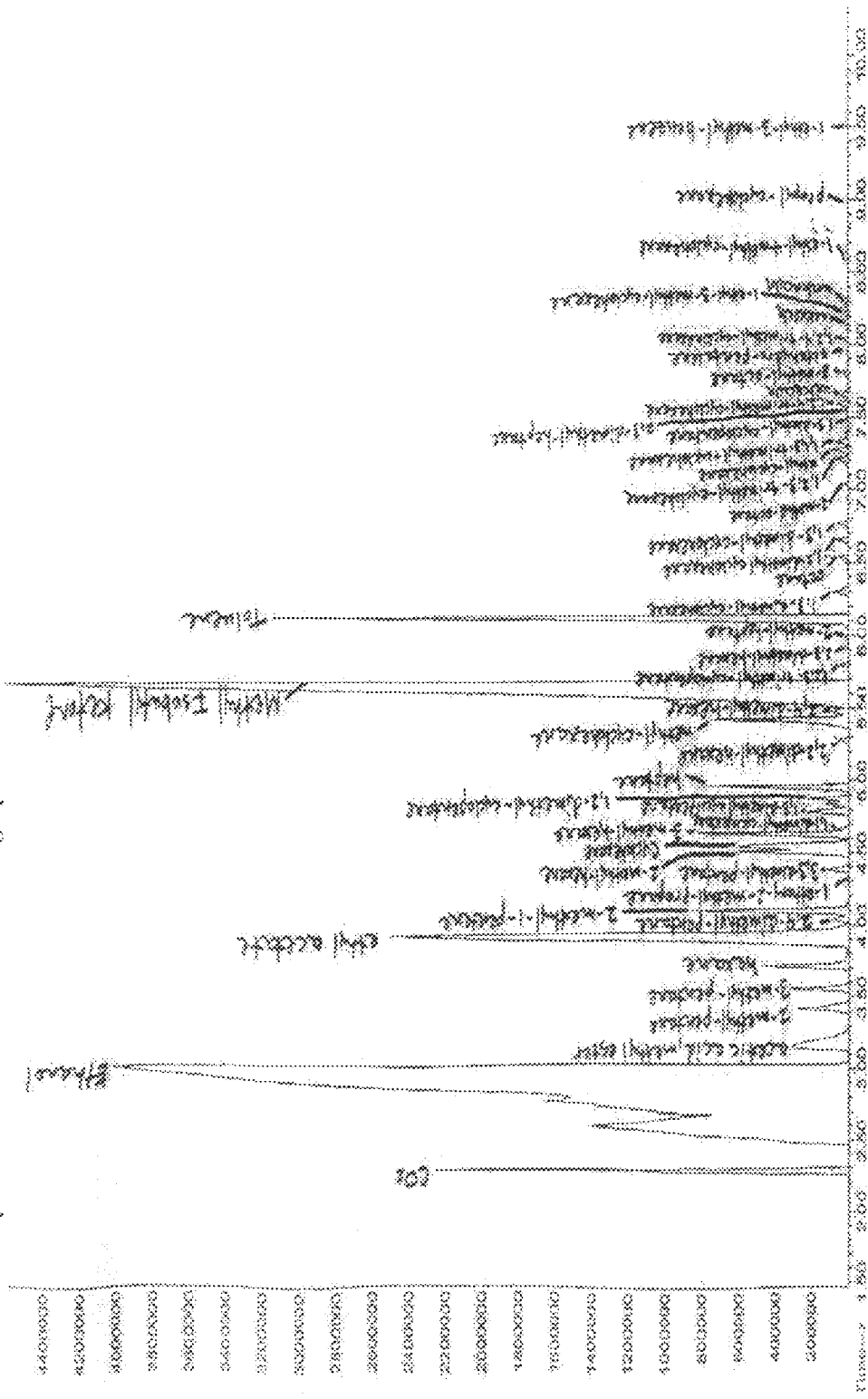

FIGURE 18 – Direct Injection Total Ion GC-MS Chromatograph of Semiochemical A2
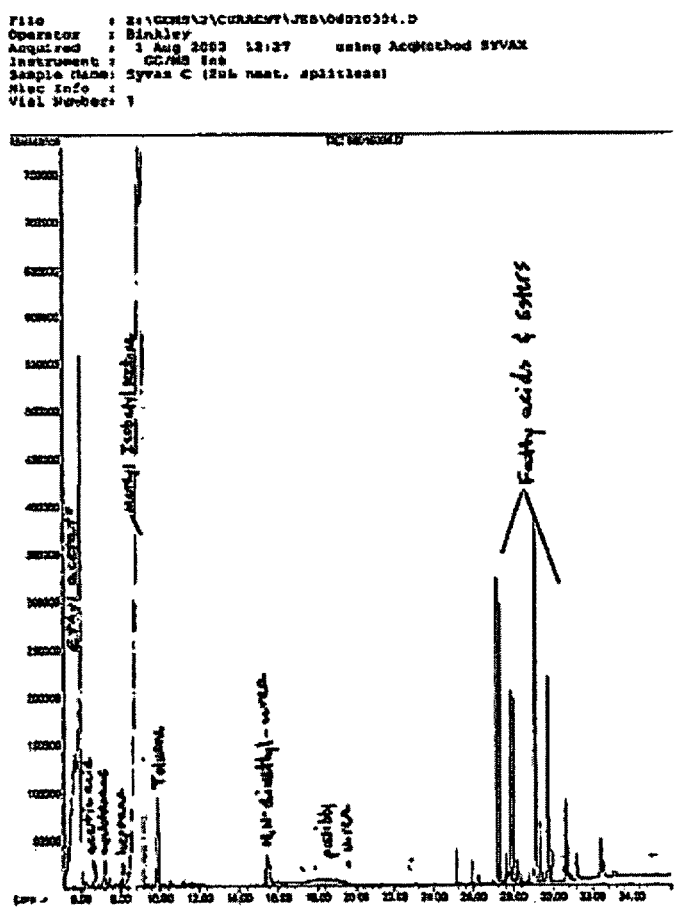

FIGURE 19 –Total Ion LC-MS Chromatograph of Semiochemical A2
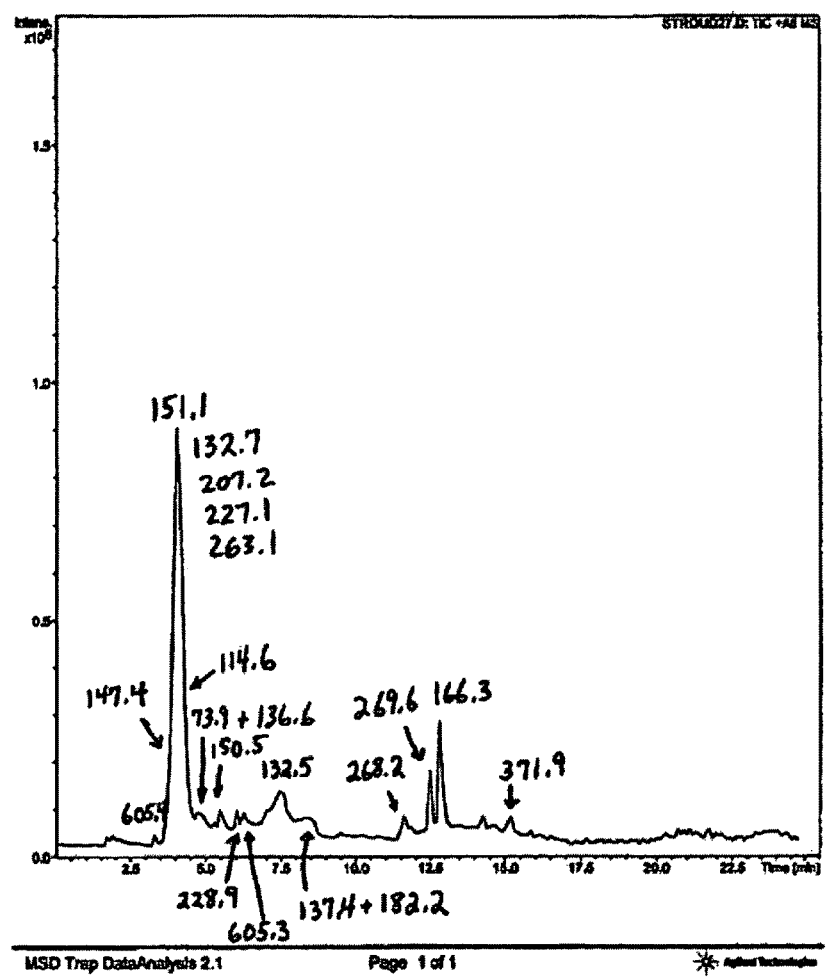

FIGURE 20 – GC-MS Chromatograph of Semiochemical CF-Composite
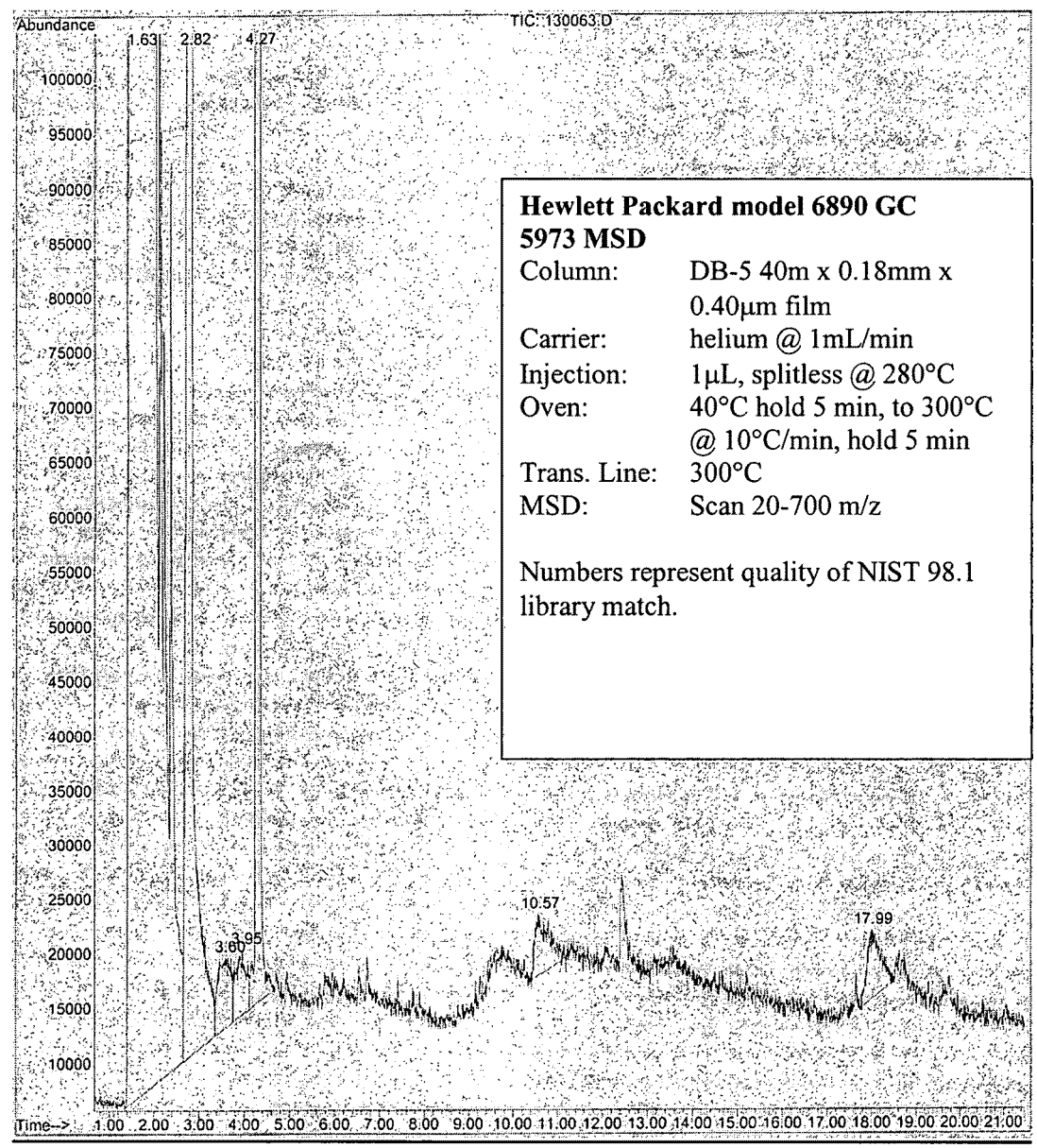

FIGURE 21 – GC-MS Chromatograph of Semiochemical B-Composite
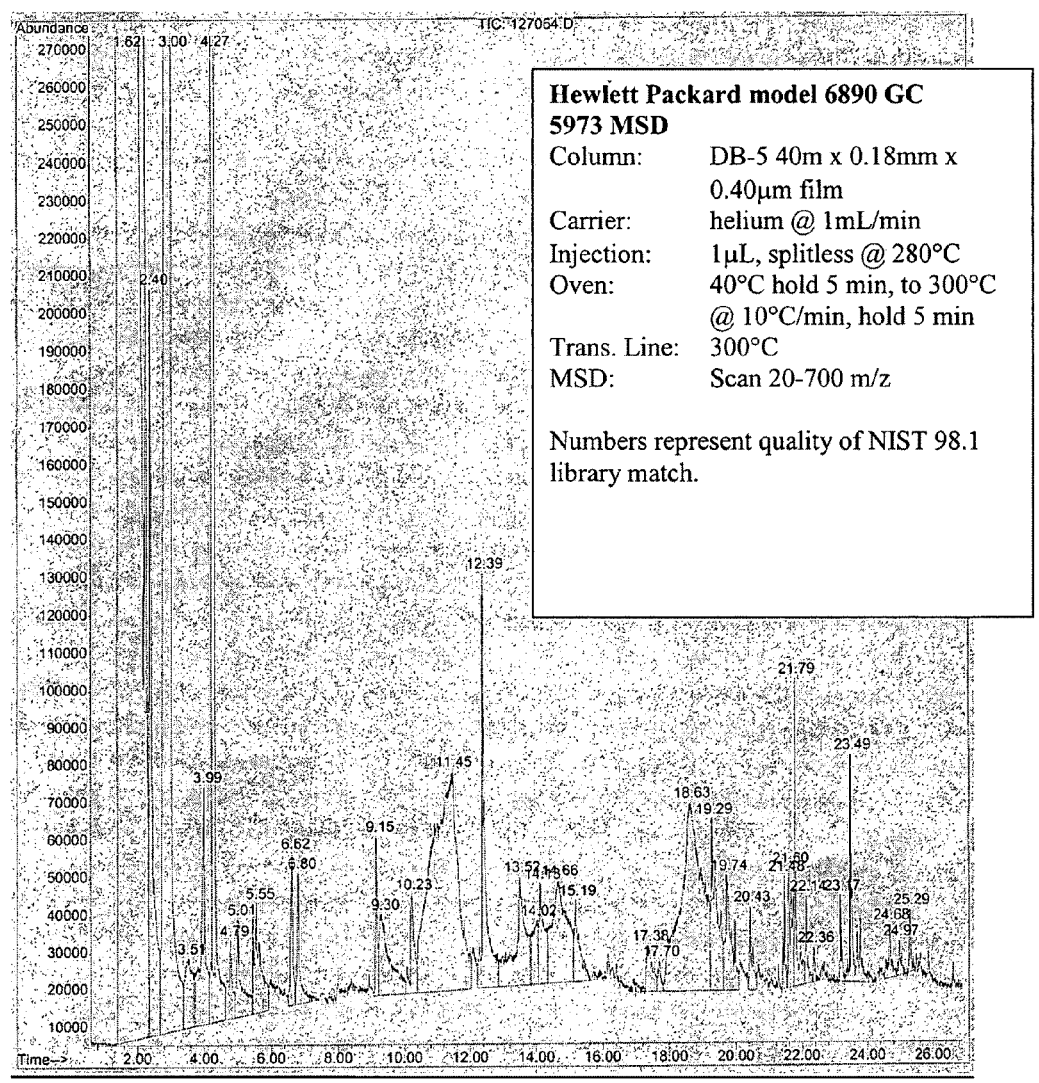

FIGURE 22 - HPLC Chromatographs of Early-Eluting Components of Degraded Semiochemicals A2 and N2

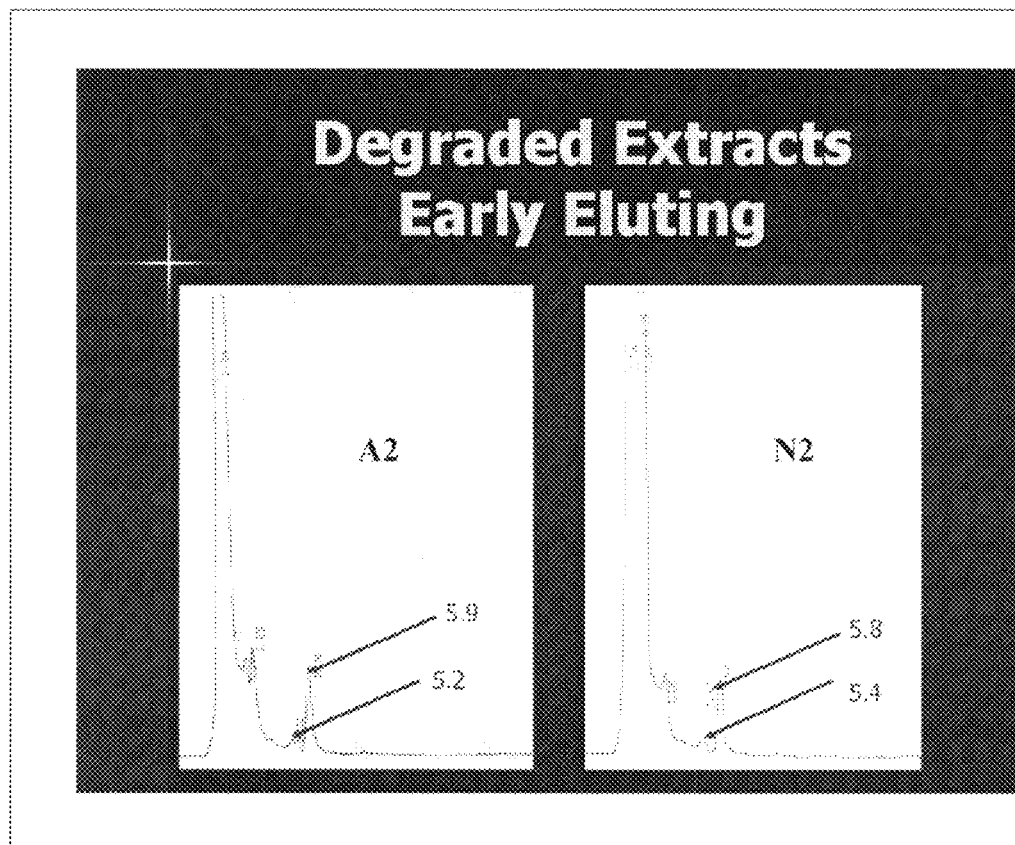

Detection: 240nm-340nm
Solvents: (1) Methanol and 0.1% acetic acid; (2) Water and 0.1% acetic acid
Ternary HPLC Pump: Gradient control
0-10 minutes: 100% methanol/acetic acid
10-12 minutes: Linear gradient to 100% water/acetic acid
12-20 minutes: 100% water/acetic acid
20-22 minutes: Linear gradient to methanol/acetic acid
22-40 minutes: 100% methanol/acetic acid
Column: Waters Novapak C18 RP 3.9x150 mm with guard column
Column heater: 25C
Injector: 50uL loop FIGURE 23 - HPLC Chromatographs of Late-Eluting Components of Degraded Semiochemicals A2 and N2

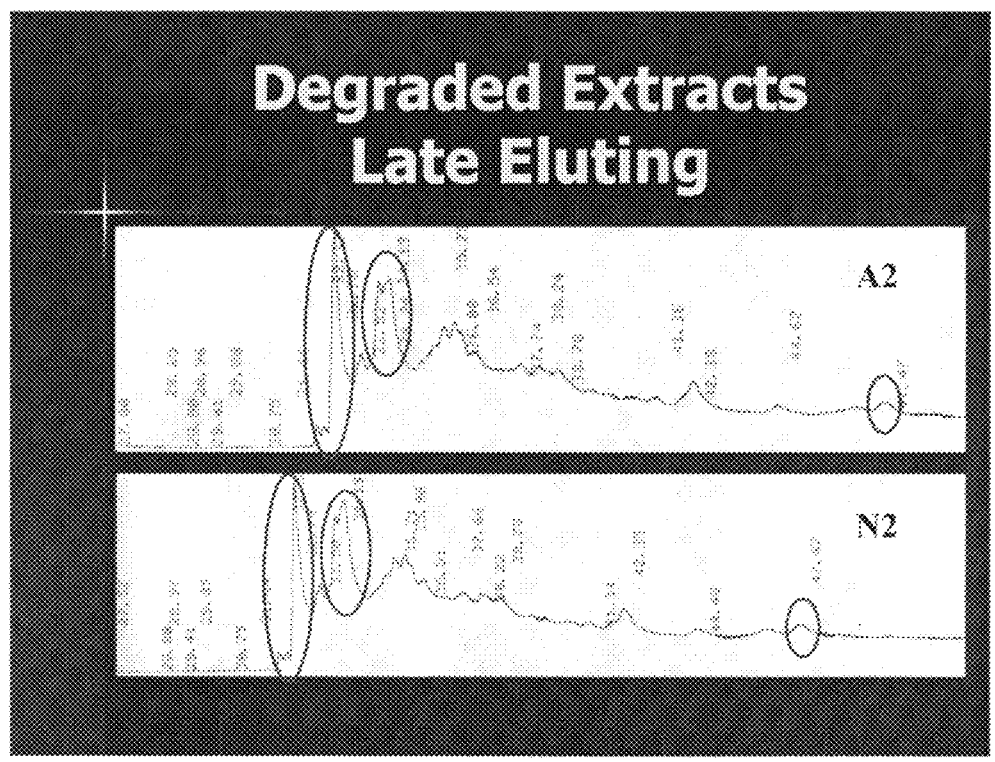

Detection: 240nm-340nm
Solvents: (1) Methanol and 0.1% acetic acid; (2) Water and 0.1% acetic acid
Ternary HPLC Pump: Gradient control
0-10 minutes: 100% methanol/acetic acid
10-12 minutes: Linear gradient to 100% water/acetic acid
12-20 minutes: 100% water/acetic acid
20-22 minutes: Linear gradient to methanol/acetic acid
22-40 minutes: 100% methanol/acetic acid
Column: Waters Novapak C18 RP 3.9x150 mm with guard column
Column heater: 25C
Injector: 50uL loop FIGURE 24
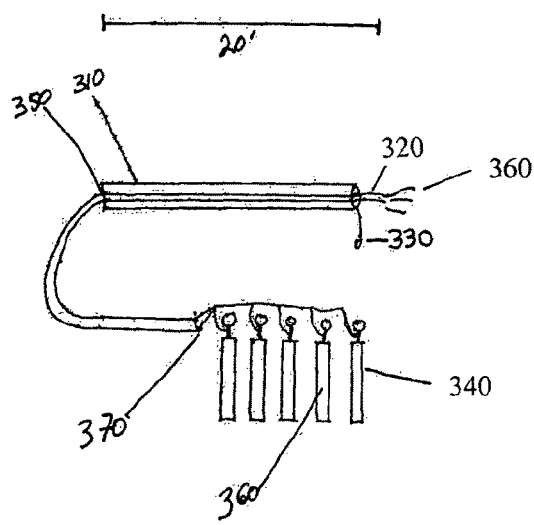
Figure 24A
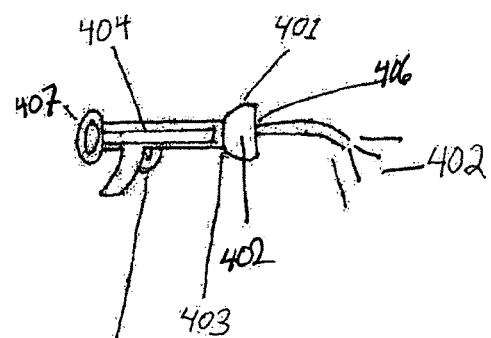
Figure 24C
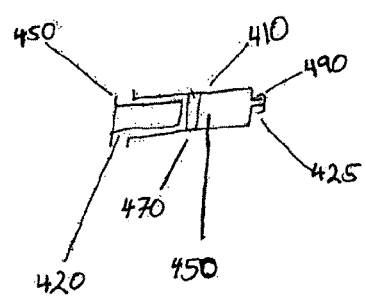
Figure 24B FIGURE 25
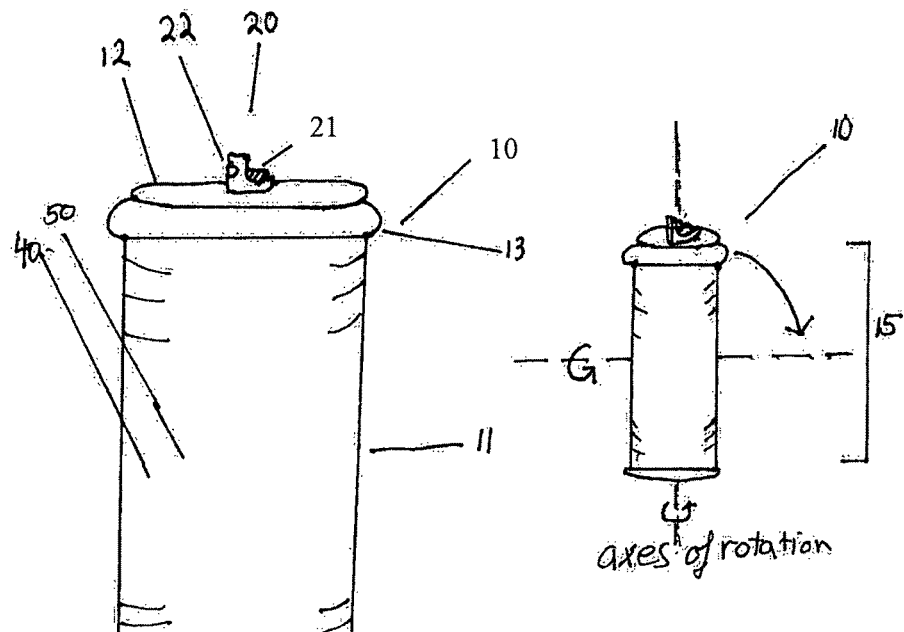
Figure 25A
Figure 25B
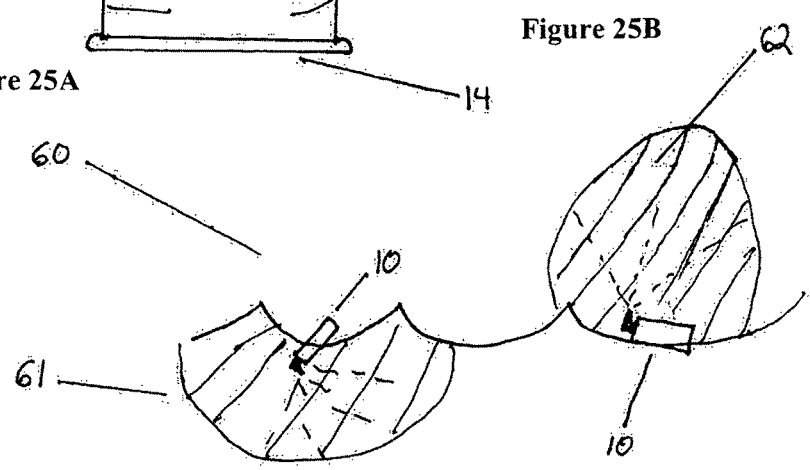
Figure 25C

ELASMOBRANCH-REPELLING COMPOUNDS, METHODS OF USE AND DEVICES

CROSS REFERENCE TO RELATED APPLICATIONS

This application is a United States Application under 35 U.S.C. 371 claiming benefit of PCT Application No. PCT/US2006/005035, filed on Feb. 13, 2006, which claims the benefit of U.S. Provisional Application No. 60/715,239, filed on Sep. 8, 2005, and U.S. Provisional Application No. 60/652,482, filed on Feb. 12, 2005, the contents of each of which are incorporated herein by reference.

This invention relates generally to elasmobranch repellents, methods of making and using such repellents and devices for administering such repellents. This invention also relates to a process for selecting elasmobranch carcasses and using polar solvents to extract semiochemicals that induce a flight reaction in elasmobranchs. Qualitative techniques are described, which allow for detection of the production of semiochemicals during the extraction process. Without being limited to a specific theory, it is believed that extracted semiochemicals are detected in elasmobranchs by olfaction because behavioral responses are achieved with very low concentrations of the inventive repellent.

BACKGROUND OF THE INVENTION

Shark attacks on humans have been recorded from ancient times. One such attack on an unlucky Mediterranean sponge diver is recorded from the third century B.C. (Thomas B. Allen, Shark Attacks: Their causes and avoidance 35 (2001)). And since the early part of the twentieth century, the populace of the United States has been riveted by sporadic stories of sensational and gruesome human encounters with sharks. As the twentieth century progressed and America's love for the seashore grew, so did its fascination with the remote but real possibility of a dangerous brush with one of these creatures. From at least 1916, shoreline municipalities began to develop physical structures to keep public bathing areas safe from the perceived danger of sharks. And through the present day, reports of shark attacks have frightened coastal communities and negatively impacted their economies as seashore revelers curtailed their beach excursions with each new and ever frightening story of voracious sharks in a particular town's waters.

As the number of humans spending time in the ocean has increased, so has the number of shark attacks and along with that increase in attacks so grows the urgent need for a repellent. Further, as the twenty-four hour news cycle continues its frenetic discussion of the threat of sharks to humans, each shark attack in the developed world appears to be reported with greater sensation and grander desperation. As such, the ever-pressing need to develop an effective shark repellent is even greater than before as the public seeks to provide itself some assurance that it will not be a victim of the next injurious encounter with a shark.

While fear of attack by sharks seems to have appeared in the United States in the early part of the twentieth century, the Second World War particularly amplified this fear when U.S. service personnel were called to combat in the dangerous and "shark infested" South Pacific. During that time, the U.S. Navy began a concerted effort to develop a chemical shark repellent to protect sailors and air personnel exposed to sharks when downed in shark-prone waters. Since then, government and private industry have worked to discover and develop a chemical shark repellent potent enough to protect humans. (Johnson and Baldridge (1985).

To establish clear criteria for government development of an effective chemical shark repellent, Johnson and Baldridge set forth a goal in 1985 of finding a chemical that would repel sharks in ocean water at 1 part per billion. While the goal was a good one, no previously-developed chemical repellent has even come close to achieving the standard.

An effective repellent would not only provide some assurance to humans bathing or adrift in waters frequented by sharks, an effective repellent would also significantly help the commercial fishing industry. Commercial longline fishing operations routinely target swordfish and tuna. However, the longline fishing hook is not selective, and it is not uncommon for more sharks to be caught than swordfish or tuna. Sharks that are caught as unintended targets are commonly called "by-catch." Often, the shark dies on the hook prior to retrieval. If a live shark is cut free during retrieval, the hook, snood and gangion are usually lost. This presents significant monetary loss as well as significant inadvertent death for millions of sharks. There has been a long-felt need to reduce by-catch losses in the fishing industry and to save the lives of many millions of sharks each year. Currently, as many as 80 species of shark are considered threatened with extinction and it is estimated that up to 100 million sharks are killed each year by humans. It is no surprise, then, that an effective repellent would satisfy a long-felt need in the commercial fishing industry.

It has been recognized for some time that development of a repellent effective against two particular orders of shark, Carcharhinoforme and Lamniformes, would provide considerable protection to humans and considerable assistance to commercial fishing. This is because nearly all of the known aggressive species of sharks and the predominant kinds of sharks that also interfere with commercial fishing are from those two orders. Orders Squaliformes and Orectolobiformes, on the other hand, represent sharks that have caused relatively few injuries throughout history and do not commonly harm commercial fishing interests.

Sharks and their close relatives, rays and skates, are classified in biological taxonomy within the class Chondrichthyes (fish) and the sub-class Elasmobranchii (fish without bones). Within the sub-class Elasmobranchii, sharks are classified in the sub-class Selachii, and rays and skates are classified within the sub-class Batoidei.

Of the more than 350 known species of shark, as many as 35 species have been recorded attacking humans. Repeated attacks, however, have been recorded with less than 15 of these species. The frequency of shark attacks worldwide is quite small compared to the number of humans who work and play in the ocean each day. Less than about 100 humans are attacked by sharks each year with fatalities from shark attack averaging around 30. Nevertheless, the real fact of shark attack and the constant possibility, though low probability, of shark attack makes the need for an effective shark repellent a pressing reality for millions of ocean-going people every day.

While fatal shark attacks have most likely occurred for millennia, recorded events have been rare until the twentieth century. One early recorded fatal shark attack occurred in 1580 when a man overboard on a Portuguese sailing vessel was reportedly "torn to pieces" while clinging to a life buoy. (Allen (2001) at 33). This was certainly not the earliest recorded shark attack. In fact, the danger of shark attacks on sponge divers in the Mediterranean was documented in the Natural History of Pliny the Elder in 77 A.D. and the above-noted fatal story of a sponge diver who lost part of his lower body to a shark was recorded in the third century B.C. (Allen (2001) at 35). Many shark attacks have been recorded ever since. There appears, however, to have been no consideration of methods of limiting shark attacks (at least in the United States) until 1916.

The summer of 1916 ushered in "the year of the shark" for the coastal regions around New York City. Over just 12 days in that summer, at least four people were killed by sharks along the New Jersey coastline. (Allen (2003) at 174). These attacks later inspired the movie Jaws (1975). (Thomas B. Allen, The Shark Almanac 174 (2003)). Beginning in 1916, the American public embraced a collective and long-enduring fear of sharks. This fear swelled to a point of concern for the U.S. government when it entered World War II against Japan in the South Pacific. (Allen (2001) at 207). To maintain morale among sailors and airmen (and their families) who faced the constant possibility of finding themselves adrift and exposed at sea, the U.S. government began research directed at protecting service personnel from shark attack. (Allen (2001) at 207). In this effort, the U.S. Navy began a program to develop a chemical shark repellent. The resulting product was known as "Shark Chaser."

In Chapter 17 of Dr. Perry W. Gilbert's 1975 printing of "Sharks and Survival", Richard L. Tuve of the U.S. Naval Research Laboratory describes the development of the U.S. Navy "Shark Chaser" chemical shark repellent. The program originated with the Office of Strategic Services in March 1942. Initial research was based on anecdotal evidence; Floridian fishermen contended that if a shark died on an unattended hook and line, further fishing in that area became undesirable. The researchers, therefore, hypothesized that some substance emitted by the decomposing body drove other sharks away from the vicinity.

As research continued, Woods Hole investigators and U.S. Navy scientists determined (erroneously it turns out) that the principal chemical material exuding from the decomposing shark was ammonium acetate. Scientists at Wood Hole also proposed the use of copper, which was known to reduce feeding in captive fishes and sharks. The ultimate combination of ammonium acetate and copper produced copper acetate, which was combined with nigrosine dye to provide a visual indication of the repellent dispersion.

The dye and copper acetate combination was molded into cakes and field testing began in 1944. Following a series of successful tests, a readjustment to 20% copper acetate and 80% nigrosine dye cake was sold as the "Shark Chaser." The military specifications for "Shark Chaser" were given under MIL-S-2785A as of Feb. 2, 1961.

As the Shark Chaser repellent found widespread use, continued research revealed that copper acetate was not effective in repelling sharks. In Chapter 2 of Bernard J. Zahuranec's 1983 printing of "Shark Repellents from the Sea: New Perspectives" the author gives insight into the inefficacy of the Shark Chaser. From tests in the shark pens at Bimini, Bahamas, Gilbert and Springer (1963) concluded that copper acetate fails to repel or inhibit the feeding activities of several species of sharks we have worked with at Bimini. Tester (1963) also reported the inefficacy of copper acetate against tiger sharks and other fish. Some theorized that the nigrosine dye itself was actually a visual deterrent. It was eventually concluded that copper acetate was not a practical deterrent for human use, and the military ultimately halted the issuance of the Shark Chaser. Recent research by the present inventors has confirmed these earlier findings that copper acetate is ineffective as a shark repellent and that ammonium acetate is not a principal component of decomposing shark tissue. See Tables 2 and 4 and FIG. 8.

While copper acetate was abandoned by the U.S. government in the 1960s, shark repellent research continued in the United States, with focus on marine organisms as sources of a repellent. Holothurins, anemones, urchins, and gorgonians were explored for a potential toxin but no shark repellent activity was detected. More research has been conducted on other naturally-occurring compounds. The inventors report that holotoxin from macerated sea apples, as well as seven types of potent hemolytic glycosides (saponins) from plants, were not effective as shark repellents.

Over the last 50 years antishark measures employed to protect humans from shark have included electrical repellent devices (Gilbert & Springer 1963, Gilbert & Gilbert 1973), acoustical playbacks (Myrberg et al. 1978, Klimley & Myrberg 1979), visual devices (Doak 1974) and chemical repellents (Tuve 1963, Clark 1974, Gruber & Zlotkin 1982). None of these procedures proved totally effective in preventing shark attacks. (Sisneros (2001)).

Following World War II, when reports of Shark Chaser's ineffectiveness began to appear, the Office of Naval Research began to reconsider the matter of chemical shark repellents and renewed the screening and testing of possible candidates (Zahuranec & Baldridge 1983). Hundreds of chemical substances were tested on sharks in an effort to find a chemical that would produce a quick and effective repellent response (Springer 1954, Gilbert & Springer 1963, Tester 1963). These chemicals included powerful toxins that could (and did) kill a shark after brief exposure; but none elicited the desired repellent response. Support for the research eventually ended after many attempts had provided no effective shark repellent. (Sisneros (2001)).

As described in the ReefQuest Centre for Shark Research:
In 1974, ichthyologist Eugenie Clark noticed that the delicate Moses Sole (*Pardachirus marmoratus*) was easy to catch and appeared to secrete a milky, astringent substance from the base of its dorsal and anal fin spines. Suspecting that the little fish was protected by a toxin of some kind, Clark collected several specimens for study. She found that the Moses Sole did indeed secrete a toxin she named "pardaxin," which caused red blood cells to rupture and—most intriguingly—repelled sharks. Tests by Clark in the laboratory and open sea revealed that at least four species of sharks were repelled by pardaxin for 10 hours or longer.

While fresh pardaxin repelled sharks, it presented serious stability problems because it was not stable for room temperature storage, and was heat-sensitive. Pardaxin could be freeze-dried, but this form was only 30% as effective as the fresh secretion, as reported by Zlotkin (1976). Chemical analysis yielded that pardaxin was an acid protein of 162 amino acids with a MW of 17,000 Daltons. The acid protein had a difficult synthesis pathway making commercial production not commercially practical. Sigma-Aldrich currently offers pardaxin for sale in the U.S. at $487.00 US for 1 milligram (product #P0435-1MG). Similar compounds such as mosesin and pavoninin present the same difficulties. There has been and remains a long-felt need for a shark repellent that can be produced and stored at room temperature with high yields of repellent. Further, it is believed that pardaxin, mosesin, and pavoninin act on the shark's respiratory system, requiring a minimum concentration of repellent to enter the mouth and contact the gill rakes of the shark, i.e., repellent had to be squirted directly into the shark's mouth.

Zlotkin noted that pardaxin possessed surfactant properties, reducing surface tension by as much as 60%. As described at the ReefQuest Centre for Shark Research:

> Zlotkin teamed with shark biologist Samuel Gruber to test a hunch: could commercially available soaps repel sharks? Zlotkin and Gruber tested two inexpensive commercial soap components, sodium and lithium lauryl sulfate (SLS and LLS, respectively—SLS, incidentally, is a common ingredient in shampoos), on young Lemon Sharks (*Negaprion brevirostris*). They found that both compounds were even more effective than pardaxin at repelling captive Lemon Sharks.

Further tests by Nelson et al. found that SLS was an effective repellent against blue sharks and even great white sharks. As described in "The Behavior and Sensory Biology of Elasmobranch Fishes: An Anthology in Memory of Donald Richard Nelson" (Tricas, T. C. & S. H. Gruber (ed.) (2001)), as well as "Surfactants as chemical shark repellents: past, present, and future" (J. A. Sisneros (2000))," the greatest limitation of SLS is that it is required to be squirted into the mouth of an approaching shark. It is not effective in surrounding-cloud-mode dispersions. Therefore, SLS is only useful when the user can clearly see an approaching shark and orchestrate the delivery of SLS into the animal's mouth. There has been a long-felt need for a repellent administered in surrounding cloud dispersions, thereby avoiding the impracticable need for direct-oral delivery.

In 2001, Sisneros reported further research on compounds related to pardaxin. Sisneros confirmed that dodecyl sulfate was the most effective surfactant shark repellent available at the time and that even the best repellent did not meet the Navy's potency requirement for a nondirectional surrounding-cloud type repellent of 100 parts per billion (0.1 ppm or 100 micrograms/Liter). Sisneros further concluded that dodecyl sulfate would only be practical as a directional repellent such as in a squirt application. Sisneros suggested that future research should test the action of alkyl sulfates on cell membranes, the potential of other biotoxic agents, and semiochemicals in the search for an effective chemical shark repellent. (Id.)

The existence of semiochemical repellents were first considered by Rasmussen & Schmidt in 1992. They suggested that sharks may be chemically aware of the presence of potential danger by sensing the bodily secretions from potential predators. Rasmussen & Schmidt hypothesized that lemon sharks, especially juveniles, inherently recognize chemical exudates produced by the American crocodile, *Crocodylus acutus*, a known predator of sharks. The concentrations needed to produce aversive responses in lemon sharks ranged from $10^{-7}$ to $10^{-9}$ M, which was near the functional limit of shark chemoreceptors (Hodgson & Mathewson 1978).

Sisneros also noted that another proposed potential source for shark repellent semiochemicals might perhaps be found in decomposing shark flesh (Baldridge 1990, Rasmussen & Schmidt 1992) because anecdotal information from fishermen claimed that sharks avoid areas containing decomposing carcasses of previously caught dead sharks. Sisneros postulated that perhaps there are semiochemicals found in extremely low concentrations in decaying shark flesh that act as alarm pheromones and provide warning signals to nearby sharks. None of those postulated compounds were known or have since been found and there have been no commercially available effective chemical shark repellents. As such, the long felt need for an effective repellent had not been satisfied until the present invention.

U.S. Pat. Nos. 4,490,360 and 4,340,587 describe the use of lucibufagins from fireflies and extractions of fireflies as a shark repellent. While the specifications suggest that behavioral changes were occurring in numerous species of animals, no effects were observed on larger inshore and pelagic sharks. Further, while one specification describes the "very extensive practical use in protecting bathing zones from the invasion of objectionable sea life such as sharks," the Atlantic Sharpnose species represents a very small-sized inshore species which has no reported aggressiveness nor represents a bycatch problem. Additionally, no practical synthesis is described for lucibufagins, therefore tremendous quantities of fireflies are required to produce drum-quantities of a repellent.

Data on the use of firefly-derived repellents were also reported against the Atlantic Sharpnosed Shark (*Rhizoprinodon terraenovae*), the smooth dogfish (*Mustelus canis*), the pinfish (*Lagadon rhomboides*), and killifish (*Fundulus heteroclitus*) in a paper presented at a symposium in 1981. (Bonaventura et al., Problems and Possibilities: The Development of an Effective Shark Repellent for Naturally Occurring Biologically Active Substances, Jan. 5, 1981, Annual Meeting of the American Association for the Advancement of Science, Toronto, Canada). These data additionally provide no support for a repellent of inshore and pelagic sharks that would be useful as an effective shark repellent.

U.S. Pat. No. 6,606,963 describes an acoustical system which produces shark-repelling waveforms. This invention affects the shark's hearing and lateral line sensory systems. However, as described by Klimley, Myrberg et al., sharks rapidly habituate to a sound source unless output power is very high. The present invention overcomes these limitations by, in theory, affecting the olfactory system. There has been a long-felt need for a repellent that is effective such that competitively feeding populations of sharks will stop feeding and will avoid all food stimuli in the presence of the repellent, wherein no habituation is observed after exposure.

Researchers have historically used several bio-assays to determine if a repellent evokes a flight response in shark. One such bio-assay introduces repellent of a certain concentration and volume to a position in a tank and measures avoidance in sharks of that portion of a tank or other aversive swimming behavior.

Another such bio-assay introduces repellent of a certain concentration and volume into the feeding zone of sharks and measures whether sharks flee the feeding zone and/or cease feeding behavior.

Another preliminary bio-assay measures the effect of a repellent on a shark that is immobilized in "tonic immobility." Tonic immobility is a state of paralysis that typically occurs when a shark is subject to inversion of its body along the longitudinal axis. This state is called "tonic," and the shark can remain in this state for up to 15 minutes thereby allowing researchers to observe effects of chemical repellents. After behavioral controls are established, an effective chemical repellent will awaken a shark from a tonic state. Researches can quantify dose sizes, concentrations, and time to awaken from these studies. A microliter autopipettor is used to observe effects at the 10-100 uL level. A 60 cc syringe is used as a baseline, looking for a preliminary response.

Another bioassay is known as the Johnson-Baldridge test. The test is defined as the delivery of 100 mg of chemical repellent into a 6 cubic meter boundary of water over a 3.5 hour period under steady-state conditions. This level of repellent delivery from a point source is considered to represent a concentration of 0.1 ppm. This is a proposed criterion in the art for an "effective" repellent. If sharks demonstrate aversive behavior under these conditions, then the criteria is satisfied. The inventors have designed and constructed an experiment to test if semiochemicals meet the Johnson-Baldridge criteria. A PVC tripod was situated in the ocean. The tripod supported a peristaltic metering pump, set to meter out exactly 100 mL of repellent per hour. The tripod also supported a video camera and transmitter, which observed the area under the tripod, marked off for 6 cubic meters and compensated for tidal changes. The video was monitored and recorded on shore. A fish head was secured under the tripod, within view of the camera. Once a population of sharks was established near the tripod, a control was performed. A second fish head was secured, the pump was started, and behavior was observed. If the fish head was protected for the 3.5 hour period, the criteria were met.

BRIEF SUMMARY OF THE INVENTION

Applicants have discovered an effective elasmobranch repellent. According to a non-limiting embodiment of the present invention, a repellent is provided comprising a semiochemical from a carcass of an elasmobranch. The inventive semiochemical terminated tonic immobility and evoked a flight response in an elasmobranch. It was also noticed that the inventive semiochemical did not evoke a flight response in fish having a bony skeleton. In another non-limiting embodiment of the present invention, the repellent comprises a semiochemical and a polar solvent. In another non-limiting embodiment of the present invention, the repellent comprises a carcass of an elasmobranch treated with a polar solvent for between about one month to about six months. In another non-limiting embodiment of the invention, the repellent is filtered from the polar solvent treated elasmobranch carcass. In another non-limiting embodiment of the present invention, the repellent comprises a mixture of semiochemicals from more than one carcass of more than one elasmobranch species.

According to a second embodiment of the present invention, a method of repelling an elasmobranch is provided comprising administering a semiochemical in the expected proximity of an elasmobranch. In another non-limiting embodiment of the present invention, the semiochemical is from an elasmobranch carcass treated with a polar solvent.

According to a third non-limiting embodiment of the present invention, a repellent is obtained by a process comprising the steps of exposing a carcass of an elasmobranch to a polar solvent, and filtering the repellent from the carcass. In another non-limiting embodiment of the present invention, the repellent is obtained by a process wherein an elasmobranch carcass is aerobically decayed prior to exposure to a polar solvent and a portion or the entirety of the pre-treated carcass is then exposed to a polar solvent. In a non-limiting preferred embodiment, the elasmobranch carcass is aerobically decayed to a degree of decomposition between the onset of rigor mortis and the completion of putrefaction prior to exposure to the polar solvent. In another non-limiting preferred embodiment, the pre-treated carcass is completely immersed in a polar solvent.

In a non-limiting embodiment of the present invention, the inventive repellent is characterized on an HPLC chromatogram with three characteristic peaks with relative peaks detected in the range between approximately 240 nm to approximately 340 nm at about 5, about 6 and about 7 minutes and the relative peak at about 7 minutes is greater than the relative peaks at about 5 minutes and about 6 minutes. In a preferred embodiment, the repellent HPLC chromatogram has the following characteristics

| Column: | Novapak 0.5u C18 reversed phase |
|---|---|
| Flow rate: | 0.5 ml/min |
| Mobile phase: | A: Methanol, 0.1% acetic acid |
| | B: Water, 0.1% acetic acid |
| Gradient: | 0-10 minutes 100% A |
| | 10-12 minutes, 0% A, 100% B, linear |
| | 12-20 minutes 100% B |
| | 20-22 minutes 0% B, 100% A, linear |
| | 22-60 minutes, 100% A |
| Injection: | 50 ul into a 50 ul loop |
| Column temperature: | 25° C. |

In a preferred non-limiting embodiment, the repellent has the following ultraviolet absorbances: 300 nm, greater than 1 AU; 312 nm, greater than 2 AU; and 322 nm, greater than 2 AU.

According to a fourth non-limiting embodiment of the present invention, a process for making an elasmobranch repellent is provided comprising the step of extracting a semiochemical from a carcass of an elasmobranch by exposing said carcass to a polar solvent and filtering said repellent from said carcass. In a preferred non-limiting embodiment, the method of manufacture of the inventive repellent comprises (1) placing a carcass of an elasmobranch in an extraction vessel, (2) exposing the carcass to aerobic decomposition, (3) treating said carcass and the decomposition fluids of said carcass with a polar solvent preferably in 50% water, 40% methanol, 6.5% ethanol, and 3.5% methyl isobutyl ketone, by weight, (4) monitoring for detectable semiochemicals, and (5) filtering the repellent from the carcass.

According to a fifth non-limiting embodiment of the present invention, a compound for repelling elasmobranch is provided wherein the compound is characterized by a uv-visible spectrum having an absorbance peak between about 280 nm and about 340 nm.

According to a sixth non-limiting embodiment of the present invention, a specially designed container is provided for administering an elasmobranch repellent comprising a pressurized container and an actuator for release of the repellent when activated. In a preferred non-limiting embodiment, the container is an aerosol container comprises an actuator that triggers a continuous release of repellent when activated. In another non-limiting preferred embodiment, the aerosol container is weighted in the vicinity of the actuator to provide an erratic motion in the water when the container is administered, the actuator is activated and the repellent is discharged from the container.

According to a seventh non-limiting embodiment of the present invention, a method of repelling an elasmobranch is provided comprising administering a semiochemical from a raft, buoy or piling in the expected vicinity of an elasmobranch. In a preferred non-limiting embodiment of the present invention, the semiochemical is administered from the raft, buoy or piling from a pressurized diptube that discharges the semiochemical above the surface of the water.

According to an eighth non-limiting embodiment of the invention, a method of repelling an elasmobranch is provided comprising attaching to a fishing longline a mass of carcass of an elasmobranch that has been treated with polar solvent.

According to a ninth non-limiting embodiment of the present invention, a kit is provided comprising a semiochemical repellent and a vehicle for administering the semiochemical repellent. Such vehicle of administration may include known devices and novel devices disclosed herein.

BRIEF DESCRIPTION OF THE DRAWINGS

The invention will now be described by way of example with reference to the accompanying drawings wherein:

FIG. 2 illustrates comparison of uv-visible spectra of eight exemplary semiochemicals in accordance with the present invention. The composite spectra represent eight exemplary repellents in accordance with the present invention wherein uv-visible spectral maxima reside in the region of around 280 nm to around 340 nm. A distinct signature peak is notable in each of these exemplary repellents at around 300 nm with a semiochemical of a Great White shark head having the highest relative detected absorbance at the signature 300 nm peak.

FIG. 3 illustrates HPLC chromatograms of the early-eluting components of semiochemicals GWH and A1 in accordance with the present invention. Notable are peaks at around 5, around 6 and around 7 minutes. The 7 minute peak is stronger than the others.

FIG. 4 illustrates HPLC chromatograms of late-eluting components of exemplary semiochemicals GWH and A1 in accordance with the present invention. Noted are peaks of the semiochemicals at around 31 minutes, around 34 minutes, around 36 minutes and around 42 minutes with a signature sharp peak in the range of about 30 to about 40 minutes followed by a broad, double-maxima peak about two minutes later.

FIG. 5 illustrates HPLC chromatograms of primary amines in exemplary semiochemicals GWH and A1 in accordance with the invention at 570 nm after treatment with ninhydrin. Noted are peaks indicative of primary amines. Further, the chromatograms contain peaks at around 5, around 6 and around 7 minutes with the 7-minute peak much stronger than the 5-minute and 6-minute peaks.

FIG. 6 illustrates HPLC chromatograms of secondary amines in exemplary semiochemicals GWH and A1 in accordance with the invention at 440 nm after treatment with ninhydrin. Peaks detected at 440 nm are indicative of secondary amines. Further, the chromatograms contain a first strong and sharp peak around 34 minutes and a strong broad peak with two components eluting about 2 minutes later.

FIG. 7 illustrates a GC-MS spectrograph of an exemplary semiochemical GWH in accordance with the present invention on Hewlett Packard model 6890 GC with 5973 MSD having a column of DB-5 40 m×0.18 mm×0.40 mm film, a carrier of helium at 1 mL/min; an injection of 1 microliters, splitless at 280° C.; heated to 40° C. and held for 5 minutes then to 300° C. at 10° C./min and held for 5 minutes; with the transfer line heated to 300° C.; and an MSD scan at 20-700 m/z. The mass spectral data in combination with the chromatogram was analyzed using quality of NIST 98.1 library match.

FIG. 8 illustrates a uv-vis absorbance spectrum of an exemplary semiochemical CP in accordance with the present invention. Noted are peaks at around 440 nm and around 570 nm.

FIG. 9 illustrates a uv-vis absorbance spectrum of 50% w/w ammonium acetate (a proposed and discredited shark repellent) in water, derivatized with 0.1 g ninhydrin at 40° C. for 15 minutes. Noted are no maxima at around 440 nm or around 570 nm.

FIG. 10 illustrates a GC-MS chromatogram of an exemplary semiochemical CP in accordance with the invention on Hewlett Packard model 6890 GC with 5973 MSD having a column of DB-5 40 m×0.18 mm×0.40 mm film, a carrier of helium at 1 mL/min; an injection of 1 microliters, splitless at 280° C.; heated to 40° C. and held for 5 minutes then to 300° C. at 10° C./min and held for 5 minutes; with the transfer line heated to 300° C.; and an MSD scan at 20-700 m/z. The mass spectral data in combination with the chromatogram was analyzed using quality of NIST 98.1 library match.

FIG. 11 illustrates a comparison of uv-vis spectra of one-year-old semiochemicals A2, A13N and SQ1. The uv-visible spectra of each semiochemical was taken using a Perkin Elmer Lambda 12 dual-beam scanning spectrophotometer, neat semiochemical solution was micron filtered and loaded into quartz cuvettes, representative uncontaminated solvents used in the extraction process (at the same ratios used to perform the extractions) were used as a reference sample or "blank," and a peak at around 300 nm is seen for each semiochemical in accordance with the invention.

FIG. 12 illustrates a comparison of uv-visible spectra of semiochemical CL at 0, 7, 21 and 40 days during the extraction process. A 300 nm peak is shown to increase in absorbance over time.

FIGS. 13-15 illustrate HPLC chromatograms of exemplary semiochemical A2 in accordance with the invention derivatized with ninhydrin using a variety of solvents and injection volumes.

FIG. 16 illustrates an FTIR spectrum of exemplary semiochemical A2 in accordance with the invention. The resulting proposed stretches corresponding to the spectral peaks are provided in Example 4G, below.

FIG. 17 illustrates a Head Space Total Ion GC-MS chromatograph of an exemplary semiochemical A2 in accordance with the present invention.

FIG. 18 illustrates a Direct Injection GC-MS Total Ion chromatograph of an exemplary semiochemical A2 in accordance with the present invention.

FIG. 19 illustrates a total ion LC-MS chromatograph of exemplary semiochemical A2 in accordance with the present invention. Mass to charge ratios are noted in the chromatogram.

FIG. 20 illustrates a GC-MS chromatograph of exemplary semiochemical CF-Composite in accordance with the present invention on Hewlett Packard model 6890 GC with 5973 MSD having a column of DB-5 40 m×0.18 mm×0.40 mm film, a carrier of helium at 1 mL/min; an injection of 1 microliters, splitless at 280° C.; heated to 40° C. and held for 5 minutes then to 300° C. at 10° C./min and held for 5 minutes; with the transfer line heated to 300° C.; and an MSD scan at 20-700 m/z. The mass spectral data in combination with the chromatogram was analyzed using quality of NIST 98.1 library match.

FIG. 21 illustrates a GC-MS chromatograph of an exemplary semiochemical B-Composite in accordance with the present invention on Hewlett Packard model 6890 GC with 5973 MSD having a column of DB-5 40 m×0.18 mm×0.40 mm film, a carrier of helium at 1 mL/min; an injection of 1 microliters, splitless at 280° C.; heated to 40° C. and held for 5 minutes then to 300° C. at 10° C./min and held for 5 minutes; with the transfer line heated to 300° C.; and an MSD scan at 20-700 m/z. The mass spectral data in combination with the chromatogram was analyzed using quality of NIST 98.1 library match.

FIG. 22 illustrates HPLC chromatographs of early-eluting components of one-and-a-half-year-old degraded semiochemical A2 and more-than-one-year-old degraded semiochemical N2. Noted is the absence of a strong peak at around 7 minutes.

FIG. 23 illustrates HPLC chromatographs of late-eluting components of one-and-a-half-year-old degraded semiochemical A2 and more-than-one-year-old degraded semiochemical N2. Noted are one sharp peak and one sharp double peak at about 3 and about 2 minutes before a weak, broad double-peak at around 35 minutes.

FIG. 24 illustrates prior known solution delivery devices modified to contain semiochemical repellent in accordance with the present invention. FIG. 24A illustrates a pressurized delivery pole apparatus. FIG. 24B illustrates a delivery device syringe. FIG. 24C illustrates a cattle-treatment "drench" gun.

FIG. 25 illustrates a novel exemplary semiochemical delivery device in accordance with the present invention. FIG. 25A illustrates an aerosol canister for administration of semiochemical repellent to a shark environment. FIG. 25B illustrates the various axes of rotation of the exemplary canister. FIG. 25C illustrates directional discharge of repellent by the novel exemplary device in all directions yet having a preference for discharge in the water due to continuous discharge of repellent and being weighted in the vicinity of the actuator. It is noted that repellent is discharged in the water and into the air above the water, creating a concentration of repellent in the immediate vicinity of the container and creating a wider dispersion of repellent as it settles out of the air onto the surface of the water.

FIG. 33 illustrates a repellent delivery device adapted to a surfboard in accordance with the present invention.

Figure 1A:
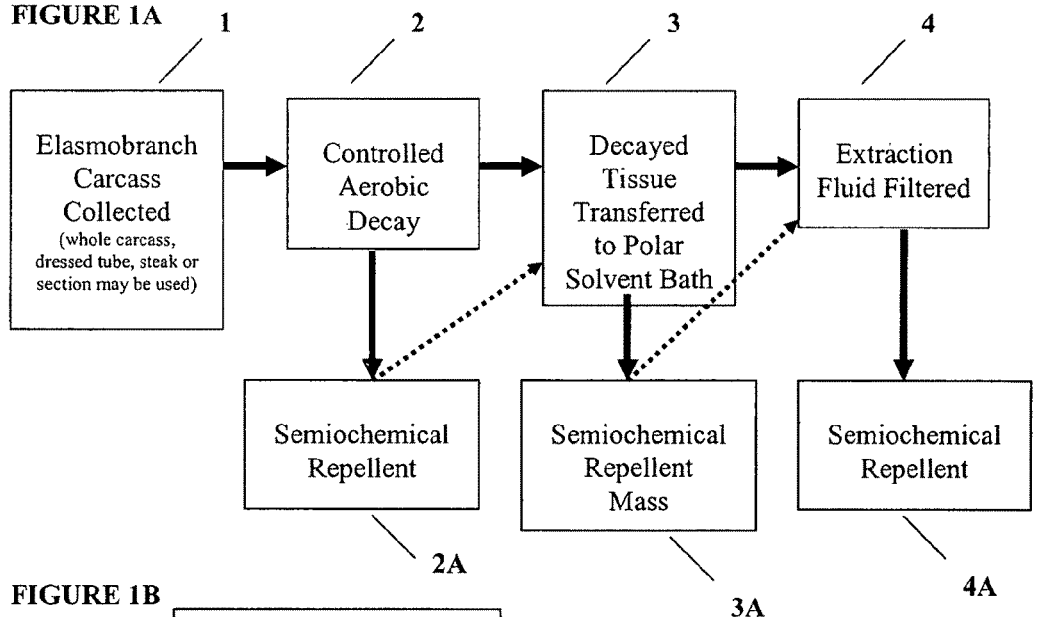
FIGS. 1A and 1B illustrate process flow charts for extraction of semiochemical repellents in accordance with the present invention.

The novel features, which are believed to be characteristic of the present invention, will be further understood from the following discussion.

DETAILED DESCRIPTION OF THE INVENTION

"Acoustical stimulation" is the arousal or activation of a subject related to sound or sense of hearing. Elasmobranchs are attracted to low-frequency pulsed sounds, similar to those emitted by wounded prey. Acoustical stimulation of a subject is generally accomplished by the pulsing of sound waves in the frequency of 25 to 100 Hz. Some elasmobranchs are attracted to sound sources from distances as great as 250 m.

"Canister" is a large or small container or vessel of any shape. An "aerosol canister" is a large or small container or vessel of any shape the contents of which are held under pressure and may contain a propellant gas or material to discharge a desired substance in a spray, liquid, foam or mist.

"Carcass" is the dead body of an animal or any portion thereof. For use in this application and unless otherwise indicated, a carcass refers to the dead body of an elasmobranch whole or in part and cleaned or uncleaned of stomach contents. Carcass may include the head, tail and/or muscle tissue.

"Complete putrefaction" is the degree of decomposition where muscular tissue has substantially liquefied. Typically, the muscular tissue falls away, as a slime, from the skin, not retaining any shape. This period roughly coincides with the "black putrefaction" or "butyric putrefaction" periods of mammalian decay, approximately 20-50 days after death.

"Conspecific" means of the same species.

"Conspecific repellents" are repellents that are made from a species of elasmobranch that repels the same species or family or order of elasmobranch.

"Elasmobranchii" represents the subclass of class Chondrichthyes (cartilaginous fish), which includes the sharks and rays. In this specification, "elasmobranchs" represent the super-orders and orders of elasmobranchs that are of interest for producing a repellent based on availability and conservation, and also those that present a potential threat to humans or represent a bycatch problem in commercial fisheries. As such, "elasmobranchs" in this specification means one or more elasmobranchii in the super-orders Galeomorphii and Squalomorphii and orders Squaliforms (dogfish), Carcharhiniformes (requiem sharks), Lamniformes (mackerel sharks), and Orectolobiformes (carpet sharks).

"Feeding zone" is the area in which sharks have been stimulated and demonstrate aggressive feeding behavior.

"Heterospecific" means from a different species.

"Heterospecific repellents" are repellents that are from a species of elasmobranchs that repels a different species or family or order of elasmobranch.

"Polar solvent" is a first substance capable of dissolving another substance wherein the first substance comprises molecules with electric charges unequally distributed, leaving one end of each molecule more positive than the other.

"Putrefaction" is the degree of decomposition at which most of a carcass is decomposed.

"Rigor mortis" is the degree of decomposition at which a carcass becomes stiff.

"Semiochemical" is a compound or mixture of compounds derived from the carcass of an elasmobranch that can terminate tonic immobility of an elasmobranch with a dosage of less than 500 microliters, that can evoke a flight reaction in an elasmobranch that has been stimulated to feed and that does not evoke a flight response in telios fish.

"Tonic immobility" is the state of paralysis that typically occurs when an elasmobranch is subject to inversion of its body along the longitudinal axis of the body, i.e., is belly up. The elasmobranch can remain in this state for up to 15 minutes.

I. SEMIOCHEMICAL EXTRACTION PROCESS

Semiochemical repellents in accordance with the present invention are prepared from an elasmobranch carcass as illustrated in FIG. 1A. An elasmobranch carcass is collected (whole or in part). The carcass or carcasses are aerobically decayed preferably beyond the degree of decomposition of rigor mortis but before complete putrefaction. Some semiochemical compounds are eluted during the controlled aerobic decay.

The elasmobranch carcass can be of a single variety or of multiple varieties of elasmobranch and may represent whole carcasses or a part or parts of different carcasses. The carcass sample preferably contains at least a portion of muscle tissue. A whole carcass, dressed tube of carcass, steak of carcass or section or sections of carcass may be used, cleaned or uncleaned of entrails or stomach contents.

The carcass sample is allowed to aerobically decay beyond rigor mortis but before putrefaction, which period of time may be from about one day to about one month. The aerobically decayed tissue is transferred to a bath of polar solvent, preferably along with any semiochemicals that may have been released. The decayed tissue is kept in a bath of polar solvent in an extraction vessel for from about 1 week to about 6 months and up to about one year. The polar-solvent-carcass vessel contents are sampled from time to time to determine the stage of extraction of semiochemical(s). When the presence of semiochemicals is detectable at a determined end-point, the contents of the extraction tank may be filtered for use as an elasmobranch repellent or the pre-filtered contents may be formed into a mass for use as an elasmobranch repellent.

Figure 1B:
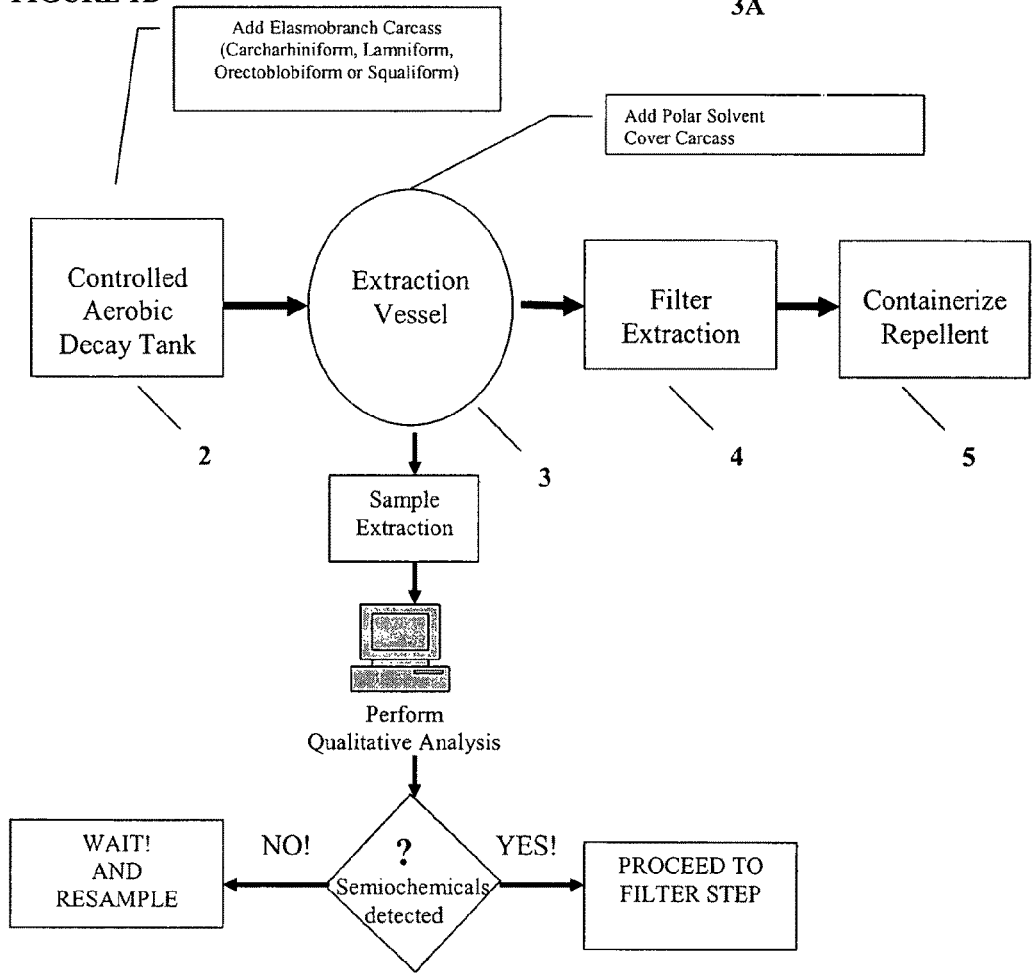

A preferred extraction process is described in FIGS. 1A-1B. For example, muscular tissue from one or more sharks of the Order of Carcharihiniform, Orectobolobiform, Lamniform or Squaliform are obtained and allowed to aerobically decay in an environment free from insects and other flesh eating organisms (1). In a preferred embodiment, the shark tissue is aerobically decayed in an extraction vessel of polypropylene, high density polyethylene (HDPE) or glass for about ten days (2). Polar solvent is then introduced to the extraction vessel of sufficient volume to cover the decayed shark tissue (3). After an amount of time, preferably one month, the extraction is sampled for instrumental analysis to determine whether or not semiochemicals have begun to be produced.

If semiochemical production is not yet sufficient to achieve a desired end-point (as set forth in this specification by standard signatures on analytical instruments or by a demonstration by testing the repellent activity against a shark), the extraction process is allowed to proceed for another period of time. The following period of time for further incubation of the extraction may be any amount of time, ordinarily less than about six months. Preferably, the waiting period is from about 1 day to about one month, depending on the expected production time for semiochemicals from the particular shark tissue in the particular polar solvent. The skilled artisan will easily determine optimal waiting periods between instrumental analyses of the extraction. The waiting period and instrumental analysis should be repeated until there has been sufficient production of semiochemicals to achieve a desired end-point. The desired end-point is chosen by detection of sufficient semiochemicals using instrumental analysis or by the demonstration of a flight reaction in shark when applied to the shark's environment. Semiochemical repellent may be recovered at various stages (2A, 3A, 4A) in the process.

When the extraction process has produced sufficient semiochemicals to achieve a desired end-point, the contents of the extraction vessel is preferably filtered (4). The filtrate is containerized and prepared for administration as an elasmobranch repellent (5). The methods of the present invention are able to produce more than 15 liters of repellent solution from a 2.2 kg shark specimen. A 6-foot carcass is able to produce approximately 50 gallons of repellent solution according to the extraction process described in the present invention.

When semiochemicals in sufficient abundance are detected, the decay process may likewise be halted by lowering temperature or immersion in solvents for preservation until use. In an alternative, once semiochemicals in sufficient abundance are detected the contents of the extraction vessel is formed into a mass or masses for administration as an elasmobranch repellent.

In the extraction process, whole carcasses are preferable over sectioned carcasses. In lieu of an entire carcass, successful semiochemical repellents have been prepared using the entire head, the entire tail, or the liver from a specimen. Blood alone is not preferred for semiochemical derivation At the outset, carcasses should be allowed to decay aerobically, past the stage of rigor mortis, but before complete putrefaction. This may be accomplished by leaving the carcass in open air or a cooler for a period of time, taking care to not allow insects and scavengers to manifest. Decomposition fluids are preferably retained. A freshly killed carcass is unsuitable for deriving semiochemicals because specific catabolites have not yet been produced. A fully decayed carcass is unsuitable for deriving semiochemicals because specific catabolites are fully depleted or metabolized. Anaerobic decay is an unacceptable method, and produces high yields of organic sulfur compounds and low yields of semiochemicals.

Carcass selection may be made based on what species of elasmobranch are desired to be repelled. For example, it is not preferred to utilize stingray carcasses when trying to develop a hammerhead-specific repellent. It is preferred, however, to use a stingray carcass to develop a stingray repellent. Most genus *Carcarhinus* specimens are very suitable for preparing broad-spectrum shark repellents. It is demonstrated herein that lemon shark carcasses not only produced semiochemical solutions which repelled lemon sharks, but also repelled blacknose, reef, and bull sharks.

Carcasses from multiple species are also suitable. For example, a vessel containing two lemon shark carcasses, one nurse shark carcass, and one smooth dogfish carcass produced a high yield of semiochemicals after 6 months of extraction time.

After the initial decay period and before total putrefaction, the decomposition fluids, blood, and the carcass mass are preferably placed in an extraction vessel. In a preferred embodiment, the carcass is not cleaned, gutted, or rinsed prior to transfer.

The extraction vessel is preferably a container which is impervious to organic solvents and acids, and which seals air-tight to prevent escape of solvent vapors. The vessel is ideally polypropylene plastic or glass. This vessel should possess access points for solvent addition, draining, circulation/stirring, and viewing.

The optimal positioning of the carcass in the vessel and solvent is with the carcass positioned vertically, head down, in the vessel. More than one carcass may be positioned in the vessel to increase yield.

A solvent for the extraction process is any polar solvent that is less than 100% water. A preferred extraction solvent is a water:solvent mixture at a 50:50 mix ratio by weight of water to another polar solvent. The skilled extraction chemist will understand that adjustments may be made to improve yields. A preferred water to other polar solvent ratio is 50:50 water:solvent, by weight.

Any single, binary, ternary, or multiple solvent system is suitable for the 50:50 mixture. For example, n-propanol, iso-propanol, glycol ethers, methanol/ethanol systems, acetic acid, hydrochloric acid solutions, butanol, dimethylsulfoxide, and short-chain aldehydes and ketones are acceptable solvents. A preferred polar solvent is 80% methanol, 17% ethanol, and 3% methyl isobutyl ketone by weight. Water in combination with the aforementioned solvents is also suitable, as long as anaerobic decay is minimized. Leaving the carcass in pure water is not a preferred solvent system. It is preferred that the solvent cover the entire carcass mass.

The extraction process should be carried out at about room temperature. Elevated temperatures speed the extraction process, but produce lower-efficacy semiochemical solutions. Soxhlet extraction similarly produces low-efficacy semiochemical solutions. The most effective process is simply to leave the vessel at room temperature and slow circulation for 3 to 6 months, depending on the solvent strength.

The solvent should be sampled periodically to monitor the presence of semiochemicals and to determine a desired end-point for the extraction process. End-point may be determined with uv-visible spectrophotometry, high performance liquid chromatography (HPLC), mass-spectrometry, infrared detection, visible detection of a yellow color or testing of samples on shark to determine if a flight reaction is induced.

Spectrophotometry is a simple method for determining the "ripening" state of the solvent mixture. Over time, peak absorbances will be observed between about 290 nm and about 320 nm, with some maxima being extremely strong when the extraction process is operating efficiently. When clear solvents are employed, the solvent/semiochemical mixture develops a characteristic pale-yellow coloration after 3 months, indicating the presence of the semiochemicals.

Preferred end-points for the extraction process as detected by different instrumental analyses are set forth in the following section.

At the end of the extraction process, the semiochemical solution may be filtered, but not distilled. Rotary evaporation and fractional distillation has been observed to ruin the efficacy of the semiochemical solution. Fritted glass filters and micron filters are very suitable for removing skin and biomass particles, as well as improving visual clarity. Vacuum may be employed in the filtration process, but heat is not preferred. Preferably, the solution is used at full strength for maximum repellency on wild sharks and rays.

A. Instrumental Analysis for Determining Desired End-Point of Extraction Process The end point of the extraction process may be determined by instrumental analysis. End-point is reached when a semiochemical has been produced in the extraction process to a point where it is detectable in sufficient amounts by instrumental analysis or where the extraction has developed to the point of evoking a flight response, evoking aversive swimming behavior, evoking termination of tonic immobility, or providing protection sufficient to satisfy the Johnson-Baldridge test in elasmobranchs. Liquid chromatography, spectrophotometry, gas chromatography and qualitative analytical techniques are preferably used to identify the point in time where semiochemical concentration reaches a maximum. Semiochemicals possess characteristic absorbance maxima, fragmentation, retention times, and physical properties, such as odor, color and pH.

A desirable end-point may be determined by testing a filtered sample from the extraction vessel on HPLC according the following gradient elution configuration:

| Column: | Novapak 0.5u C18 reversed phase |
|---|---|
| Flow rate: | 0.5 ml/min |
| Mobile phase: | A: Methanol, 0.1% acetic acid |
| | B: Water, 0.1% acetic acid |
| Gradient: | 0-10 minutes 100% A |
| | 10-12 minutes, 0% A, 100% B, linear |
| | 12-20 minutes 100% B |
| | 20-22 minutes 0% B, 100% A, linear |
| | 22-60 minutes, 100% A |
| Injection: | 50 ul into a 50 ul loop |
| Detection: | 240 nm, range 1 AUFS |
| Column temperature: | 25° C. |

In this setup, 6 characteristic compounds elute within the first 8 minutes, producing 6 peaks. Of these characteristic peaks, 3 are of particular interest. A distinctive strong peak at about 7 minutes and two moderate peaks at about 5 and about 6 minutes demonstrate well developed semiochemical extract. A second group of compounds elute after 23 minutes, indicating up to 25 additional compounds, with weak to moderate absorbances.

A desirable end-point may also be determined by testing a filtered sample of the extraction on HPLC after amines in the semiochemical repellent samples have been derivatized using ninhydrin to produce strong chromophores. Derivatization with ninhydrin yields two colored products, Rhuemann's purple at 570 nm for primary amines, and a colored product with an absorbance maximum at 440 nm for secondary amines. These colored products are detected using an HPLC and an ultraviolet-visible detector. Derivatization may be performed pre- or post-column, but post-column work must employ additional pumps, flow combiners, and elevated temperatures ahead of the detector. Preferably the derivatization is performed pre-column. Samples are prepared by combining 50% w/w of a 1% ninhydrin in 2-propanol solution with 50% w/w of a semiochemical sample. Samples are allowed to derivatize for 2 hours at 40° C. prior to analysis. The following system configuration is used:

| Column: | C18, reversed phase |
|---|---|
| Flow rate: | 1 ml/min |
| Mobile phase: | 80% water, 20% acetonitrile |
| Injection: | 10 uL |
| Detection: | 570 nm for primary amines, |
| | 440 nm for secondary amines |
| Column temperature: | 35° C. |

This method produces up to 5 characteristic peaks between 1 and 2 minutes for primary amines at 570 nm. The method also produces up to 5 characteristic peaks between 1 and 2 minutes for secondary amines at 440 nm. An entity at both detection wavelengths is observed at 4.8 minutes with a trace concentration. If, in an alternative method of HPLC analysis, the gradient elution configuration set forth above is employed at 570 nm, three characteristic peaks of particular interest elute at around 5, around 6 and around 7 minutes, with the strongest peak at 7 minutes. If the same gradient elution method is employed at 440 nm, a characteristic broad double peak is expected to elute at around 30 to around 40 minutes preceded by about two minute by an earlier sharp peak.

End-point may also be determined using uv spectral analysis. The ultraviolet spectra of an extracted semiochemical repellent solution may be considered to contain sufficient semiochemical products when they yield the following generally characteristic absorbances:

240 nm, greater than 2 AU
266 nm, greater than 1 AU
273 nm, greater than 1 AU
280 nm, greater than 1.5 AU
289 nm, greater than 1.5 AU
294 nm, greater than 2 AU
300 nm, greater than 2.5 AU
312 nm, greater than 3 AU
322 nm, greater than 3 AU.

The visible spectrum of a semiochemical repellent solution yields a weak but likewise characteristic absorbance maximum in the red region, at 657 nm (less than 0.5 AU). A salient peak to determine sufficient development of semiochemicals using uv-visible spectrophotometry is often a signature peak beginning around 300 nm and reaching a maximum near 310 or 320 nm.

For example, semiochemical CL (from *C. limbatus*) was sampled at 0, 7, 21 and 40 days to determine development of semiochemical uv-vis signature. (See FIG. 11.) Signature absorbance at around 300 nm increased as extraction proceeded. A 300 nm shoulder was barely perceptible at 0 days but increased throughout 7, 21 and 40 days of the extraction process to become a distinct peak at 40 days around 3.5 AU.

B. Instrumental Analysis of Semiochemicals—Composition of Matter

Semiochemical extractions may be qualitatively tested for the presence of sufficient semiochemicals to act as an elasmobranch repellent using a range of instrumental analytical techniques. These qualitative techniques include HPLC, uv-visible spectroscopy, infrared spectroscopy and mass spectrometry coupled with other separation techniques.

1. UV-Visible Spectrophotometry

To test an extraction for sufficient presence or development of semiochemicals using uv-visible spectrophotometric analysis a uv-visible spectrophotometer may be employed. A dual-beam scanning spectrophotometer, such as the Perkin Elmer Lambda 12 model, is preferable. Neat semiochemical solutions should be micron-filtered and loaded into quartz cuvettes. Representative uncontaminated solvents used in the extraction process, at the same ratios used to perform the extraction, are used as a reference sample or "blank."

An extracted semiochemical repellent solution may be considered to contain sufficient semiochemical products when its ultraviolet spectrum yields the following generally characteristic absorbances:

240 nm, greater than 2 AU
266 nm, greater than 1 AU
273 nm, greater than 1 AU
280 nm, greater than 1.5 AU
289 nm, greater than 1.5 AU
294 nm, greater than 2 AU
300 nm, greater than 2.5 AU
312 nm, greater than 3 AU
322 nm, greater than 3 AU.

The visible spectra of a semiochemical repellent solution yields a weak but characteristic absorbance maxima in the red region, at 657 nm, less than 0.5 AU.

2. Fourier-Transform Infrared Spectrophotometry

Fourier-Transform Infrared Spectrophotometry provides confirmation of certain functional groups in a semiochemical solution. Since the extraction solution contains water, another extraction must be performed to remove the semiochemicals from the water. FTIR cannot be accomplished in the presence of water. A simple extraction using a separatory funnel, with a 50:50 weight ratio mixture of a water-insoluble solvent to the semiochemical solution is very adequate. Strong water-insoluble solvents include diethyl ether, methylene chloride, and chloroform. The water-insoluble phase of this extraction may be further dried using magnesium or sodium sulfate, to remove all traces of water.

In an FTIR analysis, a waterless sample from the water-insoluble phase described above is set on a KBr crystal. A scan from 1100 nm to 3500 nm of a semiochemical extraction may indicate the following groups:

| | |
|---|---|
| 2800-3000 nm | Asymmetric and symmetric CH3 groups |
| 1300-1400 nm | Scissor, asymmetric, and symmetric CH3 groups |
| 1126.00 nm | C—O bond stretching |
| 1434.56 nm | C—O bond stretching |
| 1637.28 nm | C=C bond stretching |
| 2846.60 nm | C—H bond stretching |
| 2916.50 nm | C—H bond stretching |
| 2951.46 nm | C—H bond stretching |
| 3321.94 nm | OH bond stretching, indicating alcohols along with the above three preceding stretches. |

(FIG. 16.)

3. High Pressure Liquid Chromatography, HPLC

High Pressure Liquid Chromatography, HPLC is also used to detect the presence of semiochemicals in the extraction solution. A gradient HPLC system shows the presence of semiochemicals in two groupings, according to the following method:

| | |
|---|---|
| Column: | Novapak 0.5u C18 reversed phase |
| Flow rate: | 0.5 ml/min |
| Mobile phase: | A: Methanol, 0.1% acetic acid |
| | B: Water, 0.1% acetic acid |
| Gradient: | 0-10 minutes 100% A |
| | 10-12 minutes, 0% A, 100% B, linear |
| | 12-20 minutes 100% B |
| | 20-22 minutes 0% B, 100% A, linear |
| | 22-60 minutes, 100% A |
| Injection: | 50 ul into a 50 ul loop |
| Detection: | 240 nm, range 1 AUFS |
| Column temperature: | 25° C. |

In this setup, three particularly distinctive peaks may be observed within the first about 8 minutes with the peaks spaced about one minute apart. The strongest peak is generally the final peak of the three. Most often peaks elute at about 5 minutes, about 6 minutes and about 7 minutes with the peak at 7 minutes relatively stronger than the peaks at 5 and 6 minutes. A second group of compounds elute after 23 minutes, indicating up to 25 additional compounds, with weak to moderate absorbances.

In another analysis, components with absorbances at 622 and 624 nm elute at approximately 1.21 minutes using the following configuration:

| | |
|---|---|
| Column: | 0.5u C18 reversed phase |
| Flow rate: | 1 ml/min |
| Mobile phase: | 80% w/w water, 20% w/w acetonitrile |
| Injection: | 50ul into a 50ul loop |
| Detection: | 622-625 nm |
| Column temperature: | 35° C. |

HPLC coupled to fluorescence is also used to detect amino acids in the semiochemical mixture. Amino acids were derivatized with an active ortho-pthalaldehyde (OPA) reagent, which is prepared by treating OPA with an excess of a thiol compound, namely 2-mercaptoethanol, to form an OPA-2-mercaptoethanol adduct. This adduct reacts with primary amines to form fluorescent isoindoles, which are readily detected by a fluorescence detector post-column.

HPLC resolution can be improved by deproteinization. Membrane-filtered semiochemical samples are treated with perchloric acid, and then neutralized with potassium hydroxide, producing insoluble potassium perchlorate. The neutralized sample is centrifuged for 15 minutes, and the supernatant is analyzed by HPLC. Deproteinized samples generally produce better peak resolution and symmetry.

4. Ninhydrin Derivatization

The amine functions in semiochemical repellent samples can be derivatized using ninhydrin to produce strong chromophores. Ninhydrin is a selective oxidizing agent which causes oxidative decarboxylation of amino acids producing $CO_2$, $NH_3$, and an aldehyde with one less carbon atom than the parent amino acid. The reduced ninhydrin then reacts with the liberated ammonia to form Ruhemann's Purple, a complex which maximally absorbs light at 570 nm. Secondary amines, e.g., Proline and 4-Hydroxyproline, react via a different path and form a yellow derivative with an optimal absorbance at 440 nm.

Since the reaction with amines is highly specific and the absorption characteristics of the formed chromophores follow Beer's Law, reagents based on Ninhydrin have long been the most popular choice for detection and quantitation of amines and amino acids.

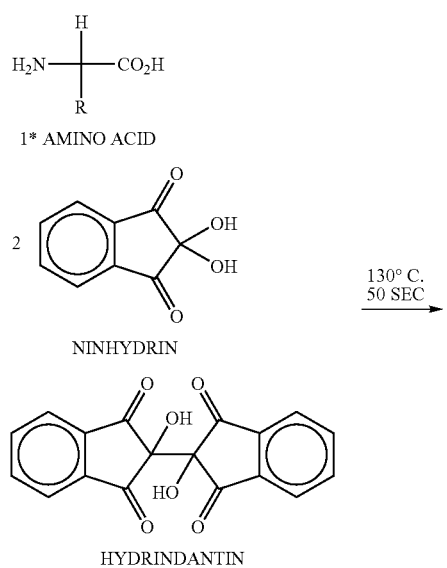

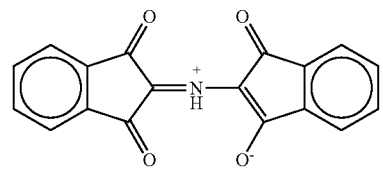

RUHEMANN'S PURPLE

Ninhydrin reacts slowly at room temperature. Consequently, in automated amino acid analysis, elevated temperatures of up to 130° C. are employed to reduce the conversion time to about one minute.

Ninhydrin derivatization often yields two absorbances in a semiochemical shark repellent, one at 570 nm and one at 440 nm, corresponding to primary and secondary amine functions respectively. For example, the absorbance spectra of a semiochemical extraction from the head of C. perezii (using 50% water, 40% methanol, 6.5% ethanol, and 3.5% methyl isobutyl ketone) derivatized with 0.1 g ninhydrin at 40° C. for 15 minutes is found in FIG. 8. Clear maxima are observable at 440 nm (around 4 AU) and 570 nm (2.9 AU). When primary and secondary amines are not present, and the sample is derivatized with ninhydrin, absorbances at 440 nm and 570 nm are not observed. A uv-visible spectrum of 50% w/w ammonium acetate (a discredited shark repellent) in water, derivatized with 0.1 g ninhydrin at 40° C. for 15 minute showed no maxima at 440 or 570 nm. (See FIGS. 8 and 9.)

Products absorbing at 440 nm and 570 nm may additionally be resolved and detected using an HPLC and an ultraviolet-visible detector as described for end-point determination above. When ninhydrin-derivatized semiochemical extracts are run on HPLC with the following parameters a distinctive chromatograph is produced:

| | |
|---|---|
| Column: | Novapak 0.5u C18 reversed phase |
| Flow rate: | 0.5 ml/min |
| Mobile phase: | A: Methanol, 0.1% acetic acid |
| | B: Water, 0.1% acetic acid |
| Gradient: | 0-10 minutes 100% A |
| | 10-12 minutes, 0% A, 100% B, linear |
| | 12-20 minutes 100% B |
| | 20-22 minutes 0% B, 100% A, linear |
| | 22-60 minutes, 100% A |
| Injection: | 50 ul into a 50 ul loop |
| Detection: | 240 nm, range 1 AUFS |
| Column temperature: | 25° C. |

For primary amines, three distinct 570 nm absorbing peaks elute at about 5, about 6 and about 7 minutes. (See FIG. 5.) For secondary amines, a distinctive pattern of 440 nm absorbing peaks elute. A sharp peak in the middle to later thirty minute range elutes followed about two minutes later by a broad double peaked elution. (See FIG. 6.)

5. Thin-Layer Chromatography

Flash chromatography and thin-layer chromatography may be performed, in order to observe amine components in ninhydrin derivatized samples. Using the following system, the primary and secondary amines can be well separated via flash chromatography:

| | |
|---|---|
| Stationary phase: | Silica gel, 230-400 mesh |
| Mobile phase: | 66% n-butanol, 33% methyl formate, 1% glacial acetic acid |
| Column height: | 6"-30", packed height, or 8" × 8" plates |
| Sample: | 0.2 micron-filtered, derivatized with 1% ninhydrin in 2-propanol. |

In thin-layer chromatography, the underivatized sample is spotted. After the endpoint is reached, the plate is developed with either 1% ninhydrin in 2-propanol solution, or the OPA-2-mercaptoethanol solution described earlier. The mobile phase should be optimized for optimal retention factors (Rf's).

II. CONSPECIFIC AND HETEROSPECIFIC EFFECTIVE ELASMOBRANCH REPELLENT

The biological activity of elasmobranch-repelling semiochemicals extracted from various orders of elasmobranchs, particularly, Orders Orectolobiformes, Lamniformes, Carcharhiniformes and Squaliformes, has been demonstrated in elasmobranchs of the Order Carcharhiniformes and Order Lamniformes. Repellent activity has also been observed in conspecific species interactions and heterospecific species interactions. ((See Table 1)).

Semiochemical extractions produced from pelagic Lamniforms have demonstrated repellency on inshore Carcharhiniformes (e.g., ML1, ML2, B, GWH). Semiochemical extractions produced from inshore Carcharhiniformes have demonstrated repellency on highly migratory (pelagic) Carcharhiniformes (e.g., GCC). Semiochemical extractions produced from a Squaliform have demonstrated repellency on Carcharhiniformes (e.g., SQ1). Semiochemical extractions produced from one or more species of Carcharhiniformes have demonstrated repellency on entirely different species of Carcharhiniformes (e.g., CPP, GCC, CP). Semiochemical extractions produced from one species of Carcharhiniformes have demonstrated repellency on conspecific species (e.g., CP). Semiochemical extractions produced from one or more species of Orectolobiformes have demonstrated repellency on species of Carcharhiniformes (e.g., N2, BB1). (See Table 1).

Repellency activity may be demonstrated in any method described above or known to one of skill in the art. For the investigations undertaken herein two common methods of testing repellent activity were most often used.

A pressurized fluid delivery system was designed to deliver repellent into large feeding populations of sharks. The repellent was released as a subsurface cloud, which follows the current. A 1 L plastic container containing the semiochemical solution was pressurized to approximately 20 psig with a battery compressor or hand pump. A globe valve was used to hold back the fluid. The fluid was delivered to the end of a long PVC pole using Teflon tubing. This allowed the operator to place the tip of the pole well into the population of feeding sharks. By actuating the small globe valve, a cloud of the solution was released quickly and reliably into the feeding population. Controls were established using FD&C Red 40 dye and seawater, uncolored seawater, and air. These controls established that sharks were not afraid to approach the delivery pole, nor were sharks deterred from feeding by the jet of control fluid or air. During field tests with feeding populations of up to 12 *Carcharhinus perezi* with *Carcharhinus acronatus*, we consistently observed that as little as 4 fl. oz (approx 129 ml) of semiochemical "A2" reduced the feeding population to zero within 2 minutes when administered with the above-described testing apparatus.

Another method is a "tonic immobility" study. During tonic immobility studies, semiochemical is delivered using a plastic syringe, which is not in contact with the specimen. The test solution is released within 3 inches of the specimen's nose. Controls are established using separate syringes with seawater. Some controls were released with a high flow rate (30 mL/sec) in order to establish that sharks were not awakened by the jet of fluid over their noses.

Using the above-described tests, the repellent characteristics of a wide range of semiochemicals prepared in accordance with the invention has been established. For example, semiochemical extractions produced from pelagic Lamniforms (e.g., *I. oxyrhincus*) have demonstrated repellency on inshore Carcharhiniformes. In three tests, 450 ml to 700 ml doses of semiochemical composition GWH, derived from the head of a great white shark, repelled competitively-feeding blacknose and Caribbean reef sharks. (See Table 1).

Semiochemical extractions produced from inshore Carcharhiniformes have demonstrated repellency on highly migratory (pelagic) Carcharhiniformes. A 500 mL dose of semiochemical composition A13N, derived from lemon sharks, nurse sharks, and spiny dogfish; repelled two adult blue sharks which were previously stimulated by acoustical and olfactory attractants. Similarly, a 500 mL dose of semiochemical composition GCC, derived from a tiger shark carcass, was observed to repel a large adult blue shark stimulated by acoustical and olfactory attractants.

Semiochemical extractions produced from a Squaliform repelled species of Carcharhiniformes. A 250 mL dose of Composition SQ1, derived from the Cuban Dogfish, repelled competitively-feeding blacknose and Caribbean reef sharks. (See Table 1).

Semiochemical extractions produced from one or more species of Carcharhiniformes repelled entirely different species of Carcharhiniformes. A 500 mL dose of semiochemical composition CPP, derived from the head of a sandbar shark, repelled competitively-feeding blacknose and Caribbean reef sharks. Similarly, a 500 mL dose of composition A2, derived from lemon, nurse, and dogfish carcasses, repelled two adult bull sharks stimulated with olfactory attractants.

Semiochemical extractions produced from one species of Carcharhiniformes repelled a conspecific species of Carcharhiniformes (e.g., CP). In four tests using an aerosol delivery canister, semiochemical composition CP, derived from the head of a Caribbean Reef Shark, repelled competitively-feeding blacknose and Caribbean reef sharks. (See Table 1).

Semiochemical extractions produced from one or more species of Orectolobiformes repelled species of Carcharhiniformes. In tests using captive juvenile lemon sharks, aversive swimming responses were observed with a 10 mL dose of semiochemical extraction from nurse shark carcasses. Similarly, a 10 mL dose of semiochemical from a bamboo shark carcass produced aversive swimming responses in captive juvenile lemon sharks. (See Table 1).

TABLE 1

| | REPELLENT SOURCE | | | | | |
|---|---|---|---|---|---|---|
| Blind Code | Order | Family | G. species | Section | Polar Solvent System | Decay Process |
| A | Carcharhiniformes | Carcharhinidae | N. brevirostris | whole carcass, | 50% water 40% methanol | aerobic in polypropylene |
| | Orectolobiformes | Ginglymostomatidae | G. cirratum | whole carcass, | 8.5% ethanol 1.5% methylisobutyl | at 25° C. (RT) |
| | Squaliforms | Squalidae | S. acanthias | whole carcass | ketone | |
| A2 | Carcharhiniformes | Carcharhinidae | N. brevirostris | whole carcass, | 50% water 40% methanol | aerobic in polypropylene |
| | Orectolobiformes | Ginglymostomatidae | G. cirratum | whole carcass, | 8.5% ethanol 1.5% methylisobutyl | at 25° C. (RT) |
| | Squaliforms | Squalidae | S. acanthias | whole carcass | ketone | |
| A2 | Carcharhiniformes | Carcharhinidae | N. brevirostris | whole carcass, | 50% water 40% methanol | aerobic in polypropylene |
| | Orectolobiformes | Ginglymostomatidae | G. cirratum | whole carcass, | 8.5% ethanol 1.5% methylisobutyl | at 25° C. (RT) |
| | Squaliforms | Squalidae | S. acanthias | whole carcass | ketone | |
| A2 | Carcharhiniformes | Carcharhinidae | N. brevirostris | whole carcass, | 50% water 40% methanol | aerobic in polypropylene |
| | Orectolobiformes | Ginglymostomatidae | G. cirratum | whole carcass, | 8.5% ethanol 1.5% methylisobutyl | at 25° C. (RT) |
| | Squaliforms | Squalidae | S. acanthias | whole carcass | ketone | |
| A2 | Carcharhiniformes | Carcharhinidae | N. brevirostris | whole carcass, | 50% water 40% methanol | aerobic in polypropylene |
| | Orectolobiformes | Ginglymostomatidae | G. cirratum | whole carcass, | 8.5% ethanol 1.5% methylisobutyl | at 25° C. (RT) |
| | Squaliforms | Squalidae | S. acanthias | whole carcass | ketone | |
| B | Lamniformes | Lamnidae | I. oxyrhincus | cross-section behind first dorsal | 50% water 50% acetone | aerobic in glass at 25° C. (RT) |
| B2 | Lamniformes | Lamnidae | I. oxyrhincus | cross-section behind first dorsal | 100% water | anaerobic in polypropylene at 25° C. (RT) |
| A13N | Carcharhiniformes | Carcharhinidae | N. brevirostris | whole carcass, | 50% water 40% methanol | aerobic in polypropylene |
| | Orectolobiformes | Ginglymostomatidae | G. cirratum | whole carcass, | 8.5% ethanol 1.5% methylisobutyl | at 25° C. (RT) |
| | Squaliforms | Squalidae | S. acanthias | whole carcass | ketone | |
| ML1 | Lamniformes | Lamnidae | I. oxyrhincus | liver | 50% water 50% acetone | aerobic in polypropylene at 25° C. (RT) |
| ML2 | Lamniformes | Lamnidae | I. oxyrhincus | liver | 50% water 50% acetone | aerobic in polypropylene at 25° C. (RT) |
| SQ1 | Squaliforms | Squalidae | S. cubensis | whole carcass | 50% water 40% methanol 8.5% ethanol 1.5% methylisobutyl ketone | aerobic in polypropylene at 25° C. (RT) |
| CPP | Carcharhiniformes | Carcharhinidae | C. plumbeus | head | 50% water 40% methanol 8.5% ethanol 1.5% methylisobutyl ketone | aerobic in polypropylene at 25° C. (RT) |
| GWH | Lamniformes | Lamnidae | C. carcharias | head | 50% water 40% methanol 8.5% ethanol 1.5% methylisobutyl ketone | aerobic in polypropylene at 25° C. (RT) |
| GCC | Carcharhiniformes | Carcharhinidae | G. cuvieri | cross section behind pectoral fins | 50% water 40% methanol 8.5% ethanol 1.5% methylisobutyl ketone | aerobic in polypropylene at 25° C. (RT) |

TABLE 1-continued

| | | | | | | |
|---|---|---|---|---|---|---|
| CP | Carcharhiniformes | Carcarhinidae | C. perezii | head | 50% water 40% methanol 8.5% ethanol 1.5% methylisobutyl ketone | aerobic in polypropylene at 25° C. (RT) |
| N2 | Orectolobiformes | Ginglymostomatidae | G. cirratum | whole carcass | 50% water 40% methanol 8.5% ethanol 1.5% methylisobutyl ketone | aerobic in polypropylene at 25° C. (RT) |
| BB1 | Orectolobiformes | Hemiscyllidae | C. punctatum | whole carcass | 50% water 40% methanol 8.5% ethanol 1.5% methylisobutyl ketone | aerobic in polypropylene at 25° C. (RT) |

| | TARGET | | | TEST | | | |
|---|---|---|---|---|---|---|---|
| Blind Code | Order | Family | G. species | Dose | Method | Population | Response |
| A | Carcharhiniformes | Carcarhinidae | C. acronotus C. perezii | 500 ml | cloud | 15 | repelled while stimulated with bait |
| A2 | Carcharhiniformes | Carcarhinidae | C. acronotus C. perezii | 500 ml | cloud | 12 | repelled while stimulated with bait |
| A2 | Carcharhiniformes | Carcarhinidae | N. brevirostris | range 7 ml to 30 ml | TI | 1 | terminated tonic immobility |
| A2 | Carcharhiniformes | Carcarhinidae | C. leucas | 500 ml | cloud | 2 | repelled while stimulated with bait |
| A2 | Carcharhiniformes | Carcarhinidae | C. limbatus | 1 ml/min point source | johnson-baldridge | 1 | protected bait at point source for 1 hour until pump battery died |
| B | Carcharhiniformes | Carcarhinidae | C. acronotus C. perezii | 200 ml | cloud | 12 | repelled while stimulated with bait |
| B2 | Carcharhiniformes | Carcarhinidae | C. acronotus C. perezii | 1 qt | cloud | 6 | no behavioral change, feeding continued |
| A13N | Carcharhiniformes | Carcarhinidae | P. glauca | 500 ml | cloud | 2 | repelled while stimulated with bait and acoustics |
| ML1 | Carcharhiniformes | Carcarhinidae | C. perezii C. acronotus | 700 ml | cloud | 8 | repelled while stimulated with bait |
| ML2 | Carcharhiniformes | Carcarhinidae | C. perezii C. acronotus | 700 ml | cloud | 8 | repelled while stimulated with bait |
| SQ1 | Carcharhiniformes | Carcarhinidae | C. perezii C. acronotus | 250 ml | cloud | 12 | repelled while stimulated with bait |
| CPP | Carcharhiniformes | Carcarhinidae | C. perezii C. acronotus | 500 ml | cloud | 7 | repelled while stimulated with bait |
| GWH | Carcharhiniformes | Carcarhinidae | C. perezii C. acronotus | 500 ml | cloud | 9 | repelled while stimulated with bait |
| GCC | Carcharhiniformes | Carcarhinidae | P. glauca | 500 ml | cloud | 2 | repelled while stimulated with bait and acoustics |
| CP | Carcharhiniformes | Carcarhinidae | C. perezii C. acronotus | 6 fl oz | Aerosol | 12 | repelled while stimulated with bait |
| N2 | Carcharhiniformes | Carcarhinidae | N. brevirostris | 10 ml | syringe | 1 | aversive swimming behavior observed after dose in captive tank |

TABLE 1-continued

| | | | | | | | |
|---|---|---|---|---|---|---|---|
| BB1 | Carcharhiniformes | Carcarhinidae | N. brevirostris | 10 ml | syringe | 1 | aversive swimming behavior observed after dose in captive tank |

Notes for Table 1:
The solvent system usually represents 50% w/w water with 50% of the mixture of 80% MeOH, 17% EtoH, and 3% methyl isobutyl ketone
P. glauca = blue shark, a highly migratory (pelagic) shark, not an inshore species
C. leucas = considered the most dangerous inshore shark species
C. punctatum = brownbanded bamboo shark, a harmless hand-sized shark
I. oxyrhincus = shortfin mako shark, obtained as steaks or liver
C. carcharias = great white shark, considered the most dangerous epipelagic shark species, 2nd most dangerous inshore
G. cuvieri = tiger shark
C. plumbeus = sandbar shark
C. perezii = Caribbean reef shark
C. acronotus = blacknose shark (not blacktip, C. limbatus)
S. cubensis = (deepwater) Cuban dogfish
S. acanthias = spiny dogfish
G. cirratum = nurse shark
N. brevirostirs = lemon shark
The following compounds have been established as effective controls in stimulated, tonically immobilized, and non-stimulated free-swimming sharks under chemical repellent evaluation:
seawater, dose ranges 100ul to 1000 ml
HPLC grade micron-filtered water, dose ranges 1 ml to 10 ml
methanol/ethanol/mibk/water solution dos at approx 500 ml
methanol/ethanol/mibk solution dose ranges 1 ml to 6 ml
diethylene glycol monoethyl ether dose ranges 1 ml to 6 ml
acetone/water solution dose at approx 500 ml Semiochemical extractions produced from a tiger shark (Order Carcharhiniformes) repelled a juvenile Mako shark (Order Lamniformes, Family Lamidae, Genus *Isurus*) discussed in Example 12 below.

In sum, it has been demonstrated that a semiochemical extraction of the order Lamniformes repels a Carcharhiniform, a semiochemical extraction of the order Carcharhiniformes repels a Lamniforme, a semiochemical extraction of the order Orectolobiform repels a Carcharhiniform and a semiochemical extraction of the order Squaliform repels a Carcharhiniform. Likewise, a semiochemical extraction of the order Carcharhinoform conspecifically repels a Carcarhiniform. (See Table 1).

The repellents and methods describe herein provide the artisan with chemicals that have been demonstrated to repel, at very low concentrations, families of shark known to migrate in shallow coastal waters and species known to attack humans. In contrast to earlier ineffective chemicals, the inventors have discovered and herein disclose an effective semiochemical repellent shown to result from decomposing shark tissue. Controlled studies of these substances have shown that feeding is halted in a variety of species of sharks at low concentration. The present invention overcomes the hazards of earlier-tested noxious chemicals such as the nerve toxin VX by producing a safe-to-handle extract that does not to harm or kill sharks, does not harm humans and does not harm other marine organisms. Further, it is reported herein that teleost fishes, such as the Yellowfin Tuna, demonstrate no aversive response in the presence of repellents of the invention. Only sharks appear to be deterred by the compounds.

III. METHODS AND DEVICES OF DELIVERY OF REPELLENT

Once prepared using the methods of the invention, a semiochemical repellent may be delivered to the environment of an elasmobranch through a variety of methods and devices of delivery. Alternative non-limiting embodiments of methods of and devices for delivering a semiochemical repellent into an elasmobranch environment include an extendable pressurized delivery device such as a pole with a pressurized discharge tube for safe delivery to stimulated sharks during scientific inquiry, a pressurized repellent gun, a miniature pressurized repellent gun to be worn on the wrist or ankle, a spear fishing gun with an adjacent repellent cylinder, a time release sponge-material attached to a surfboard or otherwise placed near a diver, swimmer or in some other place of interest, a hollow surfboard with a calibrated drip to emit repellent, a pump delivery system affixed to a surfboard, a pressurized delivery device affixed to a surfboard wherein discharge of repellent may be triggered by the surfer, a floatation device, a wristwatch filled with repellent (pressurized or unpressurized), a carbon dioxide activated pressurized syringe, an aerosol bomb, a mortar-launched aerosol bomb, a remote-controlled buoy with a repellent tank that may be fired by a lifeguard or other person or mechanized system, a buoy with a metering pump that runs during swim time (daylight), a repellent pouch attached to longlines (muslin/burlap bags) or to clothing or surfboard or other water device, jellied repellent (glycol ether/hydroxypropylcelluose gels which time-dissolve in water), sunscreen/sun care formulations containing repellent, lotions containing repellent, porous fabric impregnated with repellent, rechargeable porous fabric impregnated with repellent, a kite- or balloon-deployed repellent bomb (remote control), a submerged repellent mine (remote control) for deeper water, a cattle-treatment drench gun converted to shark repellent gun (http://www.dr-register.com/drenchgun.htm), repellent-impregnated cable insulation and cable jackets for undersea lines.

Exemplary, non-limiting devices for and methods of administering elasmobranch repellents are discussed in detail in the following section.

A variety of delivery devices known in the art are illustrated in FIG. 24. For example, semiochemical repellent may be discharged through a pressurized tube that runs alongside an extended or extendable poll. (FIG. 24A.) The pressurized delivery pole apparatus may be useful for administering repellent to feeding or otherwise stimulated sharks. The apparatus may comprise a delivery device housing (pole) (310) with a repellent discharge tube (320) housed along or within the pole. The repellent discharge tube may be connected to a pressurized chamber or chambers (340) containing repellent (360). The delivery device may contain a check valve (370) to facilitate the maintenance of pressure. A trigger (350) may allow the pressurized repellent to discharge through the tube (320) and away from the pole (310). The pole may also contain a hook (330) or other device for presenting bait or other stimulant to the sharks at the end of the pole (310). During experimentation, the tube may be connected to more than one chamber (340) containing more than one experimental repellent solution (360). An alternative delivery device may be a pressurized syringe. (FIG. 24B.) Such a syringe (410) may be filled with repellent (450). It may have a plunger (420) to provide pressure and optionally to expel the solution from the syringe. It may also comprise a trigger (450), a check valve (470), a pressure release cap (490) and a nozzle (425). When the plunger is pressed, the cap (490) pops off the syringe and the pre-pressurized repellent is expelled in a pressurized stream. A commercially available delivery device is a cattle-treatment "drench" gun converted into a shark repellent gun comprising a reservoir (401) for repellent (402) and plunger (404) with reservoir filling handle (407), a trigger (405) and a discharge tube (406). (FIG. 24C.) The drench gun may be obtained from Dr. Register & Associates, 1513 5th Ave., East Menomonie, Wis. A cattle-treatment drench gun may be used to deliver a pressurized stream of semiochemical repellent in accordance with the present invention.

A. Pressurized Container Delivery Device

An exemplary and non-limiting semiochemical delivery device in accordance with the invention is a pressurized container comprising semiochemical. The container preferably may be of sufficient size to contain, and likewise comprise, sufficient repellent for at least one delivery of semiochemical sufficient to evoke a flight response in a shark, e.g., an aerosol can filled with repellent. (See FIG. 25.) The container may be constructed of degradable material. A non-limiting pressurized aerosol container (10) for administration of semiochemical repellent to a shark environment in accordance with the present invention may comprise a pressurized container (11) with sufficient tensile strength for pressurization and preferably sufficient capacity to hold a sufficient amount of semiochemical repellent (50) to repel at least one elasmobranch upon administration to water. The container may preferably be of sufficient size to be held comfortably in the human hand such that it could be thrown or released into water from the human grasp. The pressurized delivery device (10) may further comprise compressed gas (40) sufficient to expel the semiochemical repellent (50) contained therein. The container is preferably asymmetrically weighted having a weight (13) at the top (12) or base (14) portion of the container. The position of the weightedness of the container may be varied throughout the shape of the delivery device. The device may further comprise a nozzle (22) that is preferably a directional discharge nozzle. The device may further comprise an actuator (21) that when engaged allows the compressed contents of the aerosol container to be expelled. The device further preferably comprises a continuous discharge apparatus (20) to allow the contents of the can to be expelled with a single activation of the discharge apparatus (20). Preferably, when the actuator (21) is engaged, the nozzle (22) remains open to allow the can to be continuously and fully evacuated. The actuator preferably cannot be casually disengaged once engaged. The device (10) preferably floats. When the actuator (20) is engaged and the container (10) is disposed in water (60) the combination of continuous discharge, asymmetrical weight and motion of water allows the container (10) to move erratically on the surface of the water while spraying a cloud (61) of repellent into the water and placing a mist of repellent in the air (62) just above the surface of the water (60). Cloud dispersion, as used in this specification, includes dispersion in the air or water wherein the repellent is delivered as a liquid, mist, spray or foam. The directional movement of the device (10) may be alternatively manipulated by moving the relative positions of a weighted portion (13) of the container. As illustrated, the container (10) should discharge repellant proportionately more in the water than in the air since the weight (13) is in vicinity of the actuator (20). Movement may also be altered by altering the shape (15) of the container or by altering the direction of the discharge of the nozzle (22). For example, the canister may be in the shape of a ball, thereby limiting the impact of axial rotation, and the direction of discharge may be positioned to discharge along the canister axis, thereby limiting the impact of medial rotation.

Erratic motion may be created by several characteristics of a pressurized container, each characteristic representing a non-limiting alternative of a delivery device in accordance with the invention. In a non-limiting preferred alternative, an aerosol container of the invention floats. This allows erratic movement on the surface of the water as the repellent is expelled at or near the surface of the water. In another non-limiting alternative, the container does not float. It sinks into the water and repellent is discharged directly into the water where it provides a high concentration of the repellent in a desired place.

In a non-limiting alternative, the container is cylindrically shaped such that it will spin axially and medially while the repellent is expelled. Spinning rapidly may lure sharks while spraying repellent in a wide area. In another alternative, the delivery device may have more than one nozzle such that repellent may be released in more than one direction at once.

In a non-limiting configuration, the device is heavier on an end of the container not comprising a nozzle. In a non-limiting preferred configuration, the device is heavier on an end of the container comprising a nozzle. When the container with pressurized repellent is placed in water, the weightier end initially sinks into the water and directs the nozzle into the water. When discharged into the water, the force of expulsion drives the nozzle into the air. When discharged into the air, the repellent travels considerably farther before settling to the surface of the water than it would after direct discharge into the water. In another non-limiting preferred configuration having a weightier nozzle end, when initial discharge occurs into the water, the pressure from the discharge drives the nozzle into the air. When the nozzle reaches the surface of the water, the combination of weightedness and pressure from discharge drive the nozzle to the water. A series of these opposing forces results in discharge of the semiochemical over a wide range, covering a large arc both in the air and in the water. Such an asymmetrical embodiment of a container would move more erratically in the water as the volume of pressurized repellent is released than would a symmetrical embodiment. Erratic movement is created by, among other things, the pressure of the released repellent acting against the weight of the nozzle-end of the container and the buoyancy of the container floating in the waves of the body of water. (See FIG. 25.) The erratic motion also acts as an attractant to sharks and serves as a mechanism to distract sharks away from swimmers or other endangered things and than to repel the shark from the surrounding area by directly exposing the shark to a concentration of repellent near the container.

B. Mortar-Launched Aerosol Bomb

Figure 26:
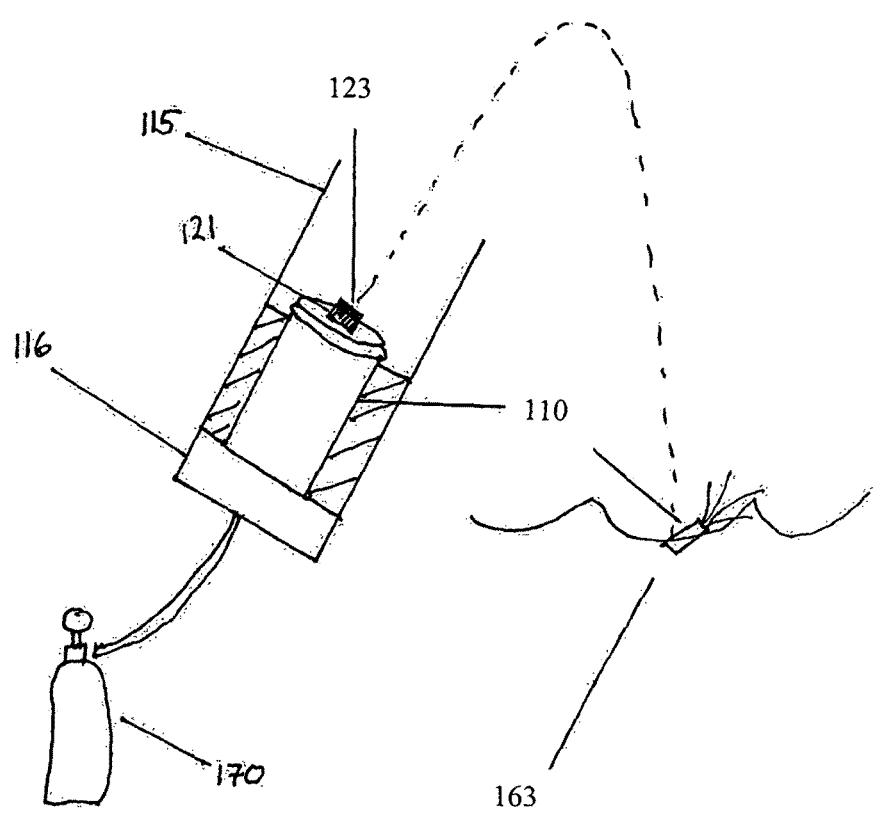
FIG. 26 illustrates a mortar-launched aerosol "bomb" canister for administration of semiochemicals in accordance with the present invention from a distance.

A non-limiting delivery device of the invention comprises delivery of a pressurized container or a pouch containing repellent of the invention into the ocean from a mortar tube activated with compressed gas. (FIG. 26.) In one aspect of the delivery device, the container is an aerosol container (110) and is placed in a mortar tube (115) with a compressed-gas-mortar-charging-device (116) beneath the container (110). Activation of compressed gas (170) launches the canister in an arc toward a desired elasmobranch environment (163). The actuator (121) is triggered by dissolution of the actuator plug (123) when the canister encounters the water. In a preferred embodiment, dissolution of the actuator plug (123) actuates discharge of the repellent within several seconds. The mortar tube allows access to elasmobranch environments that are not immediately otherwise accessible. Discharge of the mortar tube propels the container over a distance toward an area where a shark may be expected or detected.

C. Raft/Buoy Delivery Device

Figure 27:
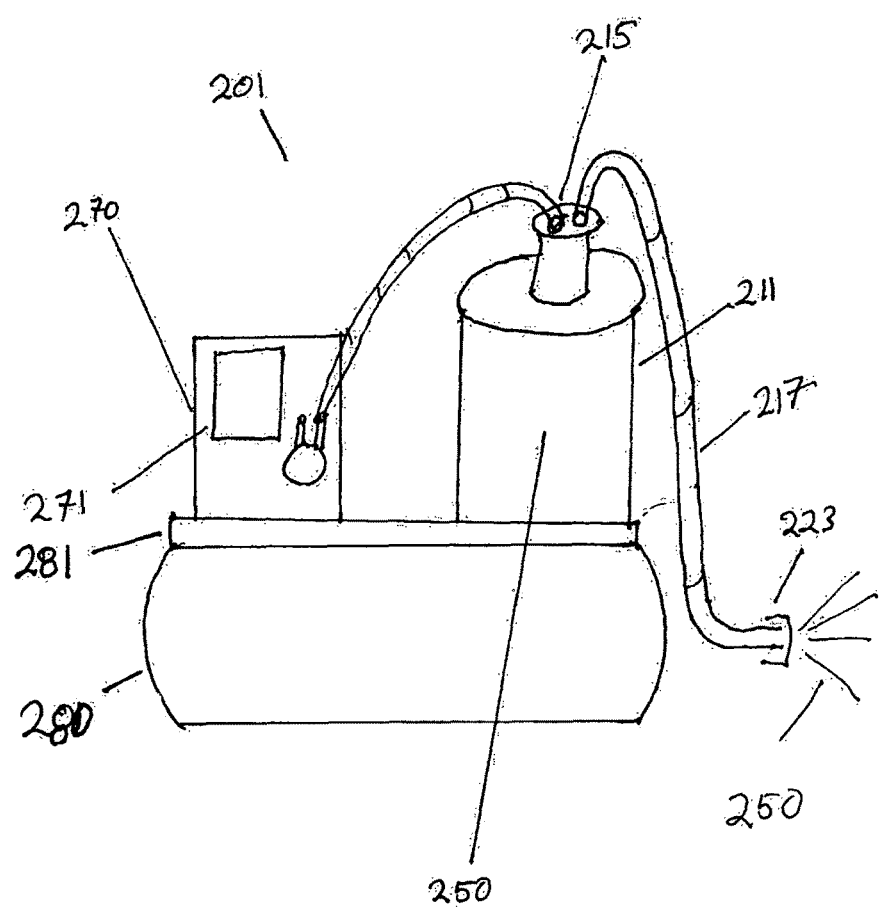
FIG. 27 illustrates an automated repellent dispenser in accordance with the present invention comprising a raft or other floating or fixed device that delivers repellent by discharging repellent above the surface of the water.

Another non-limiting delivery device of the invention comprises a raft (201) or other floating or fixed device comprising a floating buoy (280), a solid platform (281), and a container (211) of repellent (250) connected to a pump (270) with a power source (not shown) that is capable of delivering repellent into a shark environment either by automatic timing, remote triggering or other actuating mechanism (271). The container (211) comprises a check valve (215) that allows the pump (270) to build pressure in the container (211) to a desired pressure. When a desired pressure is achieved, a release valve (223) or pressure-release cap releases the pressurized repellent (250) into a delivery tube (217). The repellent is expelled across the water, spreading a wide cloud of repellent. (FIG. 27.)

The pump may be automatically activated by a timer or may be activated remotely. The pump preferably delivers sufficient repellent into the water to repel sharks. Preferably, the discharge tube is long enough and not submerged such that when delivery begins, the repellent is sprayed a substantial distance onto the surface of the water and, under pressure, the discharge tube (217) moves erratically across a large radial area in relation to the raft (201). In a preferred embodiment the discharge tube is made of flexible material. Preferably the discharge tube will spray over an entire 360 degree arc.

A specific non-limiting preferred device in accordance with the invention is a raft/buoy that holds 2 liters of repellent. (See FIG. 27.) The raft is anchored, e.g., at a sandbar or a region where a shark might enter a shallow swimming area. If a shark is spotted by a lifeguard, the lifeguard would hit a remote control button. At the buoy or raft, a radio receiver switches on the air pump. Air is pumped quickly into the 2 liter plastic tank, which has a check valve to allow fast buildup of head pressure. Once enough pressure builds up, a cap on the delivery tube pops off of the tube, spraying repellent multi-directionally at about 20-30 psi.

D. Hand-Held Pressurized Discharge Delivery Device

A non-limiting delivery device in accordance with the invention is a delivery device and method of delivery of semiochemical repellent using a pressurized directional device. (See FIGS. 28 and 31.) The pressurized directional device comprises a sufficiently sized container for repellent to provide sufficient repellent to the environment of a shark to evoke a flight reaction. The pressurized directional device further comprises a pressurizing mechanism such as a pump or a compressed gas cylinder through which a pressure may be placed on the container of semiochemical repellent to expel the repellent. The pressurized directional device further comprises a discharge nozzle that preferably focuses a stream of semiochemical repellent in a particular direction under pressure when the repellent is expelled from the pressurized chamber. The pressure in the container of repellent is maintained, for example, with a check valve. The pressurized directional delivery device further comprises a mechanism for releasing the pressurized repellent through the delivery nozzle, such as a valve or cap that releases at a prescribed pressure or upon trigger by the user. In a non-limiting alternative, the gun is fitted with backpack straps (595). (See FIG. 31.)

Figure 28:
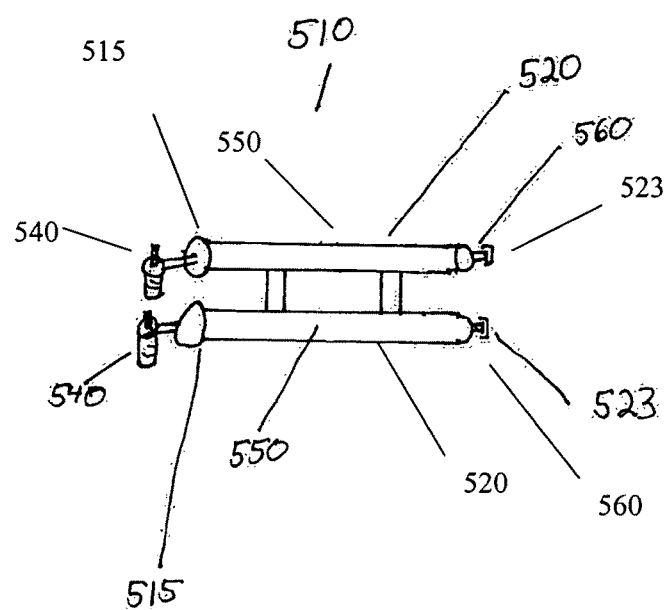
FIG. 28 illustrates a duel barreled semiochemical repellent discharger in accordance with the present invention.
Figure 29:
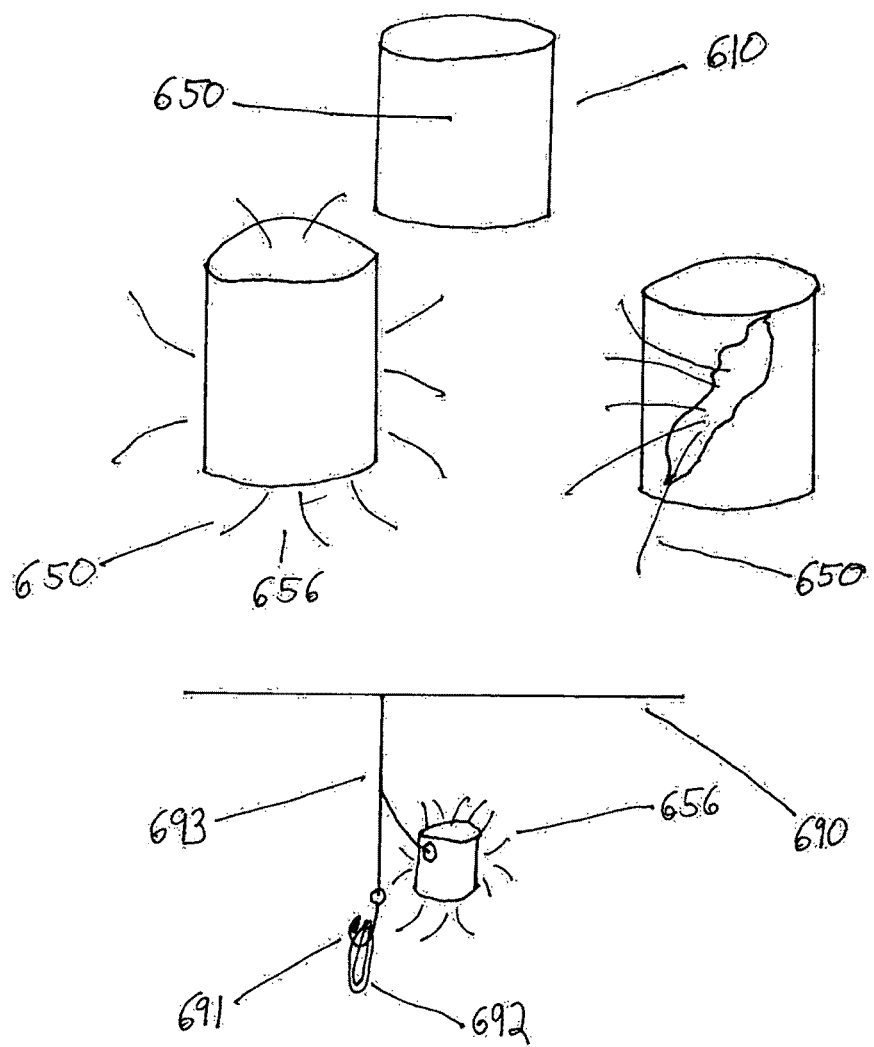
FIG. 29 illustrates semiochemical repellent pouches in accordance with the invention.

A specific non-limiting semiochemical delivery device in accordance with the invention may also comprise a semiochemical repellent gun (510). (FIG. 28.) The gun may have one or more chambers (520) for repellent (550), each chamber connected to at least one source of compressed air (540) through a check valve (515). The end of the chamber may have a capped directional outlet (560). When the compressed air is introduced through the check valve (515) and the cap (523) is sprung from the end of the gun, the repellent (550) in the chamber is expelled in the direction of a shark or the environment of a shark. The discharge nozzle may be connected to a tube of any length to discharge the repellent over any length necessary to deliver the repellent into a desired environment.

E. Repellent Dispersing Pouch

A non-limiting semiochemical delivery device in accordance with the invention (see FIG. 28) also comprises a pouch (610) containing repellent (650). Repellent may be in the form of a solution or solid, preferably partly or wholly soluble. The repellent may be introduced to the environment of the shark by diffusion or by rupturing (655), tearing or otherwise penetrating the pouch. A pouch may also diffuse (656) repellent through its fabric. A diffusing pouch may be attached to a fishing net or longline (690) with a baited hook (691) on a snood (693) to allow repellent to slowly diffuse (656) into the water surrounding bate (692) or fishing net. The pouch will provide sufficient repellent around the baited hook to repel sharks while not repelling the desired teliost fish. A pouch to be placed on a longline may preferably be constructed of muslin or burlap.

F. Longline Fishing Delivery Device

Sharks represent a significant problem in the long line fishing industry. Commercial longline fishing operations routinely target swordfish and tuna, however, the hook is not selective, and sharks are sometimes caught in greater numbers than the intended catch. A non-limiting method of delivery of semiochemicals in accordance with the invention is a mass or part or piece of decayed elasmobranch treated with a polar solvent.

Semiochemicals on longlines in accordance with the invention are preferably soluble in seawater, and, at a sufficient concentration to produce flight responses in elasmobranches. Teleost fish are not affected by the semiochemicals. It is theorized that this phenomenon is determined by receptor specificity. Yellowfin tuna (*T. albacares*) and six species of reef fish were observed to feed directly in a cloud of the semiochemical.

Since shark-repelling semiochemicals can be derived from decayed shark carcasses, sections of an actual shark carcass are utilized in accordance with a non-limiting aspect of the invention to control by-catch. Small pieces of the carcasses, which have been aerobically decayed and exposed to polar solvents, are suitable as a source of semiochemicals and also remain on a hook for considerable periods of time. The piece of decayed polar solvent treated carcass is applied to the hook along with standard bait or attractant, such as mackerel or squid, in approximately equal mass. Therefore, each hook contains two pieces of material: an attractant for fish and sharks, and a shark repellent. Since the target fish do not detect the shark-repelling semiochemicals, they are likely to navigate to the attractant/bait and strike the hook. However, a shark navigating the odor plume towards the hook will continue to experience an increasing concentration of the semiochemical and will find the bait less attractive. The bait will therefore be avoided by sharks but attracted by commercially valuable fish.

When producing semiochemicals by extraction, it is desirable to utilize blue shark (*Prionace glauda*) carcasses, since this species presents the largest by-catch in commercial longline fisheries. Two adult blue carcasses are sufficient to produce at least 200 hooks worth of repelling mass. As a result, the carcass of two blue sharks has the potential to spare the lives of 198 other sharks.

The decayed polar solvent treated shark carcass must not be employed before the proper semiochemicals have been produced. A freshly-killed shark carcass, for example, serves as an attractant for other sharks. Even carcasses which have been decaying for days may not possess the proper flora of semiochemicals. Decay conditions must be carefully controlled. For example, anaerobically-decayed carcasses are not suitable. Also, most non-polar solvents kill or inhibit sufficient bacterial and enzymatic reaction necessary to produce semiochemicals. Therefore, the manufacturer must possess the proper analytical tools in order to detect the presence of semiochemicals.

Once semiochemicals in sufficient abundance are detected, the decay process may be halted either by lowering temperature, immersion in solvents for preservation until use, or by filtering the extraction. If catabolism continues unchecked, all tissue will be putrefied and the semiochemical compounds will be catabolized into other products. Usually, the detection of large quantities of uric acid signals that catabolism has progressed too far.

The mass of decayed shark carcass ranges from 40 g to 200 g, practically, but may be expanded to 10 g to 500 g in order to match the mass of the attractant bait used. Larger quantities of the decayed matter are typically used when whole mackerel are deployed as the bait.

It is desirable to encase the individual masses of decayed shark carcass in a disposable container or slow-dissolving polymer matrix which activates in water, such as a high molecular-weight Dow Chemical Polyox. Properly-decayed shark carcasses may also undergo a secondary chemical treatment which introduces other repellent compounds into the tissue. For example, Composition 3M4, produced by SharkDefense LLC, is a gustatory repellent in sharks. The decayed matter may be treated with a solution of dimethylsulfoxide and Composition 3M4, thereby impregnating the decayed matter with a second potent repellent.

Another non-limiting alternative comprises a tube extending the length of the longline comprising discharge tubes at each snood. (See FIG. 30.) A pump may meet sufficient repellent to each discharge tube to repel sharks. Another embodiment comprises the structure of FIG. 30 over a relatively small distance, such as 20 feet. This embodiment is especially useful for research related to shark repellents. This embodiment may also be applied, for example, to buoys surrounding, e.g., a swimming area.

Repellent may also be applied along the entire longline by brushing or soaking prior to placing the longline into the water. Likewise, the longline may comprise porous material that will allow adsorption of repellent and discharge of said repellent over time. In another non-limiting delivery device for longline fishing in accordance with the invention, semiochemicals or a mass of carcass comprising semiochemicals may be affixed to a net or other kind of fishing tackle.

Figure 30:
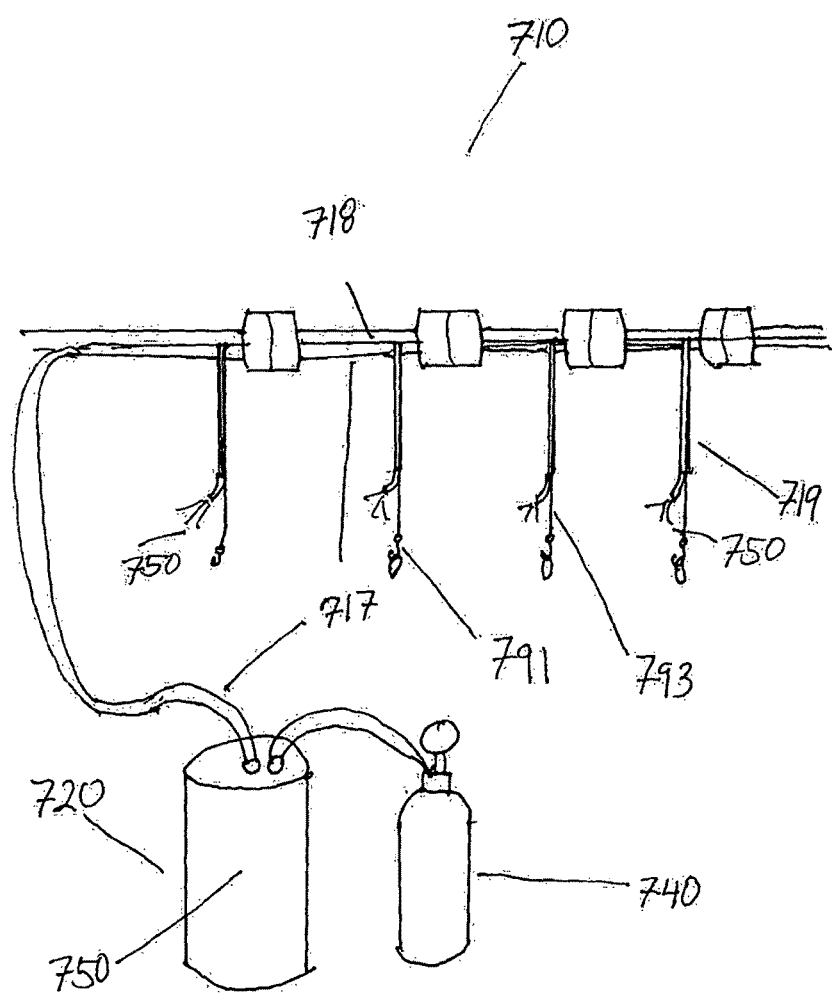
FIG. 30 illustrates an apparatus for administering repellent along fishing longline in accordance with the present invention.

A non-limiting semiochemical delivery device in accordance with the invention may also comprise an apparatus for administering repellent along longline fishing tackle. (FIG. 30.) The apparatus (710) comprises a pressurized chamber (720) connected to a source of compressed gas (740), contains repellent (750) and is connected to a primary delivery tube (717). The primary delivery tube is positioned adjacent to or otherwise in concert with the longline (718). Additional secondary delivery tubes (719) are joined to the primary delivery tube (717) in proximity to each snood (793) of the longline. The secondary delivery tubes terminate near the baited hook (791) of the snood. When pressurized repellent is released from the chamber (720), the repellent is delivered along the primary delivery tube (717) and into the secondary delivery tubes (719) thereby discharging repellent (750) near the baited hook (791) and repelling sharks from the bait.

G. Backpack Pressurized Delivery Device

Figure 31:
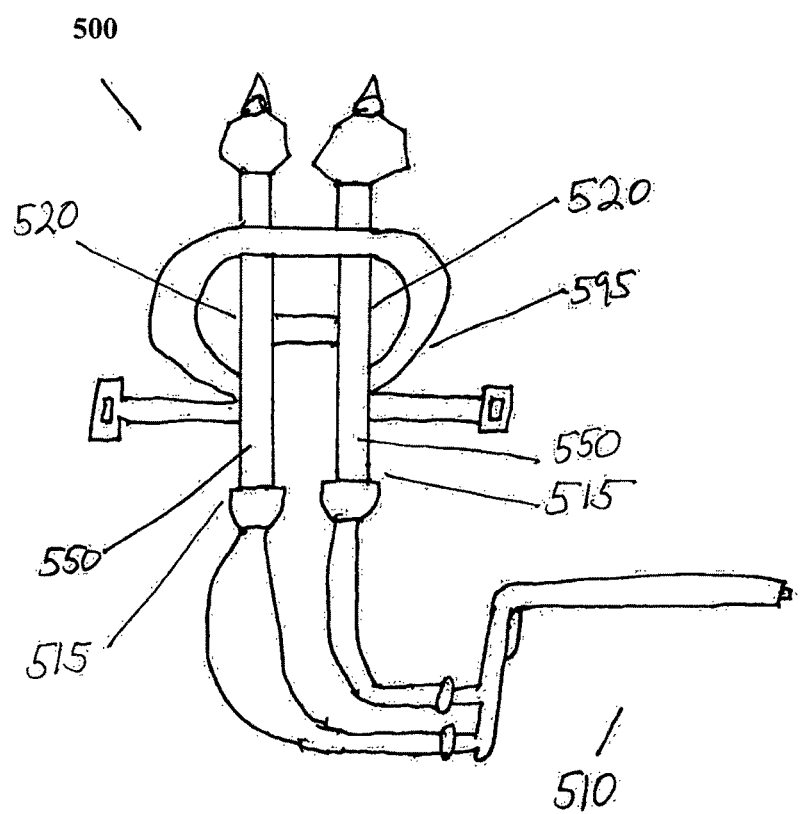
FIG. 31 illustrates a semiochemical repellent backpack discharger in accordance with the present invention for use, for example, by scuba divers and those who snorkel.

A non-limiting semiochemical delivery device in accordance with the invention may also comprise a backpack (595) repellent delivery device (500) comprising two chambers (520) of pressurized repellent (550) and a nozzled spray gun (510). (FIG. 31.) The backpack may be worn by scuba divers or snorkelers or other and may provide two or more charges of elasmobranch repellent while diving or snorkeling without resort to a repellent source on shore.

H. Spear Gun with Pressurized Delivery Device

Figure 32:
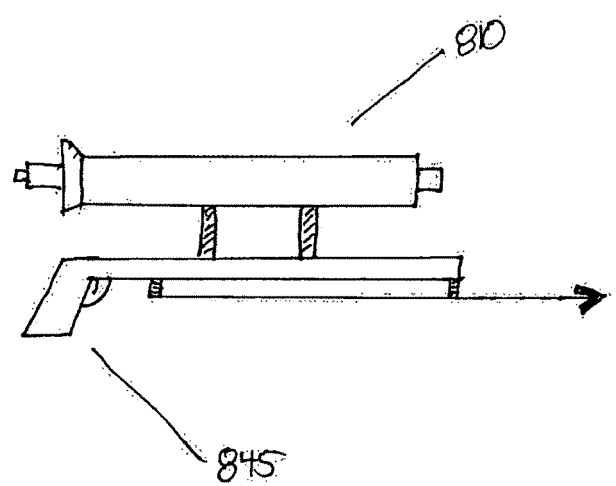
FIG. 32 illustrates a spear gun fitted with a repellent discharge device in accordance with the present invention.

A non-limiting semiochemical delivery device in accordance with the invention may also comprise a spear gun (845) further fitted with a repellent gun (810), as described in section D above. (FIG. 32.)

I. Surfboard Fitted with Delivery Device

Figure 33A:
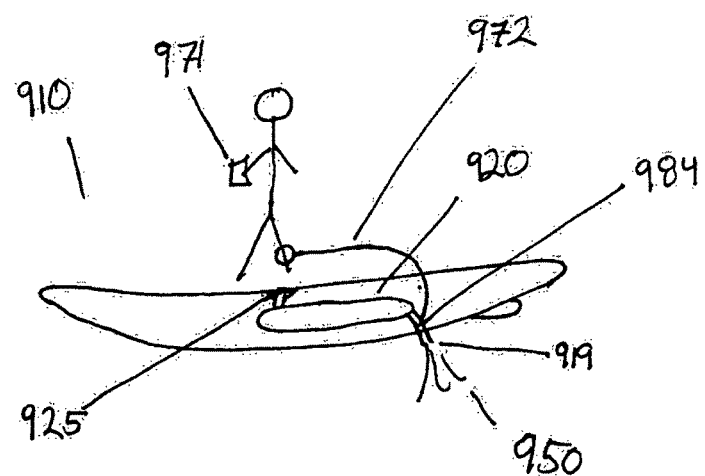
FIG. 33A illustrates a surfboard with a pressurized chamber that is discharged by a surfer in an emergency.
Figure 33B:
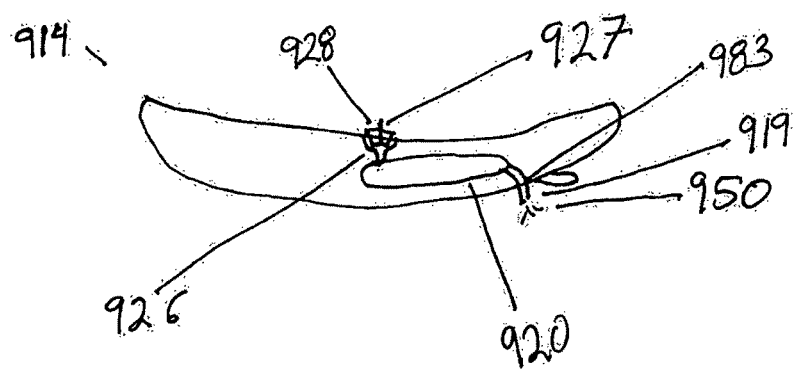
FIG. 33B illustrates a surfboard with a chamber for containing repellent and a drip valve and vent for continuous discharge during surfing.

A non-limiting semiochemical delivery device in accordance with the invention may comprise a surfboard comprising a hollow chamber for containing semiochemical repellent. FIG. 33A illustrates a specific non-limiting embodiment of surfboard with a pressurized chamber that is discharged by the surfer in an emergency. A surf board (910) comprising a pressurized chamber (920) for repellent (950) comprising a source of compressed gas (925) for expelling repellent (950) through a release valve (984) and into a discharge tube (919) in, for example, an elasmobranch emergency situation. Discharge of repellent may be triggered by a surfer via a remote control triggering device (971) or with an ankle-band triggering device (972) or wrist-band triggering device. In another specific and non-limiting embodiment, the discharge tube (919) allows repellent to be periodically introduced into the environment of the surf board via a drip valve (983). In such an alternative, the chamber (920) need not be held under pressure and no source of compressed gas is necessary. Instead, the repellent may be allowed to leak through the drip valve (983) by supplying, for example, a source of air or vent (927) in a cap or other sealant (928) of a reservoir-filling end (926) of the chamber (920). FIG. 33B illustrates such a surfboard with a chamber for containing repellent (920) a drip valve (984) a vent (927) and a discharge tube (919) for continuous discharge of repellent (950) during surfing. A chamber alternatively may be strapped to the side of the surfboard. A further alternative comprises a plastic container drilled into the surface of the surfboard. One or more than one discharge tube is contemplated.

J. Wristwatch Delivery Device

Figure 34:
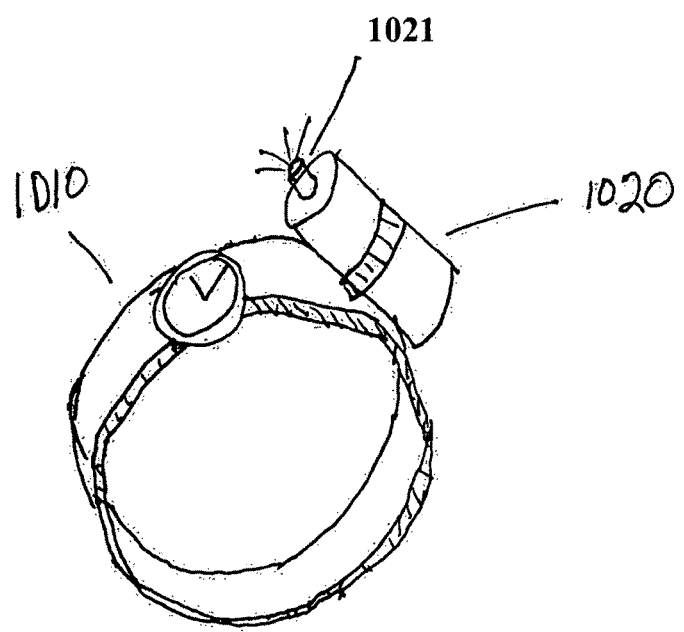
FIG. 34 illustrates a wristwatch comprising a repellent canister in accordance with the present invention.

FIG. 34 illustrates a non-limiting delivery device in accordance with the invention comprising a wristwatch (1010) and further comprising a repellent chamber or container (1020). In a non-limiting aspect in accordance with the invention the chamber is pressurized. Repellent is released from the chamber by activating a trigger (1021). In a specific non-limiting embodiment another non-limiting aspect in accordance with the invention a cap is removed. In another specific alternative embodiment the chamber is ruptured with a knife or by applying pressure.

K. Belt or Bracelet Delivery Device

Figure 35A:
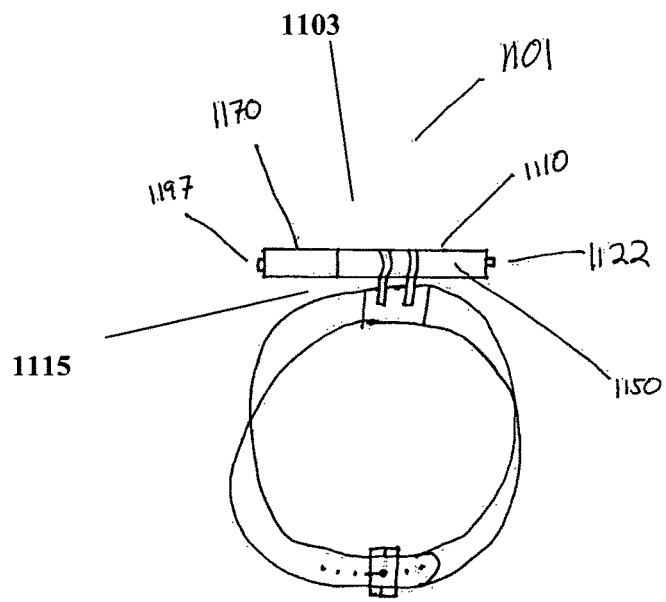
FIG. 35 illustrates a belt (FIG. 35A) or bracelet (FIG. 35B) comprising pressurized repellent in accordance with the present invention.
Figure 35B:
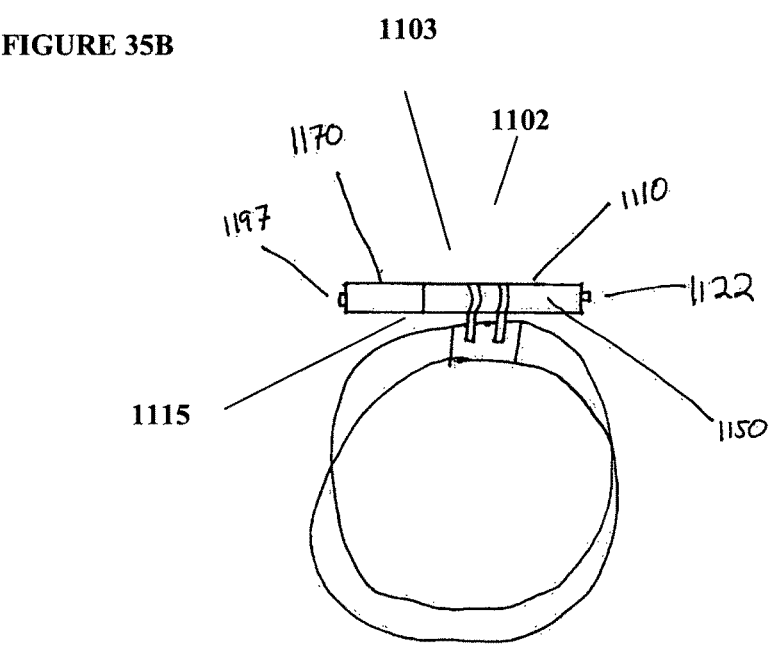

FIG. 35 illustrates a non-limiting delivery device attached to a belt (FIG. 35A) or bracelet (FIG. 35B) and further comprising pressurized repellent in accordance with the present invention. A specific non-limiting embodiment alternative comprises a wristband (1101) or belt (1102) with a repellent gun (1103) with a chamber (1110) containing pressurized repellent (1150), a source of compressed gas (1170) a check valve (1115) a trigger (1197) and a nozzle with a pressure release valve (1122) to discharge the repellent into the environment of the wearer of the wristband and preferably in a desired direction.

The invention is further described with the following non-limiting examples, which are provided to further illuminate aspects of the invention.

IV. EXAMPLES

Example 1

Preparation and Testing of Semiochemical GWH

Example 1A

Preparation of Semiochemical GWH from Order Lamniformes

GWH was aerobically prepared from the head of a great white shark (*C. carcharias*, Order Lamniformes) in a polypropylene extraction vessel. The carcass head was allowed to decay aerobically for 10 days in a covered polypropylene container. The carcass head was then fully immersed in solvent in a polypropylene extraction vessel. The extraction solvent was 50:50 water:solvent, by weight. The solvent was 80% methanol, 17% ethanol, and 3% methyl isobutylketone. Extraction time was 6 months at 25° C. with slow agitation (container was shaken or stirred during sampling intervals). The extraction was periodically sampled by HPLC in accordance with the above described method. After several months signature peaks were noted at about 5, about 6 and about 7 minutes. The extraction process was terminated by filtering to remove tissue. The resulting filtrate was containerized in a polypropylene container. Extraction time was 6 months at room temperature. The carcass processed for semiochemical GWH was obtained from the U.S. Government (National Oceanic and Atmospheric Administration Fisheries Service—Galveston, Tex. (USA)), which had frozen the great white shark carcass after it had been caught as bycatch.

Example 1B

Testing of Semiochemical GWH for Repellent Activity

GWH was tested for repellent activity against blacknose sharks (*C. acronotus* Order Carcharhiniformes) and Caribbean reef sharks (*C. perezii* Order Carcharhiniformes) present in a population of 9 sharks. The target sharks were stimulated with bait. A 500 mL dose of GWH was introduced to the shark population as a cloud. The sharks were visibly repelled from the feeding zone. (See Table 1).

Example 1C

UV-Vis Spectrum of Semiochemical GWH

GWH was spectrophotometrically analyzed in the uv-visible range. A dual-beam Perkin Elmer Lambda 12 model scanning spectrophotometer was used. Neat semiochemical solutions were micron-filtered and loaded into quartz cuvettes. Representative uncontaminated solvents were used in the extraction process, at the same ratios used to perform the extraction, were used as a reference sample. The resulting spectrum is contained in FIG. 2 and labeled GWH. A distinct and strong absorbance peak is observable between about 300 nm and about 340 nm.

Example 1D

HPLC Chromatogram of Semiochemical GWH

A chromatograph of GWH was created to determine the chromatographic signature of active components of GWH. (See FIGS. 3 and 4.) HPLC parameters were:
Solvents: (1) Methanol and 0.1% acetic acid; (2) Water and 0.1% acetic acid
Ternary HPLC Pump: Gradient control
0-10 minutes: 100% methanol/acetic acid
10-12 minutes: Linear gradient to 100% water/acetic acid
12-20 minutes: 100% water/acetic acid
20-22 minutes: Linear gradient to methanol/acetic acid
22-40 minutes: 100% methanol/acetic acid
Column: Waters Novapak C18 RP 3.9×150 mm with guard column
Column heater: 25 C
Detection: 240 nm-340 nm
Injector: 50 uL loop.
The early eluting chromatograph contained signature peaks at around 5, around 6 and around 7 minutes, respectively. (See FIG. 3.) The late eluting chromatogram contained the signature peaks at around 32 minutes, around 34.5 minutes, around 36.5 minutes and around 42 minutes. (See FIG. 4.)

Example 1E

HPLC Chromatogram of Ninhydrin Derivatized GWH

Semiochemical GWH was derivatized with 0.1 g ninhydrin at 40° C. for 15 minutes. The derivatized GWH was then subjected to HPLC analysis with detection at 570 nm to detect primary amines. (See FIG. 5.) The resulting chromatogram had a strong peak at around 7 minutes and two weaker peaks at around 5 and around 6 minutes, respectively.

Derivatized GWH was also subjected to HPLC analysis with detection at 440 nm to detect secondary amines. (See FIG. 6.) The resulting chromatogram demonstrated a first strong and sharp peak around 34 minutes and a strong broad peak with two components eluting about 2 minutes later.

Example 1F

GC-MS of Semiochemical GWH

Tests of GWH were run on Direct Injection GC-MS. The GWH semiochemical was injected neat into a Hewlett Packard model 6890 GC with 5973 MSD in accordance with the parameters on the chromatogram. (See FIG. 7.) Analysis of the resulting mass spectrogram using NIST 98.1 provided the following non-limiting components of GWH: glycerin, N,N-dimethylurea, urea, 5-methyl-2,4-imidazolidinedione (5-methylhydantoin), creatinine, methyl hexadecanoate (methyl palmitate), hexahydro-3-(2-methylpropyl)-pyrrolo, [1,2-a]pyrazine-1,4-dione. See Table 4.

Example 2

Preparation and Testing of Semiochemical CP from Order Charcharhiniformes

Example 2A

Preparation and Repellent Testing of Semiochemical CP

CP was aerobically prepared from the head of a Caribbean reef shark (*C. perezii* Order Charcharhiniformes). The carcass head was processed in the manner described above for semiochemical GWH.

CP was tested for repellent activity against blacknose sharks and Caribbean reef sharks present in a population of 12 sharks. The sharks were stimulated with bait. An aerosol canister containing 6 fluid oz. of CP was then introduced to the 12 sharks. All sharks were visibly repelled from the feeding zone. (See Table 1). In three ensuing tests delivery of semiochemical CP from an aerosol canister again repelled competitively-feeding blacknose and Caribbean reef sharks.

Example 2B

UV-Vis Spectral Analysis of Ninhydrin-Derivatized CP

Semiochemical CP was derivatized with 0.1 g ninhydrin at 40° C. for 15 minutes. A uv-visible spectrogram was determined on a dual-beam Perkin Elmer Lambda 12 model. Neat CP was micron-filtered and loaded into quartz cuvettes. Representative uncontaminated solvents used in the extraction process, at the same ratios used to perform the extraction, were used as a reference sample.

The absorbance spectra of semiochemical CP derivatized with ninhydrin provided clear maxima observable at 440 nm (around 4 AU) and 570 nm (2.9 AU). (See FIG. 8.) With ninhydrin derivatized extracts, 440 nm absorbance indicates secondary amines and 570 nm absorbance indicates the presence of primary amines. When primary and secondary amines are not present, and the sample is derivatized with ninhydrin, absorbances at 440 nm and 570 nm are not observed. A uv-visible spectrum of 50% w/w ammonium acetate (a discredited shark repellent) in water, derivatized with 0.1 g ninhydrin at 40° C. for 15 minute showed no maxima at 440 nm or 570 nm. (See FIG. 9.)

Example 2C

GC-MS of Semiochemical CP

CP was tested with Direct Injection GC-MS. The CP semiochemical was injected neat into a Hewlett Packard model 6890 GC with 5973 MSD operating in accordance with the parameters on the chromatogram. (See FIG. 10.) Analysis of the mass spectrogram using NIST 98.1 resulted in the following non-limiting components of semiochemical CP: glycerin, N,N-dimethylurea, urea, 5-methyl-2,4-imidazolidinedione (5-methylhydantoin), creatinine, hexahydro-3-(2-methylpropyl)-pyrrolo[1,2-a]pyrazine-1,4-dione, 2,3-butanediol, N—N-dimethylformamide, 2-butoxyethanol, DL-methyltartronic acid, 1,4-dimethyl-piperazine, 2-(1,1-dimethylethoxy)-thiophene, hexahydro-pyrrolo[1,2-a]pyrazine-1,4-dione.

Example 3

Preparation and Testing of Semiochemical A1 from Order Carcharhiniformes

Example 3A

Preparation of Semiochemical A1

Semiochemical A1 was aerobically prepared from the carcass of a lemon shark (*N. brevirostris*) a nurse shark (*G. cirratum*) and a spiny dogfish (*S. acanthias*) (each species in Order Carcharhiniformes). The carcasses were allowed to decay aerobically for 10 days in a covered polypropylene container RT. The carcasses were then fully immersed in solvent in a polypropylene extraction vessel. The extraction solvent was 50:50 water:solvent, by weight. The solvent was 80% methanol, 17% ethanol, and 3% methyl isobutylketone. Extraction time was 6 months at 25° C. with slow agitation. The extraction was periodically sampled and terminated after components of the extraction eluted from HPLC at the signature peaks of about 5, about 6 and about 7 minutes. The extraction process was terminated by filtering to remove tissue. The resulting filtrate was containerized in a polypropylene container.

Example 3B

Testing of Semiochemical A1 for Repellent Activity

Semiochemical A1 was tested for repellent activity against blacknose sharks and Caribbean reef sharks present in a population of 15 sharks. The sharks were stimulated with bait. A 500 mL dose of A1 was introduced as a cloud to the 15 sharks. The sharks were visibly repelled from the feeding zone. (See Table 1).

Example 3C

HPLC Chromatograph of Semiochemical A1

A chromatograph of A1 was created to determine the chromatographic signature of active components of the A1 extract. (See FIGS. 3 and 4.) HPLC parameters were the same as above for GWH. The early eluting chromatogram contained signature peaks at around 5, around 6 and around 7 minutes, respectively. (FIG. 3.) The late eluting chromatogram contained the signature peaks at around 31, around 34, around 36 and around 42 minutes. (See FIG. 4.)

Example 3D

HPLC Chromatogram of Ninhydrin Derivatized A1

Semiochemical A1 was derivatized with 0.1 g ninhydrin at 40° C. for 15 minutes. The derivatized A1 was then subjected to HPLC analysis with detection at 570 nm to detect primary amines. (See FIG. 5.) The resulting chromatogram had a strong peak at around 7 minutes, a weaker peak at around 6 minutes and a very weak peak at around 5 minutes.

Derivatized A1 was also subjected to HPLC analysis with detection at 440 nm to detect secondary amines. (See FIG. 6.) The resulting chromatogram demonstrated a strong and sharp peak around 39 minutes and a strong broad peak with two components eluting about 2 minutes later.

Example 4

Preparation and Testing of Semiochemical A2 from Multiple Orders

Example 4A

Preparation and Repellent Testing of Semiochemical A2

Semiochemical A2 was aerobically prepared using the method described for GWH above from two lemon shark carcasses (*N. brevirostris*), one nurse shark carcass (*G. cirratum*), and one spiny dogfish carcass (*S. acanthias*) (orders Carcharhiniformes, Orectolobiformes, and Squaliformes, respectively).

A2 was tested for repellent activity against blacknose sharks and Caribbean reef sharks present together in a population of 12 sharks. The 12 sharks were stimulated with bait. A 500 mL dose of A2 was introduced as a cloud to the 12 sharks. The sharks were visibly repelled from the feeding zone. (See Table 1).

A2 was tested for repellent activity against lemon shark (*N. brevironstris* Order Carcharhiniformes). One lemon shark was successively placed in a state of tonic immobility and successively subjected to administration of A2 in a range from 7 mL to 30 mL via a syringe. Each administration resulted in the termination of tonic immobility. (See Table 1). A2 was also tested against lemon shark in a diluted form. 30 mL and 60 mL of 0.1 ppm semiochemical A2 (diluted with HPLC-grade water) was introduced to a tonically immobile lemon shark. Tonic immobility was terminated with the dilute repellent. These data support a conclusion that the semiochemical A2 will meet the goal of the Johnson-Baldridge effective repellent concentration of 0.1 ppm.

During tonic immobility studies, the semiochemical was delivered using a plastic syringe, which was not in contact with the specimen. The test solutions were released within 3 inches of the specimen's nose. Controls were established using separate syringes with seawater. Some controls were released with a high flow rate (30 mL/sec) in order to establish that sharks were not awakened by the jet of fluid over their noses.

A2 was also tested for repellent activity against bull shark (*C. leucas* Order Carcharhiniformes). (See Table 1). Bull shark is considered the most dangerous inshore species of shark. Two sharks were stimulated with bait and subjected to 500 mL of A2 in a cloud. The sharks were visibly repelled from the feeding zone.

A2 was tested using the Johnson-Baldridge Test with blacktip sharks (*C. limbatus* Order Carcharhiniformes). (See Table 1). A PVC tripod with a peristaltic metering pump set to meter out 1 mL/min of A2 repellent, a video camera and a transmitter was situated in the ocean. A 6 cubic meter observation area under the tripod was marked off and compensated for tidal changes. A fish head was secured under the tripod, within view of the camera. In a series of control-only experiments, solvent was pumped into the observation area at the prescribed flow once a blacktip shark was present. Thereafter, in a series of treatment experiments, a fish head was secured, the pump was started, and the behavior of one blacktip shark was observed. The fish head was protected for one hour in the presence of the stimulated shark until the battery of the pump was exhausted.

Example 4B

UV-Vis Spectrum of Semiochemical A2

A uv-visible spectrum of one-year-old A2 was compared with spectra from one-year old A13N and one-year-old SQ1. All three of these extracts demonstrated good flight responses in target sharks. The three spectra together demonstrate matching strong peaks in the 300 nm range. (See FIG. 11.)

Example 4C

Head Space-GC-MS and Proposed Components of A2

A 10-mL aliquot of shark fluid was placed in a 100-mL headspace vial and capped with a Teflon butyl rubber septa. The vial was allowed to equilibrate at 30° C. overnight prior to analysis. The sample headspace was injected into a Hewlett Packard model 6890 GC with 5973 MSD operating under the following system conditions.

| | |
|---|---|
| Column: | DB-5 40 m × 0.18 mm × 0.40 µm film |
| Carrier: | helium @ 1 mL/min |
| Injection: | 10 cc manual cryo, split 25:1 @ 250° C. |
| Oven: | 40° C. to 280° C. @ 10° C./min |
| Trans. Line: | 280° C. |
| MSD: | Scan 20-500 m/z. |

A total ion chromatogram from Head Space Gas Chromatographic-Mass Spectrometric analysis of the semiochemical repellent A2 is shown in FIG. 17. Peaks are labeled with proposed chemical components of A2.

Components identified by headspace in combination with direct injection GC-MS are shown in Table 2. The components were identified with the aid of the NIST 2002 mass spectral search database and are tentative. Structures are proposed and are not intended to be limiting on the structure or makeup of the obtained semiochemical solution A2.

Example 4D

Direct Injection GC-MS and Proposed Components of A2

Semiochemical A2 was injected neat into a Hewlett Packard model 6890 GC with 5973 MSD operating under the following system conditions.

| | |
|---|---|
| Column: | DB-5 40 m × 0.18 mm × 0.40 μm film |
| Carrier: | helium @ 1 mL/min |
| Injection: | 2 μL, splitless @ 280° C. |
| Oven: | 40° C. hold 5 min, to 300° C. @ 10° C./min, hold 5 min |
| Trans. Line: | 300° C. |
| MSD: | Scan 20-700 m/z. |

A total ion chromatogram from Direct Injection Gas Chromatographic-Mass Spectrometric analysis of the semiochemical repellent A2 is shown in FIG. 18. Peaks are labeled with proposed chemical components of A2. Structures are proposed and are not intended to be limiting on the structure or makeup of the obtained semiochemical A2.

Components identified by headspace and direct injection GC-MS are shown in Table 2. The components were identified with the aid of the NIST 2002 mass spectral search database and are tentative.

TABLE 2

Summary of GC-MS Results from Various Analyses

| Headspace GC-MS | Direct Injection, small | Direct Injection, large |
|---|---|---|
| ethanol | ethanol | Detector filament off |
| acetic acid, methyl ester | acetic acid, methyl ester | " |
| 2-methylpentane | | " |
| 3-methylpentane | | " |
| hexane | | " |
| ethyl acetate | ethyl acetate | ethyl acetate |
| | | acetic acid |
| 2,4-dimethylpentane | | |
| 2-methyl-1-pentene | | |
| 1-ethoxy-2-methylpropane | | |
| 3,3-dimethylpentane | | |
| 2-methylhexane | | |
| cyclohexane | | cyclohexane |
| 3-methylhexane | | |
| 1,1-dimethylcyclopentane | | |
| 1,3-dimethylcyclopentane | | |
| 1,2-dimethylcyclopentane | | |
| heptane | | heptane |
| 2,2-dimethylhexane | | |
| methylcyclohexane | | |
| 2,4-dimethylhexane | | |
| methyl isobutyl ketone | methyl isobutyl ketone | methyl isobutyl ketone |
| 1,2,3-trimethylcyclopentane | | |
| 2,3-dimethylhexane | | |
| 2-methylheptane | | |
| toluene | toluene | toluene |
| 1,3-dimethylcyclohexane | | n,n-dimethylurea |
| octane | | urea |
| 1,2-dimethylcyclohexane | | myristic acid, methyl ester |
| 1,3-dimethylcyclohexane | | myristic acid, ethyl ester |
| 2-methyloctane | | palmitoleic acid, methyl ester |
| 1,2,3-trimethylcyclohexane | | palmitic acid, methyl ester |
| ethylcyclohexane | | palmitic acid |
| 1,1,3-trimethylcyclohexane | | ethyl-9-hexadecenoate |
| 1,2,4-trimethylcyclohexane | | palmitic acid, ethyl ester |
| 1,3-diethylcyclopentane | | 8-octadecenoic acid, methyl ester |
| 2,3-dimethylheptane | | stearic acid, methyl ester |
| 1,2,4-trimethylcyclohexane | | ethyl oleate |
| 3-methyloctane | | stearic acid, ethyl ester |
| octahydropentalene | | arachidonic acid |
| 1,2,4-trimethylcyclohexane | | |
| 1,2,4-trimethylcyclohexane | | |
| 1-ethyl-3-methylcyclohexane | | |
| 1-ethyl-4-methylcyclohexane | | |
| propylcyclohexane | | |

Example 4E

LC-MS and Proposed Components of A2

Semiochemical A2 was diluted 1:1 (v/v) for analysis with HPLC grade water. The resulting solution was filtered through a 0.45-μm Gelman Acrodisc Nylon syringe filter prior to analysis. The filtered solution was transferred to autosampler vials for analysis.

The sample was analyzed using atmospheric pressure chemical ionization (APCI) in the positive ionization mode. In addition to mass spectrometry (MS), MS$^n$ was also employed with n equal to 3 to afford fragmentation of the parent ion. The LC-MS conditions are given below:

| Pump: | Agilent 1100 Series Binary Pump with Degasser |
| --- | --- |
| Detectors: | Agilent 1100 Multi Wavelength Detector and LC/MSD Trap |
| Column: | YMC ODS-AQ column, 4.6 × 250 mm with a 5-μm particle |
| Wavelength: | 210 nm |
| Run Time: | 20 minutes |
| Autosampler: | 6 minute equilibration time between sample injections |
| Injection Volume: | 10 microliter |
| Mobile Phase: | A) 0.1% Formic acid in methanol |
| | B) 0.1% Formic acid in water |

| | Time (min.) | Flow (mL/min.) | % A | % B |
| --- | --- | --- | --- | --- |
| Gradient | Initial | 1.00 | 5 | 95 |
| | 5.00 | 1.00 | 5 | 95 |
| | 15.00 | 1.00 | 100 | 0 |
| | 20.00 | 1.00 | 100 | 0 |

A total ion chromatogram from Liquid Chromatographic-Mass Spectrometric analysis of the semiochemical repellent A2 is shown in FIG. 19. Peaks are labeled with the mass/charge (m/z) ratio of proposed chemical components of A2. Table 3, below, also contains this data.

TABLE 3

Component Observed by LC-MS

| Retention Time (min) | Observed Mass (M + 1) | Comments |
| --- | --- | --- |
| 3.7 | 147.4 | Strong |
| 4.1 | 151.1 | Strong |
| 4.2 | 132.7 | Strong |
| 4.2 | 207.2 | Strong |
| 4.2 | 227.1 | Strong |
| 4.2 | 263.1 | Strong |
| 4.3 | 114.6 | Weak |
| 5.5 | 150.5 | Weak |
| 6.0 | 228.9 | Weak |
| 7.5 | 132.5 | Weak |
| 8.4 | 137.4 | Weak |
| 8.4 | 182.2 | Weak |
| 11.6 | 268.2 | Weak |
| 12.5 | 269.6 | Strong |
| 12.8 | 166.3 | Strong |
| 15.2 | 371.9 | Weak |

Note:
observed mass is report as the M + 1 ion; the molecular weights are generally one mass unit lower than the observed mass.

Based on the LC-MS data, the following structures are proposed. However, structures are proposed and are not intended to be limiting on the structure or makeup of the obtained semiochemical A2 as characterized by the LC-MS.

Compounds that were detected using LC-MS are described below. A typical total ion chromatogram generated in the study is shown in FIG. 19. Supporting data are also included in Table 3. The structures that are proposed below are tentative assignments.

Retention time 3.7 min, m/z 147.2
This unknown was tentatively assigned as

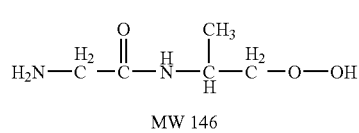

MW 146

Retention time 3.9 min, m/z 151.3
It appears that the molecular weight of this unknown is 150 and ions at M/z 189 and 227 are probably potassium adducts. However, m/z 227 may belong to a slightly later eluting component (see one of the compounds eluting at 4.2 minutes). Limited fragmentation pattern and the molecular weight would support the tentative proposed structure (II) of tartaric acid in FIG. 2:

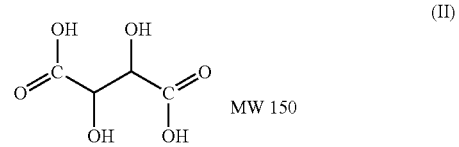

Retention time, 4.2 min
Last significant peak is at m/z 263 and intense fragment ions at m/z 227, 207, 189, 151, 132.7 would appear to support a tentative proposed structure (III) of dibutyl tartarate.

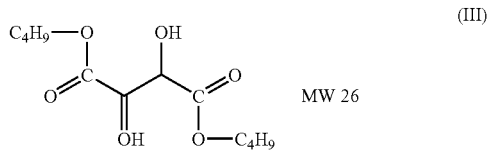

The possibility also exist that the above ions are related to different compounds. There is a question also whether m/z 263 may be a protonated dimer of a component at m/z 131 (leucine, IV), and m/z 207 could be the monobutyl ester of tartaric acid. Again, peak at m/z 227 may be attributed to the next eluting component (see Structure VI below). Other structures were proposed for molecular weight 131 including creatine, 3-hydroxy-dl-proline, leucine (IV), or (V).

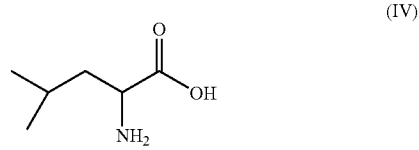

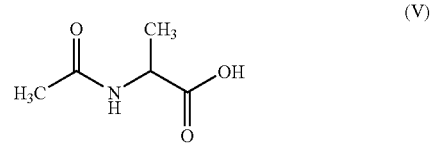

Retention time 4.2 min, m/z 227
This has been tentatively assigned before as (VI).

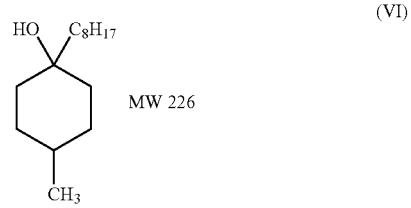

Retention time 7.5 min, m/z 132.7
The molecular weight appears to be 131. The components mentioned at retention time of 4.2 minutes are also possible for this component.

Retention time 11.6 min, m/z 268.2
Molecular weight of this unknown is 267. At the beginning, oleylamine or pyrrolidine structure (VII) was considered for this unknown, but second derivative fragment at m/z 135.9 (M-132) could not be explained for these structures. An adenosine structure (VIII) is tentatively proposed for this unknown.

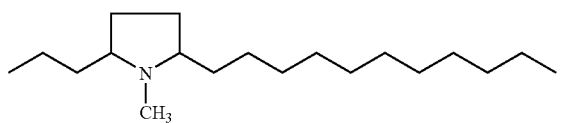
(VII)

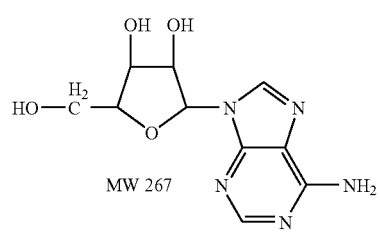
(VIII)

Retention time 12.5 min, m/z 269.5

An oleyl alcohol (IX) is proposed for this unknown.

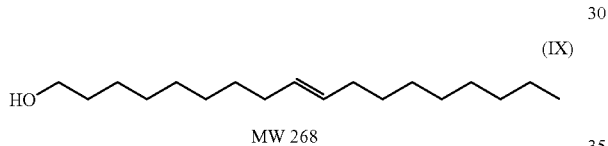
(IX)

Retention time 12.8 min, m/z 166.3

This is a nitrogen containing compound with molecular weight of 165. This compound could be phenylalanine (X). The second derivative data would support this assignment.

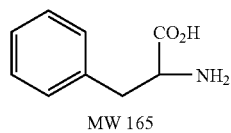

Ret. time 15.2 min, m/z 372.

This compound was observed in the previous study (R03-0299). A component at m/z 330 in the first study (R03-0215) was tentatively identified. This component is 42 mass units higher than the earlier identified compound and could be due to a tentatively proposed structure (XI). Fragmentation provides loss of 18 (loss of hydroxyl as water) and another loss of 17 mass units.

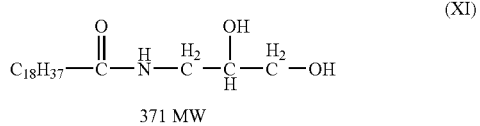
(XI)

Example 4F

HPLC Chromatographs of Ninhydrin-Derivatized Semiochemical A2

Semiochemical A2 was derivatized with 0.1 g ninhydrin for two hours at 40° C. The derivatized A2 was then subjected to HPLC analysis with detection at 570 nm to detect primary amines. (See FIG. 13.) The following system configuration was used with injection volume and mobile phase as set forth on the chromatograph in FIG. 13:

| | |
|---|---|
| Column: | C18, reversed phase |
| Flow rate: | 1 ml/min |
| Column temperature: | 35° C. |

The method produced around 5 characteristic peaks between 1 and 2 minutes for primary amines at 570 nm. With detection at 440 nm for secondary amines and injection volume and mobile phase as set forth in FIGS. 14 and 15, the method likewise produced around 5 characteristic peaks between 1 and 2 minutes. (See FIGS. 14 and 15.) An entity at both detection wavelengths is observed at 4.8 minutes with a trace concentration.

Example 4G

FTIR Spectrum of Semiochemical A2

An FTIR analysis was performed on semiochemical A2 using a waterless sample from the water-insoluble phase described above is set on a KBr crystal. A scans from 1100 nm to 3500 nm in butanol and diethylether of a semiochemical indicated the following groups:

| | |
|---|---|
| 2800-3000 nm | Asymmetric and symmetric CH3 groups |
| 1300-1400 nm | Scissor, asymmetric, and symmetric CH3 groups |
| 1126.00 nm | C—O bond stretching |
| 1434.56 nm | C—O bond stretching |
| 1637.28 nm | C=C bond stretching |
| 2846.60 nm | C—H bond stretching |
| 2916.50 nm | C—H bond stretching |
| 2951.46 nm | C—H bond stretching |
| 3321.94 nm | OH bond stretching, indicating alcohols with the above three stretches. |

(See FIG. 16.)

Example 5

Preparation of Semiochemical CL from Order Carcharhiniformes

Semiochemical CL solution from a carcass of *C. limbatus* (Order Carcharhiniformes) was aerobically prepared using the method described for GWH above. During the aerobic preparation process, the extraction vessel was sampled at 0, 7, 21 and 40 days to determine development of the semiochemical uv-vis signature peak at 300 nm. (See FIG. 12.) Signature absorbance at around 300 nm increased as extraction proceeded. A 300 nm shoulder was barely perceptible at 0 days and increased throughout 7, 21 and 40 days to a distinct peak at about 40 days.

Example 6

Preparation and Testing of Semiochemicals CPP and GCC from Order Carcharhiniformes

Example 6A

Preparation of Semiochemicals CPP and GCC

CPP and GCC were aerobically prepared from the head of a sandbar shark (*S. plumbeus*) and the cross section behind the pectoral fins of a tiger shark (*G. cuvieri*), respectively. Each carcass is within Order Carcharhiniformes. The extraction process was as described for GWH above.

Example 6B

Testing of Extracts CPP and GCC for Repellent Activity

CPP was tested for repellent activity against blacknose sharks and Caribbean reef sharks present together in a population of 7 sharks. The sharks were stimulated with bait. A 500 mL dose of CPP was introduced as a cloud to the 7 sharks. The sharks were visibly repelled from the feeding zone. (See Table 1).

GCC was tested for repellent activity against the highly migratory (pelagic) non-inshore blue shark (*P. glauca* Order Carcharhiniformes) in a population of 2 sharks. The sharks were stimulated bait and acoustical stimulation. A 500 mL dose of GCC was introduced as a cloud to the 2 sharks. The sharks were visibly repelled from the feeding zone. (See Table 1).

Example 7

Preparation and Testing of Semiochemical A13N from Order Carcharhiniformes

Example 7A

Preparation of Semiochemical A13N and UV-Vis Spectrum

A13N was prepared by mixing, in equal parts, three previously prepared semiochemicals, A1, A3 and N. A13N contained semiochemicals from a lemon shark carcass (*N. brevirostris*), a nurse shark carcass (*G. cirratum*), and a spiny dogfish carcass (*S. acanthias*) (each species in Order Carcharhiniformes). A1 was prepared as described above. A3 was prepared in the same manner as A1. N was prepared from the carcass of a nurse shark using the method described for GWH above. A uv-visible spectrum of a one-year-old sample of the mixed semiochemical A13N was prepared as discussed in Example 4B above. The spectrum contained the signature strong peak in the 300 nm range. (See FIG. 11.)

Example 7B

Testing of A13N for Repellent Activity

A13N was tested for repellent activity against a blacknose shark and a Caribbean reef shark. A 500 mL dose of A13N was introduced as a cloud to the two sharks, which were presently stimulated with bait and acoustic stimulation. The sharks were visibly repelled from the feeding zone.

Example 8

Preparation and Testing of Semiochemical B from Order Lamniformes

Semiochemical B was aerobically prepared from the cross-section behind the first dorsal fin of a shortfin mako shark (*I. oxyrhincus* Order Lamniformes). The carcass portion was allowed to decay aerobically for 10 days in a covered polypropylene container RT. The carcass portion was then fully immersed in solvent in a glass extraction vessel. The extraction solvent was 50:50 water:acetone, by weight. Extraction time was 6 months at 25° C. with slow agitation. The extraction was periodically sampled and terminated after components of the extraction eluted from HPLC at the signature peaks of about 5, about 6 and about 7 minutes. The extraction process was terminated by filtering to remove tissue. The resulting filtrate was containerized in a polypropylene container.

Composition B2 was aerobically prepared from the cross-section behind the first dorsal fin of a shortfin mako shark in one polypropylene extraction vessel. The extraction solvent was 100% water. Extraction time was 6 months at 25° C. with slow agitation. The extraction process was terminated by filtering to remove tissue. The resulting filtrate was containerized in a polypropylene container.

B was tested for repellent activity against blacknose sharks and Caribbean reef sharks present together in a population of 12 sharks. A 200 mL dose of B was introduced as a cloud to the 12 sharks, which were presently stimulated with bait. The sharks were visibly repelled from the feeding zone. (See Table 1).

Composition B2 was likewise tested for repellent activity against blacknose sharks and Caribbean reef sharks present together in a population of 6 sharks. A 1 liter dose of B2 was introduced as a cloud to the 6 sharks, which were presently stimulated with bait. No behavioral change was noted and feeding continued. (See Table 1).

Example 9

Preparation and Testing of Semiochemicals ML1 and ML2 from Order Lamniformes Extracts ML1 and ML2 were separately aerobically prepared from two livers of a shortfin mako shark (*I. oxyrhincus* Order Lamniformes) in two polypropylene extraction vessels. The livers were initially allowed to decay aerobically for 10 days in covered polypropylene containers at room temperature (RT). The livers were then fully immersed in solvent in polypropylene extraction vessels. The extraction solvent was 50:50 water:acetone, by weight. Extraction time was 6 months at 25° C. with slow agitation. The extraction was periodically sampled and terminated after components of the extraction eluted from HPLC at the signature peaks of about 5, about 6 and about 7 minutes. The extraction process was terminated by filtering to remove tissue. The resulting filtrate was containerized in a polypropylene container.

ML1 and ML2 were tested for repellent activity against blacknose sharks and Caribbean reef sharks present together in two populations of 8 sharks. The sharks were stimulated with bait. Respective 700 mL doses of ML1 and ML2 were introduced to respective shark populations as a cloud. The sharks were visibly repelled from the feeding zones. (See Table 1).

Example 10

Preparation and Testing of Semiochemical SQ1 from Order Squaliformes

SQ1 was aerobically prepared from the carcass of a deep water Cuban dogfish (*S. cubensis*, Order Squaliforme) in one polypropylene extraction vessel as described for GWH above. A uv-visible spectrum of semiochemical SQ1 one year after the extraction process was terminated. The spectrum was prepared as discussed in Example 4B above. The spectrum contained the signature strong peak in the 300 nm range. (See FIG. 11.)

SQ1 was tested for repellent activity against blacknose sharks and Caribbean reef sharks present together in a population of 12 sharks. A 250 mL dose of SQ1 was introduced as a cloud to the 12 sharks, which were stimulated with bait. The sharks were visibly repelled from the feeding zone. (See Table 1).

Example 11

Preparation and Testing of Semiochemicals N2 and BB1 from Order Orectolobiformes N2 and BB1 were aerobically prepared from the carcasses of a nurse shark (*C. cirratum*, Order Orectolobiformes, Family Ginglymostomatidae) and a brownbanded bamboo shark (*C. punctatum*, Order Orectolobiformes, Family Hemiscyllidae) in separate polypropylene extraction vessels. The carcasses were initially allowed to decay aerobically for 10 days in a covered polypropylene container RT. The carcasses were then fully immersed in solvent in a polypropylene extraction vessel. The extraction solvent was 50:50 water:solvent, by weight. The solvent was 80% methanol, 17% ethanol, and 3% methyl isobutylketone. Extraction time was 6 months at 25° C. with slow agitation. The extraction was periodically sampled and terminated after components of semiochemicals eluted from HPLC at the signature peaks of about 5, about 6 and about 7 minutes. The extraction process was terminated by filtering to remove tissue. The resulting filtrate was containerized in a polypropylene container.

N2 was tested for repellent activity against a lemon shark (Order Carcharhiniformes, Family Carcarhinidae, *N. brevirostris*). A 10 mL dose of N2 was introduced from a syringe into the environment of the shark in a tank. Aversive swimming behavior was observed. (See Table 1).

BB1 was tested for repellent activity against a lemon shark (Order Carcharhiniformes, Family Carcarhinidae, *N. brevirostris*). A 10 mL dose of BB1 was introduced from a syringe into the environment of the shark in a tank. Aversive swimming behavior was observed. (See Table 1).

Example 12

Repelling of Mako Shark of Order Lamniformes

A juvenile Mako shark (Order Lamniformes, Family Lamidae, Genus *Isurus*) was repelled by semiochemical repellent GCC. A buoy line baited with squid, blue fish, and striped bass was in the water. Mako sharks are known to attack swordfish, and eat prey such as blue fish and striped bass when it is available for consumption. A 500 mL charge to the line under CO2 pressure was applied. Diptubes were ¼" HPDE. (See FIG. 30.) The bait was not taken.

After coming in contact With the GCC, the Mako retreated and did not appear again. Subsequently, the shark could not be lured back to the site despite the application of three types of stimulants and several hours applying traditionally adequate scent and bait. After extensive attempts to re-lure the shark, only new blue sharks appeared well after the repellent would be expected to have completely dispersed. Generally, when repellent is not deployed, sharks remain in the area where scent and bait has been administered for an extended period of time (up to many hours). The failure of the shark to return after fleeing the exposure to GCC was interpreted as support for the strong action of the GCC semiochemical against the juvenile Mako shark.

The test was done under the following conditions:
Live bait: Bluefish (2)
Carcass line: Bluefish (2) and striped bass (2)
Chum: Bunker, striped bass, and bluefish
Acoustics: Mako Magnet (http://www.makomagnet.com/)
Orange buoy lines with diptubes (see FIG. 30.)

Example 13

Repellent Tests of Semiochemicals from Four Different Orders

Semiochemical solutions from four orders of shark were prepared as described for semiochemical GWH above, using carcasses from *Negaprion brevirostris, Ginglymostoma cirratum, Squalus cubensis*, and *Isurs oxyrinchus*. All solutions were found to generally exhibit the sample characteristic absorbance maxima in the UV region. (See FIG. 2.) The four semiochemical solutions were derived from four different families of shark, Family Carcarhinidae, Ginglymostomatidae, Squalidae and Lanmidae, respectively. Each semiochemical exhibited the same repellency effects on other species, the common absorbance maxima, therefore, became a focus of finding an active chemical repellent entity. (See, e.g., Table 1). For example, a 100 mL dose of semiochemical solution prepared from spinal extracts of *Squalus cubensis* effectively repelled a small feeding school of *Carcharhinus perezi* and *Carcharhinus acronatus*.

Example 14

Repellent Test Controls

The following compounds have been established as effective controls in stimulated free-swimming sharks, tonic immobility tests and non-stimulated free-swimming sharks under chemical repellent evaluation: seawater (dose ranges 100 ul to 1000 ml); HPLC grade micron-filtered water (dose ranges 1 ml to 10 ml); methanol/ethanol/methyl isobutyl ketone/water solution (dose at approx 500 ml); (solvent for A, A2, A13N, SQ1, CPP, GWH, GCC, CP, N2 and BB1); methanol/ethanol/methyl isobutyl ketone solution (dose ranges 1 ml to 6 ml) (50% of solvent for A, A2, A13N, SQ1, CPP, GWH, GCC, CP, N2 and BB1); diethylene glycol monoethyl ether (dose ranges 1 ml to 6 ml); acetone/water solution (dose at approx 500 ml) (solvent for B, B2, ML1, and ML2).

Example 15

GC-MS of Composite of CF-Composite from Two *C. falciformis* Heads

Semiochemical CF-Composite was prepared from two *C. falciformis* heads subject to extraction with polar solvent as described for A2 above. *C. falciformis* is a pelagic Carcarhiniform known as the silky shark (Order Carcharhiniforme).

Tests were run by Direct Injection on a quadrupole GC-MS system with a selective mass detector, as described for GWH above. The resulting gas chromatogram is reported in FIG. 20. Analysis of the resulting mass spectrogram using NIST 98.1 provided the following resulting non-limiting components of CF-Composite: urea, 1-(2-hydroxyethyl)-2-imidazolidinone, ethyl acetate.

Example 16

GC-MS of Semiochemical B-Composite from *P. glauca* Head, Body and Tail

B-Composite was prepared from a head, body and tail of *P. glauca* the pelagic blue shark (Order Carcharhiniforme) subject to extraction as described for GWH above.

Tests were run by Direct Injection on a quadrupole GC-MS system with a selective mass detector, as described for GWH above. The resulting gas chromatogram is reported in FIG. 21. Analysis of the resulting mass spectrogram using NIST 98.1 provided the following resulting non-limiting components of B-Composite: glycerin, N,N-dimethylurea, urea, 5-methyl-2,4-imidazolidinedione (5-methylhydantoin), creatinine, methyl hexadecanoate (methyl palmitate), propanoic acid, dimethyl-propanedioic acid (dimethylmalonic acid), butanoic acid (butyric acid), 3-methyl-butanoic acid, 2-methyl-butanoic acid (isovaleric acid), phenol, 4-morpholinepropionitrile, n-hexadecanoic acid (palmitic acid), 10-octadecenoic acid, methyl ester (methyl elaidate), (E)-9-octadecenoic acid (eliadic acid).

Example 17

Comparison of Components Detected in Four Semiochemicals by GC-MS

The components of semiochemicals GWH, CF-Composite, CP and B-Composite were compared to determine shared chemistry. The comparison is in Table 4.

TABLE 4

Comparison of components of Four Semiochemicals in GC-Mass-Spectrometry (values represent relative percentage matches with NIST 98.1 library)

| Component | GWH | CF-Composite | CP | B-Composite |
|---|---|---|---|---|
| glycerin | 64 | | 72 | 64 |
| N,N-dimethylurea | 91 | | 91 | 91 |
| urea | 78 | 56 | 64 | 72 |
| 5-methyl-2,4-imidazolidinedione (5-methylhydantoin) | 86 | | | 86 |
| creatinine | 52 | | 64 | 93 |
| methyl hexadecanoate (methyl palmitate) | 95 | | | 94 |
| hexahydro-3-(2-methylpropyl)-pyrrolo [1,2-a] pyrazine-1,4-dione | 72 | | 56 | |
| propanoic acid | | | | 94 |
| dimethyl-propanedioic acid (dimethylmalonic acid) | | | | 80 |
| butanoic acid (butyric acid) | | | | 64 |
| 3-methyl-butanoic acid | | | | 78 |
| 2-methyl-butanoic acid (isovaleric acid) | | | | 83 |
| phenol | | | | 90 |
| 4-morpholinepropionitrile | | | | 53 |

TABLE 4-continued

Comparison of components of Four Semiochemicals in GC-Mass-Spectrometry (values represent relative percentage matches with NIST 98.1 library)

| Component | GWH | CF-Composite | CP | B-Composite |
|---|---|---|---|---|
| n-hexadecanoic acid (palmitic acid) | | | | 95 |
| 10-octadecenoic acid, methyl ester (methyl elaidate) | | | | 53 |
| (E)-9-octadecenoic acid (eliadic acid) | | | | 74 |
| 1-(2-hydroxyethyl)-2-imidazolidinone | | 45 | | |
| ethyl acetate | | 72 | | |
| 2,3-butanediol | | | 78 | |
| N-N-dimethylformamide | | | 43 | |
| 2-butoxyethanol | | | 72 | |
| DL-methyltartronic acid | | | 50 | |
| 1,4-dimethyl-piperazine | | | 64 | |
| 2-(1,1-dimethylethoxy)-thiophene | | | 64 | |
| hexahydro-pyrrolo [1,2-a] pyrazine-1,4-dione | | | 62 | |

Example 18

Comparison of UV-Vis Spectra of Semiochemicals of Different Species and Different Carcass Parts of Shark Semiochemicals of different species and carcass parts of shark were subjected to uv-vis spectral analysis according to the above-discussed method. (See FIG. 2.) All extracts demonstrated a peak around 300 nm. The control (solvent-first line) demonstrates no absorbance shoulder around 300 nm. The semiochemical showing the strongest absorption in the signature 300 nm range is semiochemical GWH, which is an extraction of a great white shark head.

Semiochemical abstracts GWH, GCC, N2 were demonstrated to have repellent activity. (See Table 1).

Example 19

Shelf-Life of A2 and N2

During a day of field tests on semiochemical repellents, experiments with a more-than-one-year-old sample of A2 semiochemical repellent evoked only weak measurable flight response in a variety of sharks. Similar results were obtained with a more-than-one-year-old sample of N2. Because both A2 and N2 had evoked strong flight responses in many tests in prior months, it was hypothesized that the A2 and N2 test samples had been degraded and the semiochemical components had been lost or reduced in concentration.

HPLC Chromatograph Analysis

Early eluting chromatograms of degraded A2 and N2 (FIGS. 22 and 23) were compared to chromatograms of GWH and A1 (FIGS. 3 and 4) to determine the chromatographic signature of active components of the GWH and A1 extracts. HPLC parameters were as discussed above. The chromatogram of GWH showed a strong peak around 7 minutes, a weaker peak at around 6 minutes and a weak peak at around 5 minute (See FIG. 3.) The chromatograms of degraded A2 and N2 contained no peak at around 7 minutes, a peak comparable with the chromatogram of GWH at around 6 minutes and very weak peaks at 5.2 and 5.4 minutes, respectively. (See FIG. 22.) The peaks at 5.2 and 5.4 minutes had no clear correlation with the 5 minute peak of GWH.

Late eluting chromatograms of A2 and N2 were likewise compared to GWH and A1. (FIGS. 4 and 23.) HPLC parameters were as discussed above. The chromatograms of GWH and A1 showed distinctive and expected peaks at around 34 minutes having a notably weaker earlier peak within the 34 minute peak. The GWH and A1 chromatograms likewise showed the expected broad peak about 2 minutes following the 34 minute peak, with two maxima within the broad peak. The late eluting chromatograms of degraded A2 and N2 had unexpectedly sharp peaks at around 32 minutes and somewhat sharp peaks about 2 minutes later that were distinctly different from the expected broad peak of an active semiochemical such as GWH or A1.

Example 20

Administration of Semiochemical Repellent Using a Canister

An aerosol container with a continuous-release actuator was pressurized with 6 fluid oz. of semiochemical CP. The container was constructed to be asymmetrically weighted so that it would not lie on its axis on the surface of the water. In this test, the container was lighter at its base and heavier at its discharging end. The actuator was depressed, initiating release of the CP semiochemical and thrown into a group of 12 feeding sharks. During the pressurized discharge of the extract, the canister moved erratically on the surface of the water. At times the semiochemical was expelled into the air creating a mist that subsequently fell on the surface of the water. At times, the semiochemical was expelled directly into the water. The feeding sharks were drawn to the erratic activity of the canister. When the sharks encountered the cloud of discharged semiochemical near the surface of the water, they fled. In a control, similar pressurized containers with 100% methanol instead of semiochemical were similarly thrown into a population of feeding sharks. The sharks were drawn to the container and did not flee. An expended container was recovered from the water with shark bite marks on it.

Example 21

Administration of Semiochemical Using a Remote Controlled Raft

A two liter repellent chamber was filled with repellent on a remote controlled raft. The raft was anchored at a sandbar where a shark might be expected to enter a shallow swimming area. A radio receiver was connected to a pump on the raft. The pump with its own power source was connected to the two liter chamber with tubing. The two liter chamber was provided a check valve for rapid build up of pressure from the pump. Tubing was then fixed from the two liter chamber exit portal away from the raft as a discharge tube. The tubing was not sufficiently long enough to enter the water where the raft was floating. The tubing exiting from the chamber was capped with a pressure release cap.

A person remote from the raft signaled the radio receiver to trigger activation of the pump. The pump compressed air into the 2 liter plastic tank. Head pressure in the chamber increased quickly. Once enough pressure built up, the cap popped off of the tubing and repellent was rapidly sprayed over a 2 meter surrounding area at about 20-30 psi. The chamber was emptied within 20 seconds.

Example 22

Administration of Semiochemical Using a Pressurized Directional Device

A pressurized gun as described in FIG. 28 was charged with degraded semiochemical A2. A population of about 10 blacknose sharks and Caribbean reef sharks were stimulated with feed. A swimmer entered the water with the pressurized gun. When sharks approached, the swimmer discharged the first chamber in the direction of the sharks by pointing the directional nozzle and triggering the compressed gas canister. The sharks were partially repelled. The swimmer then discharged the second pressurized chamber in the direction of the sharks. The sharks were again partially repelled.

Example 23

Administration of Semiochemical on a Longline

A mass of elasmobranch carcass treated with polar solvent according to the methods of the invention is pressed together and placed on a longline hook at the end of a gangion. The hook is then baited, e.g., with mackerel. The longline is placed into the water. Sharks are deterred from striking the hook because of the semiochemical diffusing from the polar-solvent-treated-elasmobranch-carcass mass near the hook. Fish are not deterred. As a result, a tuna is caught on the hook.

Example 24

Preparation of Semiochemical in Jelly Form that Dissolves Over Time in Water

Semiochemical was prepared in a jelly form that would dissolve over time when placed in water. 100 g diethylene glycol monoethyl ether was warmed to around 40° C. in a mixture with 2 g of hydroxypropylmethylcelluose under heavy agitation. The mixture was allowed to cool with slow mixing to about 30° C. At around 30 C, around 20 mL of semiochemical CP was added with an eye dropper over about 2 minutes with slow mixing. The mixture was then cooled to room temperature. A firm gel was formed over night. About 10 g of gel was placed in about 125 mL of water. In about 8 hours the gel was fully dissolved. Such administration of semiochemical could be particularly advantageous to divers and snorklers who would want to repel elasmobranchs but who would not want to repel fish.

What is claimed is:

1. A process for making an elasmobranch repellent comprising the step of (i) extracting a semiochemical from a carcass of an elasmobranch by exposing said carcass to a polar solvent system that is less than 100% water, wherein the polar solvent system comprises water and a polar solvent in a ratio of about 50% water to about 50% polar solvent, by weight, (ii) detecting the presence of semiochemical elasmobranch repellent activity in the solvent wherein the presence of semiochemical elasmobranch repellent activity is detected by performance of high performance liquid chromatography (HPLC) and/or testing for repellent activity against a shark; and upon detection of semiochemical elasmobranch repellent activity (iii) filtering said repellent from said carcass.

2. The process of claim 1 wherein a portion of said carcass is exposed to a polar solvent.

3. The process of claim 1 wherein said carcass is aerobically decayed to a degree of decomposition beyond the onset of rigor mortis prior to exposure to said polar solvent.

4. The process of claim 1 wherein said carcass is aerobically decayed to a degree of decomposition between the onset of rigor mortis and before complete putrefaction prior to exposure of said carcass to said polar solvent.

5. The process of claim 1 wherein said carcass is completely immersed in said polar solvent.

6. The process of claim 1, wherein the presence of semiochemical elasmobranch repellant activity is detected by performance of high performance liquid chromatography (HPLC) and wherein the repellant has three characteristic peaks on a high performance liquid chromatography (HPLC) chromatogram with relative peaks detected in the range between approximately 240 nm to approximately 340 nm at about 5, about 6 and about 7 minutes, the relative peak at about 7 minutes is greater than the relative peaks at about 5 minutes and about 6 minutes, and the HPLC chromatogram has the following characteristics:

| | |
|---|---|
| Column: | Novapak 0.5u C18 reversed phase |
| Flow rate: | 0.5 ml/min |
| Mobile phase: | A: Methanol, 0.1% acetic acid |
| | B: Water, 0.1% acetic acid |
| Gradient: | 0-10 minutes 100% mobile phase A |
| | 10-12 minutes, 0% mobile phase A, |
| | 100% mobile phase B, linear |
| | 12-20 minutes 100% mobile phase A, linear |
| | 22-60 minutes, 100% mobile phase A |
| Injection: | 50 ul into a 50 ul loop |
| Column temperature: | 25° C. |

7. The process of claim 1, wherein the polar solvent system comprises a polar solvent selected from the group consisting of: n-propanol, iso-propanol, glycol ethers, methanol, ethanol, acetic acid, hydrochloric acid, butanol, dimethylsulfoxide, a short-chain aldehyde, ketone, and combinations thereof.

8. The process of claim 1, wherein the polar solvent system comprises water, methanol, ethanol, and methyl isobutyl ketone.

9. The process of claim 8, wherein the polar system comprises about 50% water by wt, about 40% methanol by wt., about 8.5% ethanol by wt., and about 1.5% methyl isobutyl ketone by wt.

\* \* \* \* \*